US006284756B1

(12) United States Patent
Chirgadze et al.

(10) Patent No.: US 6,284,756 B1
(45) Date of Patent: Sep. 4, 2001

(54) ANTITHROMBOTIC AGENTS

(75) Inventors: Nickolay Y Chirgadze, Carmel; Richard W Harper, Indianapolis; Todd J Kohn, Fishers; Ho-Shen Lin; Jefferson R McCowan, both of Indianapolis; Alan D Palkowitz, Carmel; Daniel J Sall, Greenwood; Gerald F Smith, Indianapolis; Kumiko Takeuchi, Indianapolis; Michael R Wiley, Indianapolis, all of IN (US); Minsheng Zhang, Warren, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/423,166

(22) PCT Filed: Apr. 30, 1998

(86) PCT No.: PCT/US98/08700

§ 371 Date: Jan. 21, 2000

§ 102(e) Date: Jan. 21, 2000

(87) PCT Pub. No.: WO98/48798

PCT Pub. Date: Nov. 5, 1998

(51) Int. Cl.[7] ..................... A61K 31/4025; A61K 31/41; A61K 31/5377; C07D 409/12; C07D 409/14; C07D 413/10; A61P 7/02

(52) U.S. Cl. ..................... 514/233.5; 514/324; 514/337; 514/382; 514/385; 514/397; 514/422; 514/443; 544/145; 544/146; 546/202; 546/256; 546/281.1; 548/252; 548/311.4; 548/341.5; 548/518; 548/523; 548/525; 549/51

(58) Field of Search .............................. 548/252, 311.4, 548/518, 523, 525, 341.5; 546/202, 256, 281.1; 544/145, 146; 549/51; 514/233.5, 324, 337, 382, 385, 422, 397, 443

(56) References Cited

U.S. PATENT DOCUMENTS

| 3,274,213 | 9/1966 | Lednicer . |
|---|---|---|
| 3,293,263 | 12/1966 | Lednicer . |
| 4,001,426 | 1/1977 | Brenner et al. . |
| 4,007,204 | 2/1977 | Descamps et al. . |
| 4,133,814 | 1/1979 | Jones et al. . |
| 4,418,068 | 11/1983 | Jones et al. . |
| 5,371,091 | 12/1994 | Misra et al. . |
| 5,441,965 | 8/1995 | Sall et al. . |
| 5,472,962 | 12/1995 | Koizumi et al. . |
| 5,510,357 | 4/1996 | Palkowitz . |
| 5,518,735 | 5/1996 | Sturzebecher et al. . |
| 5,523,309 | 6/1996 | Bryant et al. . |
| 5,532,254 | 7/1996 | Bowling . |
| 5,567,828 | 10/1996 | Dodge et al. . |
| 5,576,343 | 11/1996 | Nagahara et al. . |

FOREIGN PATENT DOCUMENTS

| 0 617030 | 9/1994 | (EP) . |
|---|---|---|
| WO 95/10513 | 4/1995 | (WO) . |
| WO 95/17095 | 6/1995 | (WO) . |
| WO 95/17382 | 6/1995 | (WO) . |
| WO 96/03375 | 2/1996 | (WO) . |
| WO 96/11677 | 4/1996 | (WO) . |
| WO 97/25033 | 7/1997 | (WO) . |

OTHER PUBLICATIONS

Sall, et al., "Dibasic benzo[b] thiophene derivatives as a novel class of active site–directed thrombin inhibitors. 1. Determination of the serine protease selectivity, structure–activity relationships, and binding orientation," *J. Med. Chem.*, vol. 40, No. 22, Oct. 24, 1997.

Bastian, et al., "Preparation of [(pyrrolidinoalkoxy)phenyl]–benzothiophenes and analogs as thrombin inhibitors," *Chemical Abstracts*, vol. 127, No. 3 (1997).

Robert M. Scarborough, "Chapter 8. Anticoagulant Strategies Targeting Thrombin and Factor Xa," *Annual Reports in Medicinal Chemistry*, (1995) 30, pp. 71–80.

Jones, C., et al., *J. Med. Chem.*, 22 (8), 962–966 (1979).

Jones, C., et al., *J. Med. Chem*, 27 (8), 1057–1066 (1984).

Delgado and Remens, *Textbook of Organic Medicinal and Pharmaceutical Chemistry*, 9th Edition, 30–31 (1991).

Green and Wuts, *Protective Groups in Organic Syntnesis*, 2nd Edition, 77–79 (1991).

*Primary Examiner*—Evelyn Mei Huang
(74) *Attorney, Agent, or Firm*—Arvie J. Anderson; Thomas E. Sockson

(57) ABSTRACT

This application relates to novel compounds of formula I (and their pharmaceutically acceptable salts), as defined herein, processes and intermediates for their preparation, pharmaceutical formulations comprising the novel compounds of formula I, and the use of the compounds of formula I as thrombin inhibitors.

44 Claims, No Drawings

ANTITHROMBOTIC AGENTS

This application is the national phase of PCT/US98/08700 filed on Apr. 30, 1998, which claims benefit of provisional application No. 60/045173, filed on Apr. 30, 1997.

This invention relates to thrombin inhibitors which are useful anticoagulants in mammals. In particular it relates to heterocyclic derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80.

Although the heparins and coumarins are effective anticoagulants, no commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

According to the invention there is provided a method of inhibiting thrombin comprising using an effective amount of a thrombin inhibiting compound of formula I (or a pharmaceutically acceptable salt thereof)

I wherein
A is carbonyl or methylene;
D is CH, $CR^d$ or N in which $R^d$ is formyl, hydroxymethyl, methyl or methoxy;
E is CH, $CR^e$ or N in which $R^e$ is methyl, methoxy or halo;
$R^2$ and $R^3$ are defined together such that
A. $R^2$ is $-X^2-(CH_2)_m-NR^aR^b$ in which $X^2$ is a direct bond, methylene or O; m is 1, 2, 3, 4 or 5; provided that when m is 1, then $X^2$ is a direct bond; and $R^a$ and $R^b$ are independently hydrogen or (1–3C)alkyl or the group $NR^aR^b$ is pyrrolidino, piperidino, or morpholino; and
  $R^3$ is $-CH_2-R^c$, in which $R^c$ is 5-tetrazolyl, 2-carboxy-5-oxopyrrolidin-1-yl or 2-[[(1–4C)alkoxy]carbonyl]-5-oxopyrrolidin-1-yl; or
  $R^3$ is $-O-(CH_2)_e-(CHCH_3)_f-R^f$ in which e is 0, 1, 2 or 3 and f is 0 or 1 and the sum of e and f is 1, 2 or 3 and $R^f$ is as defined below; or
B. $R^2$ is $-X^2-(CH_2)_n-R^f$ in which $X^2$ is a direct bond, methylene or O; n is 1, 2, 3 or 4; and $R^f$ is 5-tetrazolyl, carboxy, [(1–4C)alkoxy]carbonyl or hydroxymethyl; and
  $R^3$ is $-X^3-(CH_2)_s-NR^sR^t$ or $-CH_2-R^k$, in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^k$ is 2-oxopyrrolidin-1-yl or 3-(1-oxoethyl)imidazolidin-1-yl; and
one of $R^5$ and $R^6$ is hydrogen; and the other of $R^5$ and $R^6$ is hydrogen, hydroxy or methoxy.

A particular compound (or a pharmaceutically acceptable salt thereof) of formula I is one wherein
A is carbonyl or methylene;
D is CH, $CR^d$ or N in which $R^d$ is formyl, hydroxymethyl, methyl or methoxy;
E is CH, $CR^e$ or N in which $R^e$ is methyl, methoxy or halo;
$R^2$ and $R^3$ are defined together such that
A. $R^2$ is $-X^2-(CH_2)_m-NR^aR^b$ in which $X^2$ is a direct bond, methylene or O; m is 1, 2, 3, 4 or 5; provided that when m is 1, then $X^2$ is a direct bond; and $R^a$ and $R^b$ are independently hydrogen or (1–3C)alkyl or the group $NR^aR^b$ is pyrrolidino, piperidino, or morpholino; and
  $R^3$ is $-CH_2-R^c$, in which $R^c$ is 5-tetrazolyl, 2-carboxy-5-oxopyrrolidin-1-yl or 2-[[(1–4C)alkoxy]carbonyl]-5-oxopyrrolidin-1-yl; or
B. $R^2$ is $-X^2-(CH_2)_n-R^f$ in which $X^2$ is a direct bond, methylene or O; n is 1, 2 or 3; and $R^f$ is 5-tetrazolyl, carboxy, [(1–4C)alkoxy]carbonyl or hydroxymethyl; and
  $R^3$ is $-X^3-(CH_2)_s-NR^sR^t$ or $-CH_2-R^k$, in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^k$ is 2-oxopyrrolidin-1-yl or 3-(1-oxoethyl)imidazolidin-1-yl;

$R^5$ is hydrogen; and $R^6$ is hydrogen, hydroxy or methoxy.

A particular value for D is CH.

A particular value for E is CH or $CR^e$ in which $R^e$ is methoxy.

A particular set of values when $R^3$ is —$CH_2$—$R^c$ is: $R^c$ is 5-tetrazolyl, 2-carboxy-5-oxopyrrolidin-1-yl or 2-(ethoxycarbonyl)-5-oxopyrrolidin-1-yl; and $R^2$ is 2-pyrrolidinoethoxy.

A particular set of values when $R^2$ is —$X^2$—$(CH_2)_n$—$R^f$ is: A is methylene, $X^2$ is O; n is 1 or 3; and $R^f$ is carboxy, [(1–4C)alkoxy]carbonyl in which (1–4C)alkoxy is methoxy, ethoxy or t-butoxy, or hydroxymethyl.

A particular set of values when $R^3$ is —$X^3$—$(CH_2)_s$—$NR^sR^t$ is: E is $CR^e$ in which $R^e$ is methoxy and $R^3$ is pyrrolidinomethyl.

A particular value for $R^5$ is methoxy.

A particular value for $R^6$ is hydroxy.

A more particular value for A is methylene.

The present invention also provides a method of inhibiting coagulation in a mammal comprising administering to a mammal in need of treatment, a coagulation inhibiting dose of a thrombin inhibiting compound of formula I having any of the above definitions.

The present invention further provides a method of inhibiting thrombin comprising administering to a mammal in need of treatment, a thrombin inhibiting dose of a thrombin inhibiting compound of formula I having any of the above definitions.

Further, the present invention provides a method of treating a thromboembolic disorder comprising administering to a mammal in need of treatment, an effective dose of a thrombin inhibiting compound of formula I having any of the above definitions.

In addition, there is provided the use of a thrombin inhibiting compound of formula I having any of the above definitions for the manufacture of a medicament for treatment of a thromboembolic disorders.

As a further aspect of the invention, there is provided a prodrug (or a pharmaceutically acceptable salt thereof) of any of the above described thrombin inhibiting compounds of formula I which will form a prodrug. (It will be recognized that a thrombin inhibiting compound of formula I also may serve as a prodrug for a different thrombin inhibiting compound of formula I).

As an additional feature of the invention there is provided a pharmaceutical formulation comprising in association with a pharmaceutically acceptable carrier, diluent or excipient, a prodrug of a thrombin inhibiting compound of formula I (or of a pharmaceutically acceptable salt thereof) as provided in any of the above descriptions.

A compound of formula I in which $R^f$ is an ester or hydroxymethyl group may act directly as a thrombin inhibitor or indirectly as a result of its biotransformation to a corresponding compound of formula I in which $R^f$ is carboxy.

In general, the thrombin inhibiting compounds of formula I are believed to be novel and, thus, to constitute an additional aspect of the invention. Thus, according to the invention there is provided a novel compound of formula I (or a pharmaceutically acceptable salt thereof) according to any of the above definitions of a compound of formula I, provided that the compound is not one which is not novel. A pharmaceutically acceptable salt of an antithrombotic agent of the instant invention includes one which is an acid-addition salt made with an acid which provides a pharmaceutically acceptable anion. Thus, an acid addition salt of a novel compound of formula I as provided above made with an acid which affords a pharmaceutically acceptable anion provides a particular aspect of the invention. Examples of such acids are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the above descriptions.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) may exist in, and be isolated in, isomeric forms, including cis- or trans-isomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–3C)alkyl group is, for example, methyl, ethyl, propyl or isopropyl, and for a (1–4C)alkoxy group is, for example, methoxy, ethoxy, isopropoxy or t-butoxy.

A compound of formula I may be made by processes which include processes known in the chemical art for the production of known compounds of formula I or of structurally analogous compounds or by a novel process described herein. A process for a novel compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

In general, a compound of formula I may be prepared according to one of the routes outlined in Scheme I for a compound of formula I in which $R^5$ is hydrogen, and which are described in the examples, in which each of $Q^2$, $Q^3$ and $Q^6$, respectively, represents a value defined for the groups $R^2$, $R^3$ and $R^6$, a protected version of such a group, or moiety which can be further elaborated into such a group. Final conversion of a group $Q^2$, $Q^3$ or $Q^6$ into $R^2$, $R^3$ or $R^6$ is carried out at a convenient point, consistent with the chemistry employed. It will be recognized that a number of other routes may be used, particularly those involving condensation of an organometallic species to form a compound of formula C or G in Scheme I, as well as the fact that for a compound in which $R^5$ is not hydrogen, the corresponding scheme with compounds bearing a group $Q^5$ at the 5-position and in which $Q^6$ is hydrogen is appropriate.

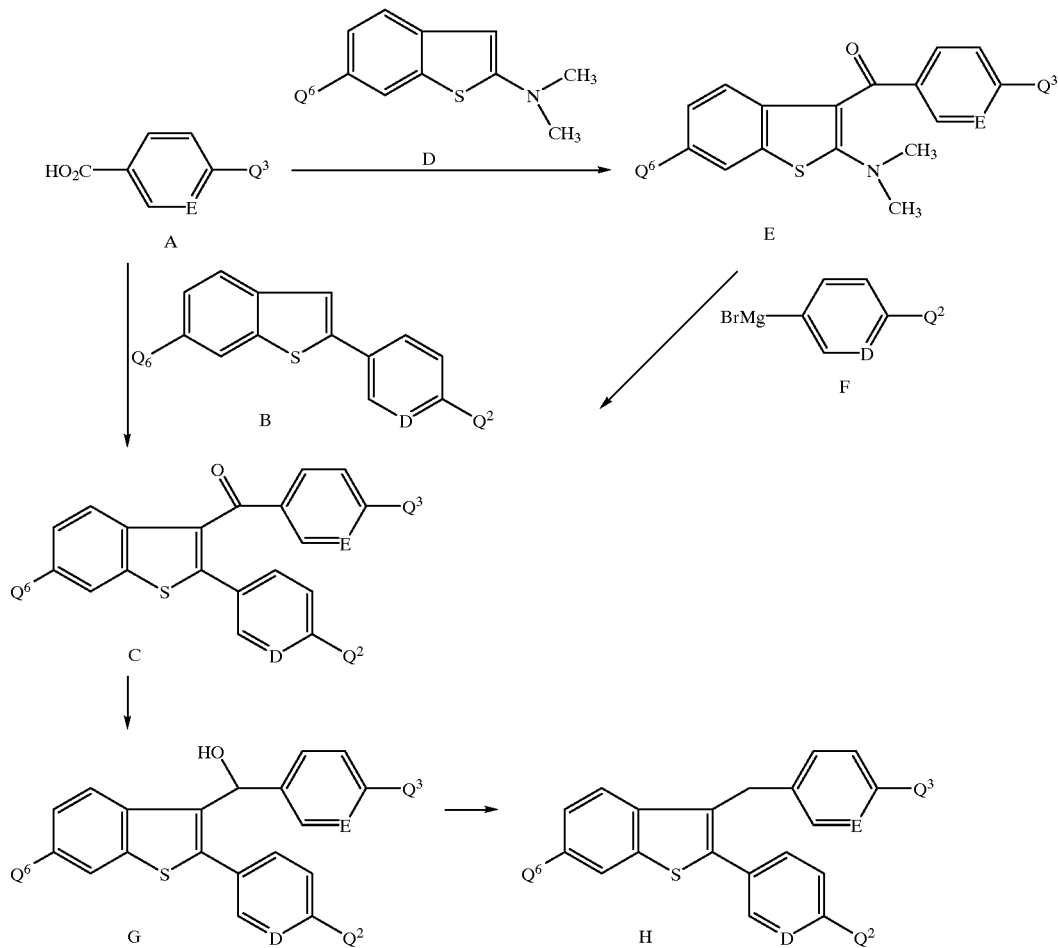

Thus, there is provided a process for preparing a novel compound of formula I (or a pharmaceutically acceptable salt thereof) as provided in any of the above descriptions which is selected from any of those described in the examples, including, (a-1) for a compound of formula I in which $R^2$ is $-X^2-(CH_2)_m-NR^aR^b$ or $-X^2-(CH_2)_n-R^f$ in which $X^2$ is O, alkylating the hydroxy group of a corresponding phenol of formula II;

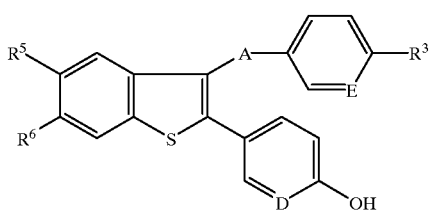

with a group of formula $X-(CH_2)_m-NR^aR^b$ or $X-(CH_2)_n-R^f$, respectively, or a protected derivative thereof, wherein X is a conventional leaving group;

(a-2) for a compound of formula I in which $R^3$ is $-O-(CH_2)_e-(CHCH_3)_f-R^f$ or $-X^3-(CH_2)_s-NR^sR^t$ in which $X^3$ is O, alkylating the hydroxy group of a corresponding phenol of formula III;

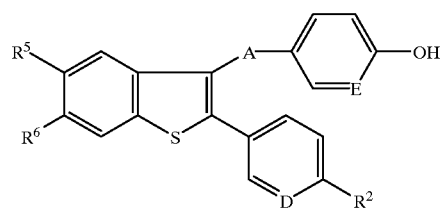

with a group of formula $X-(CH_2)_e-(CHCH_3)_f-R^f$ or $X-(CH_2)_s-NR^sR^t$, respectively, or a protected derivative thereof, wherein X is a conventional leaving group;

(b) for a compound of formula I in which $R^c$ is 2-carboxy-5-oxopyrrolidin-1-yl or $R^f$ is carboxy, decomposing the ester of a corresponding compound of formula I in which $R^c$ is 2-[[(1–4C)alkoxy]carbonyl]-5-oxopyrrolidin-1-yl or $R^f$ is [(1–4C)alkoxy]carbonyl, respectively;

(c) for a compound of formula I in which $R^f$ is hydroxymethyl, reducing the acid or the ester of a corresponding compound of formula I in which $R^f$ is carboxy or [(1–4C)alkoxy]carbonyl, respectively;

(d) for a compound of formula I in which $R^3$ is $-CH_2-R^c$ in which $R^c$ is 2-[[(1–4C)alkoxy]carbonyl]-5-oxopyrrolidin-1-yl, or $R^3$ is $CH_2-NR^sR^t$, or $R^3$ is —CH$_2$—R$^k$, alkylating the nitrogen of a corresponding amine of formula H—R$^c$, H—NR$^s$R$^t$ or H—R$^k$, respectively, using a bromide corresponding to the compound of formula I, but in which R$^3$ is —CH$_2$—X, wherein X is a conventional leaving group;

(e) for a compound of formula I in which R$^f$ is carboxy, hydrolysis of the cyano group of a corresponding compound but in which R$^f$ is cyano;

(f) for a compound of formula I in which A is methylene, reductive removal of the hydroxy group of a corresponding compound but in which A is —CH(OH)—;

(g) for a compound of formula I in which R$^2$ is —X$^2$—(CH$_2$)$_m$—NR$^a$R$^b$, alkylating the nitrogen of a corresponding amine of formula H—NR$^a$R$^b$, using a compound corresponding to the compound of formula I, but in which R$^2$ is —X$^2$—(CH$_2$)$_m$—X in which X is a conventional leaving group;

(h) for a compound of formula I in which A is carbonyl, condensation of a reagent of formula IV

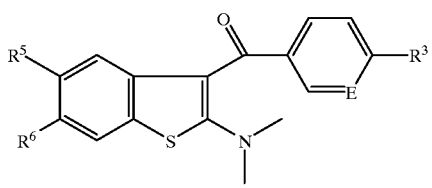

IV with a Gringard reagent of formula V

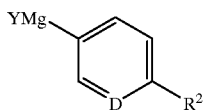

V (or a protected derivative thereof) wherein Y is chloro, bromo or iodo;

(i) for a compound of formula I in which R$^f$ is 5-tetrazolyl, cycloaddition of a corresponding compound but in which R$^f$ is cyano with an azide reagent;

(j) for a compound of formula I in which A is carbonyl, acylation of a compound of formula VI

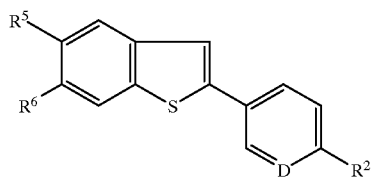

VI with a Friedel-Crafts reagent derived from an acid of formula VII

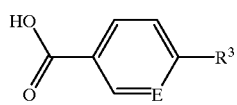

VII or from the corresponding nitrile;

(k) for a compound of formula I in which R$^2$ is —X$^2$—(CH$_2$)$_n$—R$^f$ in which X$^2$ is a direct bond and n is 2, reducing the double bond of a corresponding compound but in which R$^2$ is —CH=CH—R$^f$;

whereafter, for any of the above procedures, when a functional group is protected using a protecting group, removing the protecting group;

whereafter, for any of the above procedures, when a pharmaceutically acceptable salt of a compound of formula I is required, it may be obtained by reacting the basic form of such a compound of formula I with an acid affording a physiologically acceptable counterion, or, for a compound of formula I which bears an acidic moiety, reacting the acidic form of such a compound of formula I with a base which affords a pharmaceutically acceptable cation, or by any other conventional procedure.

As used herein, a leaving group is a moiety which is displaced in a nucleophilic substitution reaction, for example a halo group (such as chloro, bromo or iodo), a sulfonate ester group (such as methylsulfonyloxy, p-toluylsulfonyloxy or trifluoromethylsulfonyloxy), or the reactive species derived from treating an alcohol with triphenylphospine, diethyl azodicarboxylate and triethyl amine (in a Mitsunobu reaction).

Novel intermediate or starting material compounds, such as a novel phenol of formula II or formula III provide a further aspect of the invention.

As mentioned above, a compound corresponding to a compound of formula I but in which a functional group is protected may serve as an intermediate for a compound of formula I. Accordingly, such protected intermediates for a novel compound of formula I provide further aspects of the invention. Thus, as one particular aspect of the invention, there is provided a compound corresponding to a novel compound of formula I as defined above in which R$^6$ which is hydroxy, but in which the corresponding substituent is —OR$^p$ in place of hydroxy, wherein R$^p$ is a phenol protecting group other than methyl. Phenol protecting groups are well known in the art, for example as described in T. W. Greene and P. G. M. Wuts, "Protecting Groups in Organic Synthesis" (1991). Particular values of R$^p$ include, for example, benzyl and allyl. Further, R$^p$ may denote a functionalized resin, for example as disclosed in H. V. Meyers, et al., *Molecular Diversity*, (1995), 1, 13–20.

As mentioned above, the invention includes pharmaceutically acceptable salts of the thrombin inhibiting compounds defined by the above formula I. A compound of formula I which bears an acidic moiety forms salts with pharmaceutically acceptable bases. Such a pharmaceutically acceptable salt may be made with a base which affords a pharmaceutically acceptable cation, which includes alkalai metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine. The potassium and sodium salt forms are particularly preferred.

A particular compound of of formula I which possesses one or more sufficiently basic functional groups to react with any of a number of inorganic and organic acids affording a physiologically acceptable counterion forms a pharmaceutically acceptable acid addition salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of protection and deprotection are well known in the art for preparation of compounds such as those corresponding to a compond of formula I but in which $R^b$ is $OR^p$ discussed above. Selective methods for cleavage of methyl ethers, as described in the examples, are discussed in Jones, et al., *J. Med. Chem.*, (1984), 27, 1057–1066. For example, the diether 3-(4-methoxybenzoyl)-2-(4-methoxyphenyl)benzo[b]thiophene may be treated with boron tribromide in dichloromethane at −10° C. (1 hour) to afford the monoether 2-(4-hydroxyphenyl)-3-(4-methoxybenzoyl)benzo[b]thiophene, whereas treatment with sodium thioethoxide affords the isomeric monoether 3-(4-hydroxybenzoyl)-2-(4-methoxyphenyl)benzo[b]thiophene. Treatment with boron tribromide under less mild conditions (0° C., 6 hours) or with aluminum chloride and ethanethiol cleaves both ethers.

Generally, the compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (so).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|                                      | Weight |
|--------------------------------------|--------|
| Active ingredient                    | 0.25   |
| Ethanol                              | 25.75  |
| Propellant 22 (Chlorodifluoromethane) | 70.00  |
| Total                                | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

|                                      |         |
|--------------------------------------|---------|
| Active ingredient                    | 60 mg   |
| Starch                               | 45 mg   |
| Microcrystalline cellulose           | 35 mg   |
| Polyvinylpyrrolidone (as 10% solution in water) | 4 mg |
| Sodium carboxymethyl starch          | 4.5 mg  |
| Magnesium stearate                   | 0.5 mg  |
| Talc                                 | 1 mg    |
| Total                                | 150 mg  |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

|                              |        |
|------------------------------|--------|
| Active ingredient            | 80 mg  |
| Starch                       | 59 mg  |
| Microcrystalline cellulose   | 59 mg  |
| Magnesium stearate           | 2 mg   |
| Total                        | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

|                                |           |
|--------------------------------|-----------|
| Active ingredient              | 225 mg    |
| Saturated fatty acid glycerides| 2,000 mg  |
| Total                          | 2,225 mg  |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

|                                 |          |
|---------------------------------|----------|
| Active ingredient               | 50 mg    |
| Sodium carboxymethyl cellulose  | 50 mg    |
| Syrup                           | 1.25 mL  |
| Benzoic acid solution           | 0.10 mL  |
| Flavor                          | q.v.     |
| Color                           | q.v.     |
| Purified water to total         | 5 mL     |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

|                     |           |
|---------------------|-----------|
| Active ingredient   | 100 mg    |
| Isotonic saline     | 1,000 mL  |

The solution of the above ingredients generally is administered intravenously to a subject at a rate of 1 mL per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 $\mu$L buffer (0.03M Tris, 0.15M NaCl, pH 7.4) with 25 $\mu$L of human thrombin solution (purified human thrombin, Enzyme Research Laboratories, South Bend, Indiana, at 8 NIH units/mL) and 25 $\mu$L of test compound in a solvent (50% aqueous methanol (v:v)). Then 150 $\mu$L of an aqueous solution of the chromogenic substate (at 0.25 mg/mL) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$Thrombin + I \rightleftharpoons Thrombin-I$$

$$Kass = \frac{[Thrombin\text{-}I]}{[(Thrombin) \times (I)]}$$

Kass is calculated for a range of concentrations of test compounds and the mean value reported in units of liter per mole. In general, a thrombin inhibiting compound of formula I of the instant invention exhibits a Kass of $0.05 \times 10^6$ L/mole or much greater.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilde (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/ plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 μL thrombin (73 NIH unit/mL) to 100 μL human plasma which contains 0.0229 μCi 125-iodine labeled fibrinogen. Clot lysis is studied by overlaying the clots with 50 μL of urokinase or streptokinase (50, 100, or 1000 unit/mL) and incubating for 20 hours at room temperature. After incubation the tubes are centrifuged in a Beckman Microfuge. 25 μL of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 μg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, Br J Pharmacol, 77:29, 1982). In this model preferred compounds of the instant invention reduce the net clot weight to approximately 25–30% of control, or even lower, at an i.v. dose of 33.176 μmol/kg/h.

FeCl$_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, Thromb. Res., 60:269, 1990).

Spontaneous Thrombolysis Model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}$I human Fibrogen (5 μCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, Cardiovas. Pharmacol., 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\, po}{AUC\, iv} \times \frac{Dose\, iv}{Dose\, po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means+/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months—2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libi tum. The room temperature is maintained between 66–74° F.; 45–50 percent relative humidity; and lighted from 0600–1800 hours.

Pharmacokinetic Model.

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for [3] 30 minutes.

Hematology and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl

AIBN=azobisisobutyronitrile

Anal.=elemental analysis

Bn or Bzl=benzyl

Bu=butyl n-BuLi=butyllithium calcd=calculated

DCC=dicyclohexylcarbodiimide

DIBAL-H=diisobutyl aluminum hydride

DMF=dimethylformamide

DMSO=dimethylsulfoxide

Et=ethyl

EtOAc=ethyl acetate

Et$_3$N=triethylamine

Et$_2$O=diethyl ether

EtOH=ethanol

EtSH=ethanethiol

FAB=Fast Atom Bombardment (Mass Spectroscopy)

FDMS=field desorption mass spectrum

Hex=hexanes

HOAt=1-hydroxy-7-azabenzotriazole

HPLC=High Performance Liquid Chromatography

HRMS=high resolution mass spectrum i-PrOH=isopropanol

IR=Infrared Spectrum
LAH=lithium aluminum hydride
Me=methyl
MeI=methyl iodide
MeOH=methanol
MPLC=Medium Pressure Liquid Chromatography
NBS=N-bromosuccinimide
NMR=Nuclear Magnetic Resonance
Ph=phenyl
PPA=polyphosphoric acid
i-Pr=isopropyl
Rochelle's Salt=potassium sodium tartrate
RPHPLC=Reversed Phase High Performance Liquid Chromatography
$SiO_2$=silica gel
SM=starting material
TBS=tert-butyldimethylsilyl
TEA=triethylamine
Temp.=temperature
TFA=trifluoroacetic acid
THF=tetrahydrofuran
TIPS=triisopropylsilyl
TLC=thin layer chromatography
triflic acid=trifluoromethanesulfonic acid Unless otherwise stated, pH adjustments and work up are with aqueous acid or base solutions. PrepLC indicates preparative liquid chromatography using "Prep Pak (™)" silica cartridges; radial chromatography indicates preparative chromatography using a "Chromatotron (™)" instrument.

EXAMPLE 1

Preparation of 2-[4-[4-Methoxy-4-oxobutoxy]phenyl]-3-[4-(1-pyrrolidinylmethyl)benzyl]benzo[b]thiophene

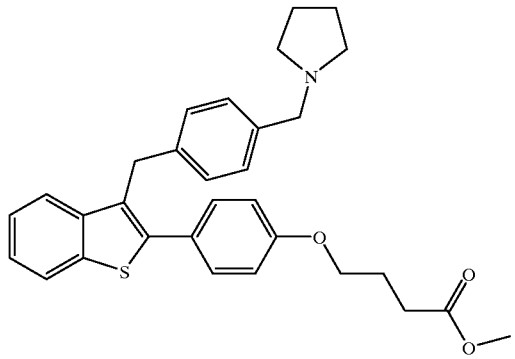

A. Methyl 4-(1-Pyrrolidinylmethyl)benzoate.

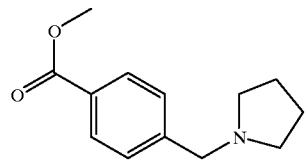

Methyl 4-bromomethylbenzoate (5.43 g; 23.7 mmol) was dissolved in 50 mL of THF. Pyrrolidine (5.0 mL; 2.5 eq) was added, and the resultant mixture stirred at room temperature for 2 h. Water was added and extraction carried out with EtOAc (4×50 mL). The combined organics were dried by passage through $Na_2SO_4$. The title compound was isolated by flash chromatography on silica gel, eluting with EtOAc, as a colorless liquid (4.77 g; 92%).

$^1$H NMR (CDCl$_3$) δ 8.02 (d, J=7.7 Hz, 2H), 7.43 (d, J=7.7 Hz, 2H), 3.93 (s, 3H), 3.70 (s, 2H), 2.51 (br s, 4H), 1.80 (br s, 4H). FDMS 219.2 (M).

B. 4-(2-Benzo[b]thiophenyl)phenyl Triisopropylsilyl Ether.

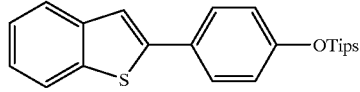

In a flame-dried, argon-filled flask were combined 1.36 g (6.0 mmol) of 2-(4-hydroxyphenyl)benzo[b]thiophene and 1.68 mL (12.0 mmol) of $Et_3N$ in 10 mL of DMF. After cooling in an ice-water bath, 3.23 g (12.0 mmol) of triisopropylsilyl trifluorosulfonate was added. The bath was removed, and stirring continued for 1 h while warming to room temperature. The mixture was concentrated under reduced pressure, and the title compound was isolated as a white crystalline solid (2.05 g; 89% yield) by flash chromatography on silica gel, eluting with hexanes(95%)/EtOAc (5%).

Anal. calc'd for $C_{23}H_{30}OS$: C, 72.19; H, 7.90. Found: C, 72.22; H, 7.91. FDMS 382.1 (M).

C. 2-(4-Triisopropylsilyloxyphenyl)benzo[b]thiophen-3-yl 4-(1-Pyrrolidinylmethyl)phenyl Ketone.

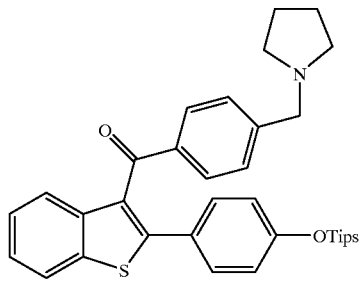

Methyl 4-(1-pyrrolidinylmethyl)benzoate (2.0 g; 9.12 mmol) was dissolved in 20 mL of a mixture of THF/MeOH/$H_2O$ (3:1:1). LiOH (0.46 g; 1.2 eq) was added, and the resultant mixture stirred at room temperature for 3 days. The mixture was neutralized with conc HCl, and the solvent removed under reduced pressure. The crude 4-(1-pyrrolidinylmethyl)benzoic acid hydrochloride was dried in vacuo for 2 h, and used without purification.

4-(1-Pyrrolidinylmethyl)benzoic acid hydrochloride was dissolved in 15 mL of $SOCl_2$ with 3 drops of DMF and heated under reflux for 2 h. After cooling, the excess $SOCl_2$ was removed under reduced pressure. The crude 4-(1-pyrrolidinylmethyl)benzoyl chloride hydrochloride was dried in vacuo overnight and used without purification.

4-(2-Benzo[b]thiophenyl)phenyl triisopropylsilyl ether (part B) was dissolved in 1,2-dichloroethane (15 mL) in a flame-dried, argon-filled flask and cooled in an ice-water bath. 4-(1-Pyrrolidinylmethyl)benzoyl chloride hydrochloride (0.44 g; 1.5 eq) was added. The flask was covered with foil to minimize light exposure, and $TiCl_4$ (0.48 mL; 4.0 eq) was added. The mixture was stirred overnight, then poured into saturated $NaHCO_3$ (60 mL). Extraction was carried out with EtOAc (4×50 mL), and the combined organics were washed with brine and dried by passage through Na$_2$SO$_4$. The title compound was isolated (0.22 g; 35% yield overall) as a viscous yellow oil by flash chromatography on silica gel, eluting with EtOAc.

$^1$H NMR (CDCl$_3$) δ 7.87 (m, 1H), 7.73 (m, 1H), 7.71 (d, J=8.1 Hz, 2H), 7.37 (m, 2H), 7.27 (m, 4H), 6.71 (d, J=6.8 Hz, 2H), 3.56 (s, 2H), 2.45 (br s, 4H), 1.77 (br s, 4H), 1.20 (m, 3H), 1.03 (d, J=7.0 Hz, 18H).

D. 2-(4-Hydroxyphenyl)-3-[4-(1-pyrrolidinylmethyl) benzyl]benzo[b]thiophene.

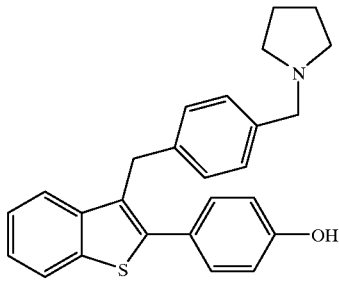

To the above silyl ether (part C) (0.22 g; 0.39 mmol) in 5.0 mL of THF was added 15 mg (0.39 mmol) of LAH at 0° C. The bath was removed and the mixture was stirred for 1 h. Hydrolysis was effected by addition of 1 drop of water, 1 drop of 5 N NaOH, and 3 drops of water, followed by stirring for 1 h. The mixture was filtered and washed thoroughly with THF, the filtrate was concentrated and the intermediate carbinol was dried in vacuo for 25 min. The carbinol was dissolved in methylene chloride (5.0 mL) under argon atmosphere and cooled in an ice-water bath. Triethylsilane (0.43 mL; 2.70 mmol) was added, followed by dropwise addition of 0.30 mL (3.86 mmol) of TFA. Upon completion of addition of TFA, the bath was removed and stirring was continued for 2 h. Saturated aqueous sodium bicarbonate (25 mL) was added, and extraction was carried out with EtOAc. The combined organics were washed with brine and dried by passage through sodium sulfate. Removal of the protecting group was effected by treatment of the Tips derivative with 1.0 mL of TBAF (1 M in THF) in 3.0 mL of THF for 1 h. After concentration under reduced pressure, the title compound (66 mg; 66% yield) was isolated by flash chromatography on silica gel, eluting with a gradient of EtOAc(100–90%)/-Et$_3$N(0–5%)/MeOH(0–5%).

$^1$H NMR (CDCl$_3$) δ 7.80 (d, J=8.1 Hz, 1H), 7.44 (d, J=8.1 Hz, 1H), 7.4–7.2 (m, 6H), 7.06 (d, J=6.8 Hz, 2H), 6.76 (d, J=6.8 Hz, 2H), 4.22 (s, 2H), 3.69 (s, 2H), 2.67 (br s, 4H), 1.86 (br s, 4H). FDMS 400 (M+1).

E. 2-[4-[4-Methoxy-4-oxobutoxy]phenyl]-3-[4-(1-pyrrolidinylmethyl)benzyl]benzo[b]thiophene.

In an argon-filled flask were combined 66 mg (0.17 mmol) of the above phenol (Part D), Cs$_2$CO$_3$ (0.38 g; 7 eq), and methyl 4-chlorobutyrate (24 μL; 1.2 eq) in 2.0 mL of DMF. The resulting mixture was immersed in an oil bath maintained at 75° C. for 2.5 h. After cooling, 25 mL of water was added, and extraction was carried out with EtOAc (4×25 mL). The combined organics were washed with brine and dried by passage through Na$_2$SO$_4$. The title compound (52 mg; 63% yield) was isolated by flash chromatography on silica gel, eluting with a gradient of EtOAc(100–90%)/Et$_3$N (0–5%)/MeOH(0–5%).

$^1$H NMR (CDCl$_3$) δ 7.86 (d, J=8.7, 1H), 7.52 (d, J=8.6, 1H) 7.44 (d, J=8.7, 2H), 7.30 (m, 2), 7.24 (d, J=8.1, 2H), 7.12 (d, J=7.9, 2H), 6.94 (d, J=8.6, 2H), 4.27 (s, 2H), 4.04 (t, J=6.0, 2H), 3.72 (s, 3), 3.59 (s, 2H), 2.55 (m, 6), 2.15 (m, 2H), 1.78 (m, 4H). FDMS 499.2 (M).

EXAMPLE 2

Preparation of 2-[4-[4-Hydroxy-4-oxobutoxy] phenyl]-3-[4-(1-pyrrolidinylmethyl)benzyl]benzo[b] thiophene Lithium Salt

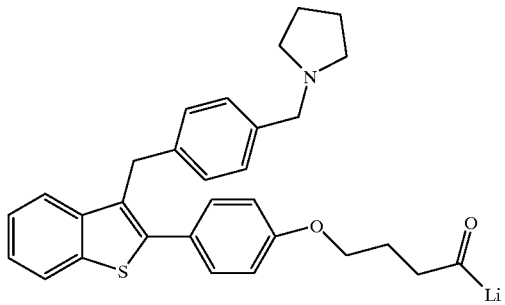

The ester of Example 1, Part E (47 mg; 94 μmol) was dissolved in 2 mL of a mixture of THF/MeOH/H$_2$O (3:1:1) in an argon atmosphere and 5 mg of LiOH (1.2 eq) was added. The resulting mixture was stirred overnight then concentrated under reduced pressure and dried in vacuo.

EXAMPLE 3

Preparation of 2-[4-[4-Methoxy-4-oxobutoxy] phenyl]-3-[3-methoxy-4-(1-pyrrolidinylmethyl) benzyl]benzo[b]thiophene

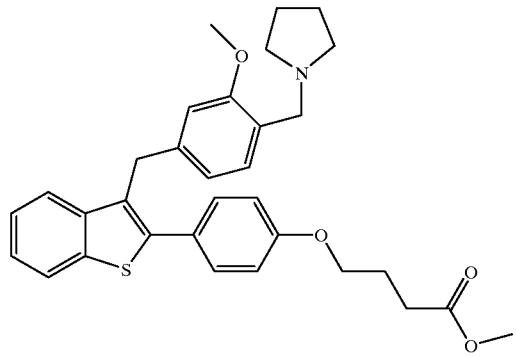

A. Methyl 4-Bromomethyl-3-methoxybenzoate.

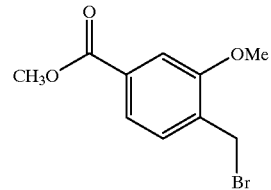

Methyl 3-methoxy-4-methylbenzoate (9.95 g; 55.2 mmol) and 10.81 g (60.7 mmol) of NBS were combined in 250 mL of CCl$_4$ and heated to reflux. AIBN (0.75 g; 5.5 mmol) was added, and the resultant mixture was heated at reflux for 8 h. The mixture was refrigerated, then filtered and concentrated under reduced pressure. The residue was triturated with hexanes and filtered to give the title compound as white needles (11.7 g; 82% yield).

$^1$H NMR (CDCl$_3$) δ 7.63 (d, J=7.6 Hz, 1H), 7.58 (s, 1H), 7.41 (d, J=7.9 Hz, 1H), 4.56 (s, 2H), 3.98 (s, 3H), 3.94 (s, 3H); FDMS 528 (M+).

B. Methyl 3-Methoxy-4-(1-pyrrolidinylmethyl)benzoate.

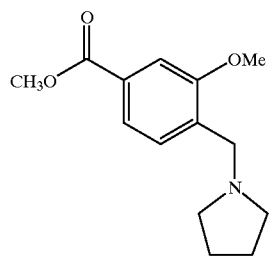

Methyl 4-bromomethyl-3-methoxybenzoate (1.0 g; 3.9 mmol) (Part A) was dissolved in THF (10 mL) and pyrrolidine (1.3 mL; 15.4 mmol) was added at room temperature. The mixture was stirred overnight at room temperature, then poured into 50 mL of water. Extraction was carried out with EtOAc (4×25 mL). The combined organics were washed with brine and dried by passage through sodium sulfate. The title compound was isolated (0.92 g; 96% yield) by flash chromatography on silica gel, eluting with EtOAc (100–95%)/Et$_3$N(0–5%).

$^1$H NMR (CDCl$_3$) δ 7.62 (d, J=7.8 Hz, 1H), 7.51 (s, 1H), 7.43 (d, J=7.7 Hz, 1H), 3.90 (s, 3H), 3.87 (s, 3H), 3.69 (s, 2H), 2.57 (m, 4H), 1.79 (m, 4H).

C. 2-(4-Triisopropylsilyloxyphenyl)benzo[b]thiophen-3-yl 3-Methoxy-4-(1-pyrrolidinylmethyl)phenyl Ketone.

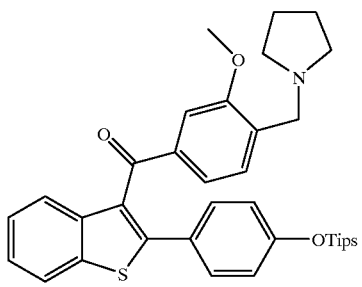

Essentially following the procedure of Example 1, Part C, the title compound was prepared from 4-(2-benzo[b]thiophenyl)phenyl triisopropylsilyl ether (Example 1, Part B) and methyl 3-methoxy-4-(1-pyrrolidinylmethyl)benzoate (Part C) in 39% yield. Purification was accomplished by flash chromatography on silica gel, eluting with a gradient of EtOAc(100–95%)/Et$_3$N(0–5%).

$^1$H NMR (CDCl$_3$) δ 7.91 (m, 1H), 7.78 (m, 1H), 7.41 (m, 3H), 7.31 (m, 4), 6.75 (d, J=6.7, 2H), 3.81 (s, 3H), 3.63 (s, 2H), 2.54 (br s, 4H), 1.79 (br s, 4H), 1.22 (m, 3H), 1.08 (d, J=7.0, 18).

D. 2-(4-Hydroxyphenyl)-3-[3-methoxy-4-(1-pyrrolidinylmethyl)benzyl]benzo[b]thiophene.

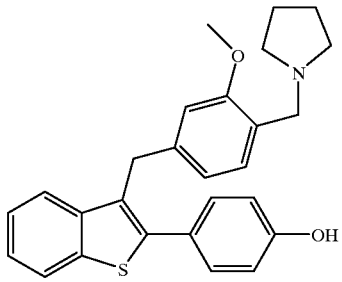

To the above silyl ether (part C) (0.22 g; 0.37 mmol) in 3.0 mL of THF was added 40 mg (0.37 mmol) of LAH at 0° C. The bath was removed and the mixture was stirred for 1 h. Hydrolysis was effected by addition of 1 drop of water, 1 drop of 5 N NaOH, and 3 drops of water, followed by stirring for 1 h. The mixture was filtered and washed thoroughly with THF, the filtrate was concentrated, and the intermediate carbinol was dried in vacuo for 25 min. Removal of the TIPS protecting group was effected by treatment with 1.0 mL of TBAF (1M in THF) in 3.0 mL of THF for 1 h. The carbinol was then dissolved in methylene chloride (3.0 mL) under argon atmosphere and cooled in an ice-water bath. Triethylsilane (0.41 mL; 2.57 mmol) was added, followed by dropwise addition of 0.28 mL (3.67 mmol) of TFA. Upon completion of addition of TFA, the bath was removed and stirring was continued for 2 h. Saturated aqueous sodium bicarbonate (25 mL) was added, and extraction was carried out with EtOAc. The combined organics were washed with brine and dried by passage through sodium sulfate. After concentration under reduced pressure the title compound (66 mg; 66% yield) was isolated by flash chromatography on silica gel eluting with a gradient of EtOAc(100–90%)/Et$_3$N(0–5%)/MeOH(0–5%).

$^1$H NMR (CDCl$_3$) δ 7.85 (m, 1H), 7.56 (m, 1H), 7.32 (m, 4H), 7.19 (d, J=7.6, 1H), 6.73 (m, 3H), 6.63 (s, 1H), 4.26 (s, 2H), 3.73 (s, 2H), 3.58 (s, 3H), 2.69 (br s, 4H), 1.85 (br s, 4H). FDMS 430 (M+1).

E. 2-[4-[4-Methoxy-4-oxobutoxy]phenyl]-3-[3-methoxy-4-(1-pyrrolidinylmethyl)benzyl]benzo[b]thiophene.

By following essentially the procedure of Example 1-E, the title compound was prepared from the above phenol (Part D) and methyl 4-chlorobutyrate in 85% yield. Purification was effected by flash chromatography on silica gel, eluting with a gradient of EtOAc(100–94%)/Et$_3$N(0–5%)/MeOH(0–2%).

$^1$H NMR (CDCl$_3$) δ 7.88 (d, J=8.5 Hz, 1H), 7.58 (d, J=8.9 Hz, 1H), 7.48 (d, J=8.6 Hz, 2H), 7.35–7.30 (m, 2), 7.23 (d, J=7.6 Hz, 1H), 6.96 (d, J=8.6 Hz, 2H), 6.74 (d, J=7.9 Hz, 1H), 6.71 (s, 1H), 4.29 (s, 2H), 4.08 (t, J=6.1 Hz, 2H), 3.74 (s, 6H), 3.65 (s, 2H), 2.59 (m, 6H), 2.18 (m, 2H), 1.82 (br s, 4H). FDMS 529.3 (M).

EXAMPLE 4

Preparation of 2-[4-[4-Hydroxy-4-oxobutoxylphenyl]-3-[3-methoxy-4-(1-pyrrolidinylmethyl)benzyl]benzo[b]thiophene

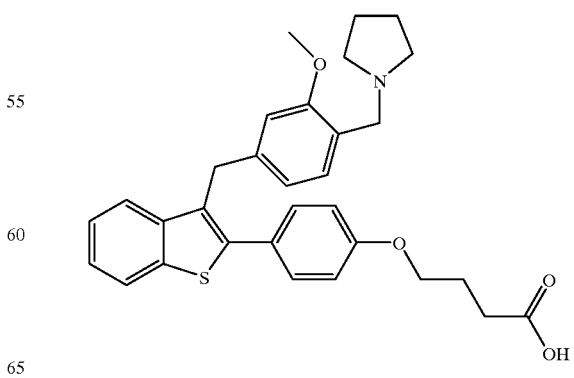

The ester of Example 3 (24 mg; 45 μmol) was combined with 2.0 mL of 3 M HCl and heated in an oil bath maintained at 90° C. overnight. The mixture was concentrated under reduced pressure and dried in vacuo to give 23 mg (92% yield) of the title compound.

$^1$H NMR (DMSO-d$_6$) δ 10.05 (br s, 1H), 7.98 (m, 1H), 7.66 (m, 1H), 7.48 (d, J=8.5, 2H), 7.35 (m, 3H), 7.07 (d, J=8.6, 2H), 6.94 (s, 1H), 6.65 (d, J=7.8, 1H), 4.30 (s, 2H), 4.20 (d, J=5.14, 2H), 4.05 (t, J=6.4, 2H), 3.76 (s, 3H), 3.35 (br s, 2H), 3.03 (br s, 2H), 2.41 (t, J=7.4, 2H), 2.0–1.8 (m, 6H). FDMS 516 (M for free base).

EXAMPLE 5

Preparation of 2-[4-[4-Hydroxy-4-oxobutoxy]phenyl]-3-[3-methoxy-4-(2-oxopyrrolidin-1-ylmethyl)benzyl]benzo[b]thiophene

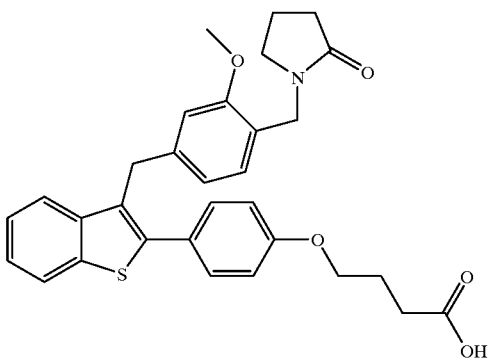

The ester of Example 3 (45 mg; 85 μmol) was dissolved in 0.5 mL of CH$_2$Cl$_2$ and 9 mg (1 eq) of BrCN was added. After stirring for 5 min at room temperature, 25 mL of EtOAc was added. The organics were washed with saturated Na$_2$CO$_3$, and dried by passage through Na$_2$SO$_4$. The mixture was concentrated under reduced pressure, placed under high vacuum for 1 h and dissolved in 1 mL of THF. In a separate argon-filled flask, 6 mg of NaH (60% in mineral oil) was suspended in anhydrous THF. After stirring for 10 min, 2-pyrrolidinone (32 μL; 0.42 mmol) was added, and stirring was continued for 0.5 h. The THF solution of the benzothiophene prepared above was added and the mixture immersed in an oil bath maintained at 70° C. for 1 h, then stirred while cooling to room temperature overnight. EtOAc (70 mL) was added, and the resulting solution washed with saturated NaHCO$_3$. No product was found in the organic layer. The aqueous portion was acidified with conc HCl and extracted with EtOAc (3×80 mL). The combined organics were washed with brine and dried by passage through Na$_2$SO$_4$. The title compound (10 mg; 22% yield) was isolated by flash chromatography on silica gel, eluting with a gradient of EtOAc(100–98%)/HOAc(0–2%).

$^1$H NMR (CDCl$_3$) δ 7.88 (m, 1H), 7.59 (m, 1H), 7.44 (d, J=8.6, 2H), 7.35 (m, 2H), 7.04 (d, J=7.4, 1H), 6.95 (d, J=8.7, 2H), 6.70 (d, J=8.4, 1H), 6.68 (s, 1H), 4.47 (s, 2H), 4.27 (s, 2H), 4.10 (t, J=6.0, 2H), 3.72 (s, 3H), 3.32 (t, J=7.0, 2H), 2.61 (t, J=7.0, 2H), 2.46 (t, J=8.1, 2H), 2.17 (m, 2H), 2.03 (m, 2H); FDMS 528.82 (M).

EXAMPLE 6

Preparation of 2-[4-[4-Methoxy-4-oxobutoxy]phenyl]-3-[3-methoxy-4-[3-(1-oxoethyl)imidazolidin-1-ylmethyl]benzyl]benzo[b]thiophene Oxalate

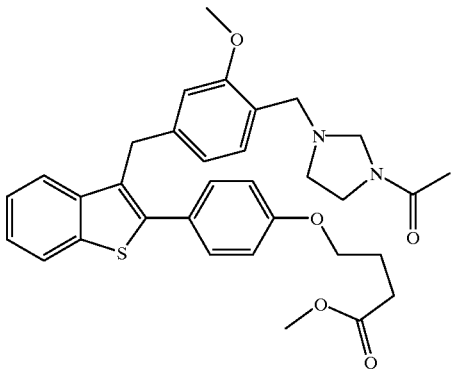

The ester of Example 3 (45 mg; 85 μmol) was dissolved in 0.5 mL of CH$_2$Cl$_2$ and 9 mg (1 eq) of BrCN was added. After stirring for 5 min at room temperature, 25 mL of EtOAc was added. The organics were washed with saturated Na$_2$CO$_3$ and dried by passage through Na$_2$SO$_4$. The mixture was concentrated under reduced pressure, placed under high vacuum for 1 h and dissolved in 1 mL of THF. Following addition of 143 mg (2.5 eq) of 1-acetylimidizolidine [Butula, Ivan. Justus Liebigs Ann. Chem., 718, 260–3 (1968)], the mixture was stirred at room temperature overnight. Saturated NaHCO$_3$ (25 mL) was added, and extraction was carried out with EtOAc (4×25 mL). The combined organics were dried by passage through Na$_2$SO$_4$. The title compound (0.15 g; 53% yield) was purified by flash chromatography on silica gel eluting with a gradient of EtOAc(100–90%)/Et$_3$N (0–5%)/MeOH(0–5%).

Anal. calc'd for C$_{33}$H$_{36}$N$_2$O$_5$S.C$_2$H$_2$O$_4$: C, 63.43; H, 5.78; N, 4.23. Found: C, 63.15; H, 5.85; N, 4.05. FDMS 572.2 (M).

EXAMPLE 7

Preparation of 2-[4-[4-Hydroxy-4-oxobutoxy]phenyl]-3-[3-methoxy-4-[3-(1-oxoethyl)imidazolidin-1-ylmethyl]benzyl]benzo[b]thiophene

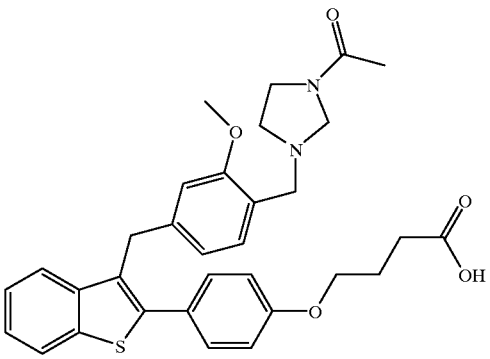

The title compound was prepared from the above ester (Example 6) essentially by the method of Example 14 in 93% yield.

$^1$H NMR (MeOH-d$_4$) δ 7.84 (d, J=7.4 Hz, 1H), 7.59 (d, J=7.5 Hz, 1H), 7.43 (d, J=8.6 Hz, 2H), 7.30 (m, 3H), 7.00 (d, J=7.0 Hz, 2H), 6.89 (s, 1H), 6.79 (d, J=7.5 Hz, 1H), 4.36 (s,

2H), 4.33 (s, 2H), 4.07 (t, J=5.1, 2H), 3.87 (m, 2H), 3.80 (s, 3H), 3.74 (m, 2H), 3.31 (s, 2H), 2.52 (t, J=7.4, 2H), 2.08 (m, 5H); FABMS 559.3 (M+1 for free base).

EXAMPLE 8

Preparation of 3-[4-[2-(1-Pyrrolidinyl)ethoxy] benzyl]-2-[4-(4-methoxy-4-oxobutoxy)phenyl]benzo [b]thiophene

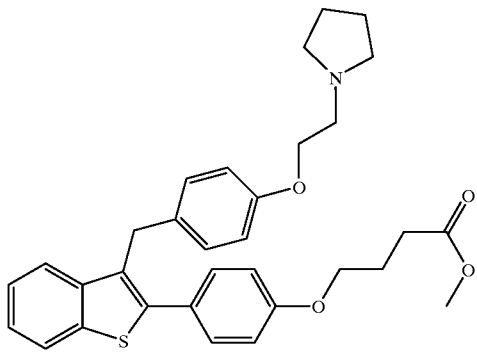

A. 2-(4-Methoxyphenyl)benzo[b]thiophen-3-yl 4-[2-(1-Pyrrolidinyl)ethoxy]phenyl Ketone.

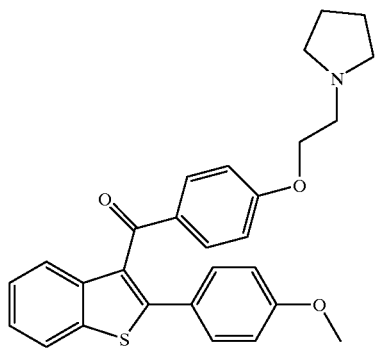

Sodium hydride (0.69 g of 60% NaH in mineral oil; 17.22 mmol) was suspended in 15 mL of dry DMF in a flame-dried, argon-filled flask. After stirring for 15 min, a solution of 4-(1-pyrrolidinyl)ethanol was added. After stirring for 15 min and gas evolution had ceased, 4-fluorophenyl 2-(4-methoxyphenyl)benzo[b]thiophen-3-yl ketone [prepared by acylation of 2-(4-methoxyphenyl)benzo[b]thiophene with 4-fluorobenzoyl chloride] (5.2 g; 14.34 mmol) in 15 mL of dry DMF was added. The mixture was stirred at room temperature for 5 h, then poured into 25 mL of water. Extraction was carried out with EtOAc (4×25 mL). The combined organics were washed with brine and dried by passage through sodium sulfate. The title compound (5.12 g; 78% yield) was isolated as a colorless oil by flash chromatography on silica gel, eluting with a gradient of EtOAc (100–85%)/Et$_3$N(0–5%)/MeOH(0–10%).

$^1$NMR (CDCl$_3$) δ 7.85 (m, 1H), 7.76 (d, J=6.3, 2H), 7.63 (m, 1H), 7.36 (m, 4H), 6.77 (d, J=7.2, 4H), 4.22 (t, J=5.3, 2H), 3.75 (s, 3H), 3.04 (t, J=5.2, 2H), 2.83 (br s, 4H), 1.90 (br s, 4H); FDMS 457 (M).

B. 2-(4-Methoxyphenyl)-3-[4-[2-(1-pyrrolidinyl)ethoxy] benzyl]benzo[b]thiophene.

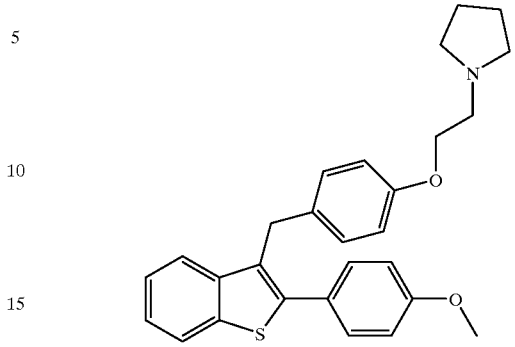

To the above ketone (Part A) (3.12 g; 11.2 mmol) in 40.0 mL of THF was added 0.42 g (11.2 mmol) of LAH at 0° C. The bath was removed and the mixture was stirred for 1 h. Hydrolysis was effected by addition of 0.42 mL of water, 0.42 mL of 5N NaOH, and 1.26 mL of water, followed by stirring for 1 h. After the mixture was filtered and washed with THF, the filtrate was concentrated; and the intermediate carbinol was dried in vacuo for 25 min. The carbinol was dissolved in methylene chloride (40.0 mL) under argon atmosphere and cooled in an ice-water bath. Triethylsilane (12.5 mL; 78.3 mmol) was added, followed by dropwise addition of 8.6 mL (112.0 mmol) of TFA. Upon completion of addition of TFA, the bath was removed and stirring was continued for 2 h. Saturated aqueous sodium bicarbonate (50 mL) was added, and extraction was carried out with EtOAc. The combined organics were washed with brine and dried by passage through sodium sulfate. The title compound (4.45 g; 90% yield) was isolated as a colorless oil by flash chromatography on silica gel, eluting with a gradient of EtOAc (100–95%)/Et$_3$N(0–5%).

$^1$NMR (CDCl$_3$) δ 7.87 (m, 1H), 7.77 (d, J=6.4, 2H), 7.65 (m, 1H), 7.34 (m, 4H), 6.78 (d, J=7.4, 4H), 4.20 (s, 2H), 4.15 (t, J=5.3, 2H), 3.73 (s, 3H), 3.14 (t, J=5.4, 2H), 2.91 (br s, 4H), 1.90 (br s, 4H); FDMS 444 (M+1).

C. 2-(4-Hydroxyphenyl)-3-[4-[2-(1-pyrrolidinyl)ethoxy] benzyl]benzo[b]thiophene.

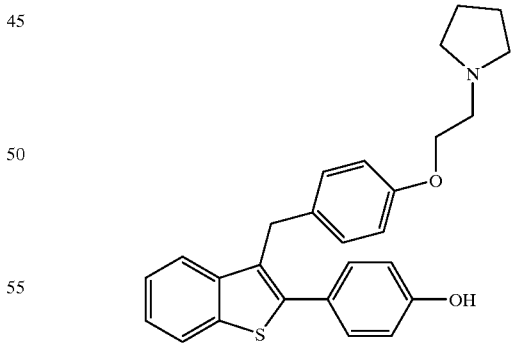

The above methyl ether (4.5 g; 10.1 mmol) (Part B) was dissolved in 45 mL of dichloroethane under an argon atmosphere and cooled in an ice-water bath. To this was added ethanethiol (6.0 mL; 81.1 mmol) and 5.41 g (40.6 mmol) of aluminum chloride, and the mixture was stirred in the cold bath for 1 h. Saturated NaHCO$_3$ was added, and stirring was continued while warming to room temperature for 1 h. The title compound (0.23 g; 74% yield) was isolated by filtration and washed with water.

¹NMR (CDCl₃) δ 7.83 (m, 1H), 7.47 (m, 1H), 7.29 (m, 2H), 6.98 (d, J=8.5, 2H), 6.83 (m, 4H), 6.69 (d, J=8.6, 2H), 4.15 (m, 4H), 3.05 (m, 2), 2.85 (br s, 4H), 1.91 (br s, 4H); FDMS 430 (M+1).

D. 3-[4-[2-(1-Pyrrolidinyl)ethoxy]benzyl]-2-[4-(4-methoxy-4-oxobutoxy)phenyl]benzo[b]thiophene.

By following essentially the procedure of Example 1-E the title compound was prepared from the above phenol (Part D) and methyl 4-chlorobutyrate in 83% yield. Purification was effected by flash chromatography on silica gel, eluting with a gradient of EtOAc(100–94%)/Et₃N(0–5%)/MeOH(0–2%).

¹NMR (CDCl₃) δ 7.84 (d, J=6.8, 1H), 7.52 (d, J=8.2, 1H), 7.43 (d, J=8.3, 2H), 7.30 (m, 2H), 7.07 (d, J=8.1, 2H), 6.93 (d, J=8.2, 2H), 6.83 (d, J=8.2, 2H), 4.22 (br s, 4H), 4.05 (t, J=5.6, 2H), 3.73 (s, 3H), 3.08 (br s, 2H), 2.88 (br s, 4H), 2.56 (t, J=7.2, 2H), 2.15 (m, 2H), 1.93 (br s, 4H) FDMS 529.2 (M).

EXAMPLE 9

Preparation of 2-[4-(4-Hydroxybutoxy)phenyl]-3-[4-[2-(1-pyrrolidinyl)ethoxy]benzyl]benzo[b]thiophene

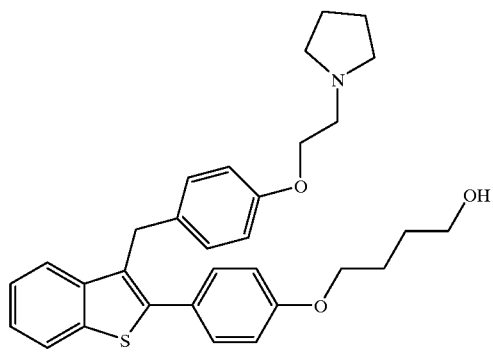

The ester of Example 8 (0.39 g; 0.74 mmol) was dissolved in THF and LAH (28 mg; 0.74 mmol) was added. The resultant mixture was stirred for 2 h. Workup was effected by addition of 2 drops of water, 2 drops of 5 N NaOH, and 6 drops of water. After stirring for 1 h, the mixture was filtered and washed with fresh THF. The title compound (0.22 g, 60% yield) was isolated by flash chromatography, eluting with a gradient of EtOAc(100–90%)/Et₃N(0–5%)/MeOH (0–5%).

¹NMR (CDCl₃) δ 7.88 (m, 1H), 7.43 (m, 5H), 7.09 (d, J=8.4, 2H), 6.96 (d, J=8.6, 2H), 6.84 (d, J=8.5, 2H), 4.34 (t, J=4.9, 2H), 4.24 (s, 2H), 4.08 (t, J=6.0, 2H), 3.77 (t, J=5.6, 2H), 3.24 (br s, 2H), 3.08 (br s, 4H), 2.04 (br s, 4H), 1.95 (m, 2H), 1.81 (m, 2H). FDMS 501.02 (M).

EXAMPLE 10

Preparation of 6-Hydroxy-3-[3-methoxy-4-(1-pyrrolidinylmethyl)benzyl]-2-[4-[2-methoxy-2-oxoethoxy]phenyl]benzo[b]thiophene

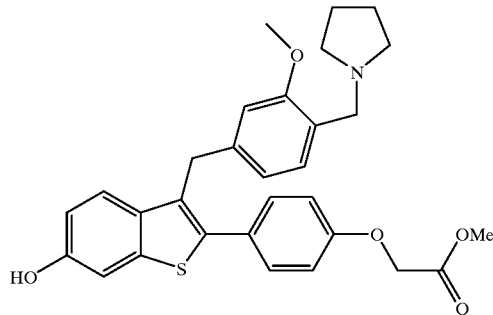

A suspension of 6-benzyloxy-2-(4-hydroxyphenyl)-3-[3-methoxy-4-(1-pyrrolidinylmethyl)benzyl]benzo[b]thiophene (100 mg) and cesium carbonate (330 mg) in DMF (2.0 mL) was treated with methyl bromoacetate (20 μL) and allowed to stir at ambient temperature under nitrogen for 1 h. The reaction mixture was diluted with brine (50 mL) and extracted with EtOAc (30 mL×3). The combined organic layers were dried with sodium sulfate and concentrated under reduced pressure. The residue was dissolved in THF (4.0 mL) and treated sequentially with a solution of ammonium formate (25% in H₂O, 2.0 mL) and 10% palladium on carbon (100 mg) at ambient temperature. The resulting mixture was stirred at ambient temperature under argon for 1.5 h before it was filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et₃N:MeOH:EtOAc (5:5:90) afforded the product (72 mg).

FDMS m/e: found 518 (M+H⁺); ¹H NMR (CDCl₃): δ 7.37 (d, 2H), 7.15 (d, 1H), 7.13 (d, 1H), 7.08 (s, 1H), 6.90 (d, 2H), 6.60 (d, 1H), 6.59 (s, 1H), 6.31 (d, 1H), 4.65 (s, 2H), 4.17 (s, 2H), 3.82 (s, 3H), 3.70 (s, 2H), 3.47 (s, 3H), 2.68 (m, 4H), 1.81 (m, 4H).

The 6-benzyloxy-2-(4-hydroxyphenyl)-3-[3-methoxy-4-[(1-pyrrolidinyl)methyl]benzyl]benzo[b]thiophene may be obtained using similar procedures to the following.

A. α-(4-Benzyloxyphenyl)-α-hydroxy-N,N-dimethylthioacetamide.

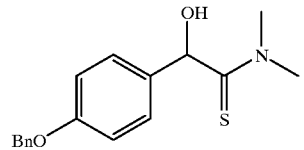

To a solution of distilled diisopropylamine (22.9 mL, 175 mmol) in 400 mL of anhydrous THF at −78° C. was added 1.6 M n-butyllithium in hexanes (100 mL, 160 mmol) over a period of 45 min. The mixture was stirred at −78° C. for 1.5 h. To the solution was cannulated over a period of 1 h a solution of 4-benzyloxybenzaldehyde (30.9 g, 146 mmol) and N,N-dimethylthioformamide (13.7 mL, 160 mmol) in 100 mL of distilled THF. The reaction mixture was stirred at −78° C. for 16 h. The reaction was then quenched with 500 mL of saturated NH₄Cl solution. The mixture was extracted with EtOAc (3×1 L), and the combined organic layers were dried over MgSO₄ and concentrated under reduced pressure. The residue was then recrystallyzed from EtOAc/hexanes to afford 20.0 g (66.5 mmol, 46%) of an off-white solid.

mp 104–107° C.; FDMS 301 (M+); Anal. Calcd for C₁₇H₁₉NO₂S: C, 67.75; H, 6.35; N, 4.65. Found: C, 67.61; H, 6.37; N, 4.57.

B. 6-Benzyloxy-2-(dimethylamino)benzo[b]thiophene.

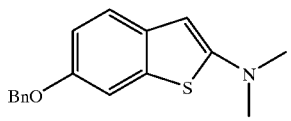

To a solution of the above thioacetamide (Part A) (500 mg, 1.66 mmol) in 65 mL of dry dichloroethane at room temperature was added dropwise methanesulfonic acid (0.54 ml, 8.3 mmol). The red reaction mixture was stirred for 1.5 h and then poured into 10 mL of saturated aqueous NaHCO₃ solution, followed by addition of 3 mL of H₂O, and stirred vigorously. The layers were separated and the organic layer was dried over MgSO₄ and concentrated under reduced pressure. The residue was then purified by flash chromatography (silica gel, 10% Et₂O/hexanes) to afford 327 mg (1.15 mmol, 70%) of a white solid.

mp 78–81° C.; FDMS 283 (M+); Anal. Calcd for C₁₇H₁₇NOS: C, 72.05; H, 6.05; N, 4.94. Found: C, 72.22; H, 6.15; N, 4.89.

C. 6-Benzyloxy-2-(dimethylamino)benzo[b]thiophen-3-yl 3-Methoxy-4-(1-pyrrolidinylmethyl)phenyl Ketone.

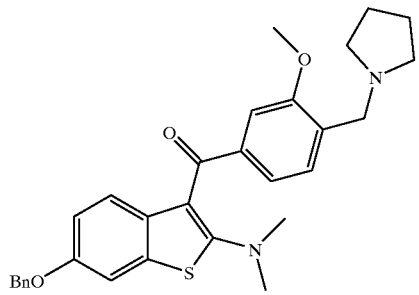

A solution of 6-benzyloxy-2-(dimethylamino)benzo[b] thiophene (2.5 g, 8.8 mmol) and 3-methoxy-4-(1-pyrrolidinylmethyl)benzoyl chloride hydrochloride (3.0 g, 1.3 equiv) in chlorobenzene (30 mL) was heated at 135° C. under nitrogen for 2 h. The cooled reaction mixture was diluted with brine (100 mL), neutralized with NaOH solution (5.0 M), and extracted with dichloromethane (100 mL×3). The combined organic layers were dried with sodium sulfate and concentrated under reduced pressure. Chromatography with Et₃N:EtOAc (5:95) afforded the product as a brown oil (3.7 g, 84%).

¹H NMR (CDCl₃): δ 7.5–6.9 (m, 11H), 5.10 (s, 2H), 3.90 (s, 3H), 3.71 (s, 2H), 2.91 (s, 6H), 2.60 (m, 4H), 1.83 (m, 4H): FDMS m/e: 500.0 (M⁺).

D. 4-Bromophenyl Triisopropylsilyl Ether.

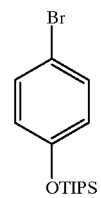

To 4-bromophenol (6.1 g, 35 mmol) and imidazole (2.6 g) in DMF (30 mL) at ambient temperature was added slowly triisopropylsilyl trifluoromethanesulfonate (10.5 mL) while stirring. The resulting mixture was stirred at ambient temperature for 1 h before dilution with water (200 mL) and extraction with EtOAc (100 mL×3). The combined organic layers were dried with sodium sulfate and concentrated under reduced pressure. Chromatography with EtOAc-hexanes (0–5% gradient elusion) afforded the product as a colorless oil (11.2 g, 96%).

¹H NMR (CDCl₃): δ 7.32 (d, J=9.1 Hz, 2H), 6.77 (d, J=9.1 Hz, 2H), 1.23 (m, 3H), 1.10 (d, J=7.0 Hz, 18H); FDMS m/e: 330 (M+H⁺).

E. 6-Benzyloxy-2-[4-hydroxyphenyl]benzo[b]thiophen-3-yl 3-Methoxy-4-(1-pyrrolidinylmethyl)phenyl Ketone.

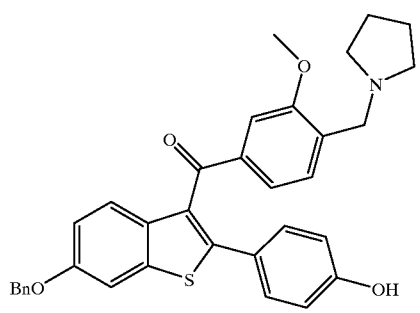

Magnesium turnings (0.24 g) were placed in a two-neck 100 mL round-bottom flask fitted with a reflux condenser and a magnetic stir bar. The whole apparatus was flame-dried and allowed to cool to ambient temperature. Dry THF (17 mL) and a small crystal of iodine were then introduced followed by slow addition of 4-bromophenyl triisopropyl-silyl ether (3.5 g) while stirring at ambient temperature. The reaction mixture was warmed to a gentle reflux for 1 h or until the magnesium turnings were completely consumed to give a 0.5 M solution of the Grignard reagent. This freshly prepared Grignard solution (15 mL) was added slowly to a stirring solution of 6-benzyloxy-2-(dimethylamino)benzo[b] thiophen-3-yl 3-methoxy-4-(1-pyrrolidinylmethyl)phenyl ketone (2.5 g, 5.0 mmol) in THF (15.0 mL) at 0° C. under argon. The mixture was stirred at 0° C. for 2 h before quenching with saturated aqueous NH₄Cl solution (50 mL) and extraction with CH₂Cl₂ (50 mL×3). The combined organic layers were dried with sodium sulfate and concentrated under reduced pressure. Chromatography with EtOAc afforded a oily brown material as the major fraction. This material was dissolved in THF (25 mL), treated with a solution of tetrabutylammonium fluoride (1.0 M in THF, 6 mL) at ambient temperature for 1 h, and then concentrated under reduced pressure. Chromatography with Et₃N:MeOH:EtOAc (5:10:85) afforded the title compound as a yellow foam (2.75 g, 100%).

¹H NMR (CDCl₃): δ 7.75 (d, 1H), 7.52–7.30 (m, 6H), 7.20 (d, 2H), 7.20–7.08 (m, 4H), 6.60 (d, 2H), 5.18 (s, 2H), 3.70 (s, 5H), 2.68 (m, 4H), 1.85 (m, 4H).

F. 6-Benzyloxy-2-(4-hydroxyphenyl)-3-[3-methoxy-4-(1-pyrrolidinylmethyl)benzyl]benzo[b]thiophene.

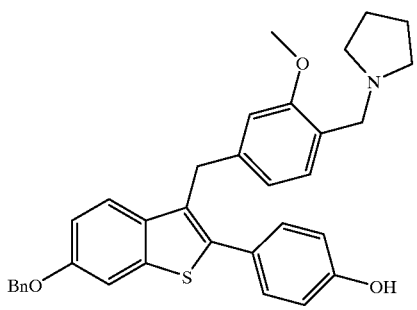

6-Benzyloxy-2-(4-hydroxyphenyl)benzo[b]thiophen-3-yl 3-methoxy-4-(1-pyrrolidinylmethyl)phenyl ketone (2.75 g, 5.0 mmol) in THF (25 mL) was treated with lithium aluminum hydride (420 mg) at 0° C. for 2 h, then quenched with water (1 mL) and sodium hydroxide (1.0 M, 3 mL). Stirring was continued for 45 min. The reaction mixture was diluted with brine (100 mL) and extracted with dichloromethane (100 mL×3). The combined organic layers were dried with sodium sulfate and concentrated in vacuo to give a white foam-like material. This material was dissolved in dichloromethane (50 mL), treated with triethylsilane (6.0 mL) and trifluroacetic acid (5.0 mL) at 0° C. for 2 h, and concentrated under reduced pressure. The residue was extracted with dichloromethane (100 mL×3) which was washed with saturated aqueous sodium bicarbonate (100 mL). The combined organic layers were dried with sodium sulfate and concentrated. Chromatography with Et$_3$N:MeOH:EtOAc (5:5:90) afforded the product as a white solid (2.1 g, 78%).

$^1$H NMR (CDCl$_3$): δ 7.50–7.27 (m, 9H), 7.15 (d, 1H), 6.96 (d, 1H), 6.69 (d, 2H), 6.65 (d, 1H), 6.55 (s, 1H), 5.12 (s, 2H), 4.18 (s, 2H), 3.71 (s, 2H), 3.57 (s, 3H), 2.70 (m, 4H), 1.83 (m, 4H); FDMS m/e: 536 (M+H$^+$).

EXAMPLE 11

Preparation of 6-Hydroxy-3-[3-methoxy-4-(1-pyrrolidinylmethyl)benzyl]-2-[4-[2-hydroxyethoxy]phenyl]benzo[b]thiophene

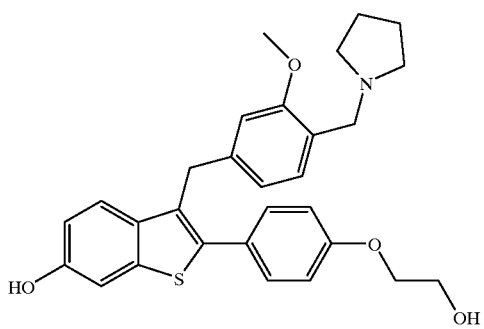

To 6-hydroxy-2-[4-(2-methoxy-2-oxoethoxy)phenyl]-3-[3-methoxy-4-(1-pyrrolidinylmethyl)benzyl]benzo[b]thiophene (36 mg) in THF (2 mL) was added lithium aluminum hydride (16 mg) and the mixture was stirred under argon at ambient temperature for 1 h. The reaction was quenched with water (1 mL) and sodium hydroxide solution (1.0 M, 1 mL) while stirring continued for 30 min. The mixture was then diluted with brine (50 mL) and extracted with dichloromethane (30 mL×3). The combined organic layers were dried with sodium sulfate and concentrated in vacuo. Chromatography with Et$_3$N:MeOH:EtOAc (5:10:85) afforded the product (29 mg).

FDMS m/e: found 490 (M+H$^+$); $^1$H NMR (CD$_3$OD): δ 7.38 (d, 2H), 7.35 (d, 1H), 7.19 (s, 1H), 7.18 (d, 1H), 6.97 (d, 2H), 6.80 (s, 1H), 6.77 (d, 1H), 6.71 (d, 1H), 4.21 (s, 2H), 4.05 (t, 2H), 4.03 (s, 2H), 3.87 (t, 2H), 3.73 (s, 3H), 3.02 (m, 4H), 1.94 (m, 4H).

EXAMPLE 12

Preparation of 6-Hydroxy-2-[4-(2-hydroxy-2-oxoethoxy]phenyl)-3-[3-methoxy-4-(1-pyrrolidinylmethyl)benzyl]benzo[b]thiophene

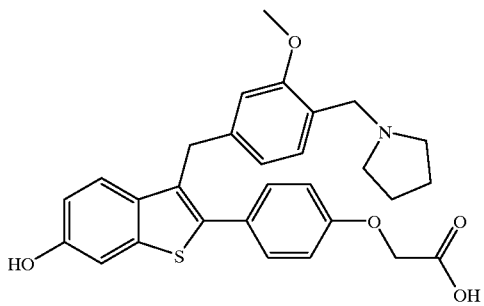

The title compound was prepared from the ester of Example 10 by using the same procedure employed for the preparation of Example 14.

$^1$H NMR (CDCl$_3$): δ 7.38 (m, 2H), 7.20 (m, 2H), 6.96 (m, 2H), 6.82 (m, 4H), 4.26 (s, 2H), 4.25 (s, 2H), 3.78 (s, 3H), 3.76 (s, 2H), 3.19 (m, 4H), 2.06 (m, 4H).

EXAMPLE 13

Preparation of 6-Hydroxy-3-[3-methoxy-4-(1-pyrrolidinylmethyl)benzyl]-2-[4-[4-methoxy-4-oxobutoxy]phenyl]benzo[b]thiophene

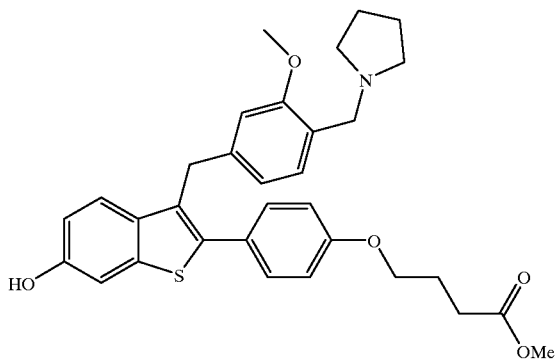

37

A. 6-Benzyloxy-3-[3-methoxy-4-(1-pyrrolidinylmethyl)benzyl]-2-[4-[4-methoxy-4-oxobutoxy]phenyl]benzo[b]thiophene.

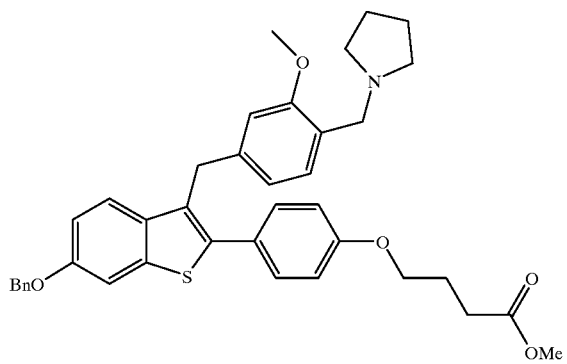

A suspension of 6-benzyloxy-2-(4-hydroxyphenyl)-3-[3-methoxy-4-(1-pyrrolidinylmethyl)benzyl]benzo[b]thiophene (161 mg) and cesium carbonate (700 mg) in DMF (2.0 mL) was treated with methyl 4-chlorobutyrate (45 μL) and allowed to stir at 90° C. under nitrogen for 3 h. The reaction mixture was diluted with water (50 mL), neutralized with dilute hydrochloric acid and extracted with EtOAc (30 mL×3). The combined organic layers were dried with sodium sulfate and concentrated under reduced pressure. Chromatography with Et$_3$N-EtOAc (0–5%) afforded the product.

$^1$H NMR (CDCl$_3$): δ 7.48–7.34 (m, 9H), 7.20 (d, 1H), 7.00 (d, 1H), 6.91 (d, 2H), 6.70 (d, 1H), 6.67 (s, 1H), 5.13 (s, 2H), 4.21 (s, 2H), 4.04 (t, 2H), 3.71 (s, 3H), 3.62 (s, 2H), 2.56 (m, 6H), 2.14 (m, 2H), 1.78 (m, 4H).

B. 6-Hydroxy-3-[3-methoxy-4-(1-pyrrolidinylmethyl)benzyl]-2-[4-[4-methoxy-4-oxobutoxy]phenyl]benzo[b]thiophene.

6-Benzyloxy-3-[3-methoxy-4-(1-pyrrolidinylmethyl)benzyl]-2-[4-(4-methoxy-4-oxobutoxy)phenyl]benzo[b]thiophene (147 mg) in THF (3.0 mL) was treated sequentially with a solution of ammonium formate (25% in H$_2$O, 2.0 mL) and 10% palladium on carbon (100 mg) at ambient temperature. The resulting mixture was stirred at ambient temperature under argon for 3 h before it was filtered through diatonaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with Et$_3$N:EtOAc (0–5%) afforded the product (108 mg).

$^1$H NMR (CDCl$_3$): δ 7.37 (d, 2H), 7.15 (d, 1H), 7.14 (d, 1H), 7.10 (s, 1H), 6.88 (d, 2H), 6.64 (d, 1H), 6.60 (s, 1H), 6.28 (d, 1H), 4.17 (s, 2H), 4.02 (t, 2H), 3.70 (s, 3H), 3.46 (s, 2H), 2.67 (m, 4H), 2.54 (t, 2H), 2.12 (m, 2H), 1.81 (m, 4H).

38

EXAMPLE 14

Preparation of 6-Hydroxy-3-[3-methoxy-4-(1-pyrrolidinylmethyl)benzyl]-2-[4-[4-hydroxy-4-oxobutoxy]phenyl]benzo[b]thiophene

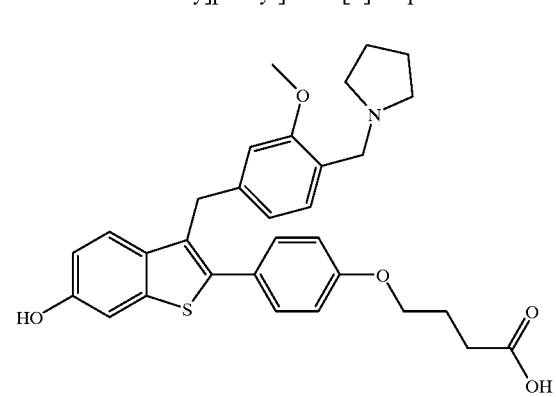

6-Hydroxy-3-[3-methoxy-4-(1-pyrrolidinylmethyl)benzyl]-2-[4-[4-methoxy-4-oxobutoxy]phenyl]benzo[b]thiophene (147 mg) was dissolved in THF:MeOH:H$_2$O (3:1:1, 3.0 mL), treated with lithium hydroxide monhydrate (12 mg) in one portion, and allowed to stir at ambient temperature for 4 days. The reaction mixture was neutralized with dilute HCl and concentrated in vacuo. The residue was dissolved in methanol. The solution was transfered to a clean vial and solvent was removed with a stream of nitrogen to give the product as an off-white solid. (100 mg).

FDMS m/e: found 532 (M+H$^+$); $^1$H NMR (CD$_3$OD): δ 7.37 (d, 4H), 7.25 (d, 1H), 7.20 (s, 1H), 6.93 (d, 2H), 6.81 (s, 1H), 6.80 (d, 1H), 6.71 (d, 1H), 4.23 (s, 2H), 4.20 (s, 2H), 4.00 (t, 2H), 3.72 (s, 3H), 3.23 (m, 4H), 2.42 (t, 2H), 2.02 (m, 6H).

EXAMPLE 15

Preparation of 6-Hydroxy-3-[4-[2-(1-pyrrolidinyl)ethoxy]-benzyl]-2-[4-(3-carboxypropyloxy)phenyl]benzo[b]thiophene Hydrochloride

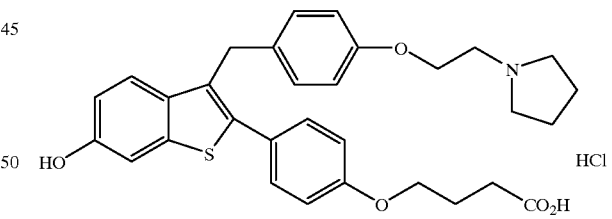

A. 6-Benzyloxy-2-dimethylaminobenzo[b]thiophene-3-yl 4-[2-(1-Pyrrolidinyl)ethoxy]phenyl Ketone.

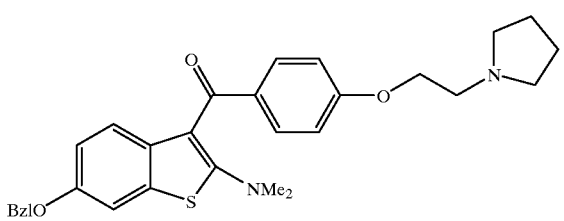

By essentially following the procedure described in Example 10-C, the title compound was prepared as an oil starting from 6-benzyloxy-2-dimethylaminobenzo[b]thiophene and 4-[2-(1-pyrrolidinyl)ethoxy]benzoyl chloride hydrochloride in 38% yield following MPLC (SiO$_2$; 15% then 20% then 30% THF with 5% TEA in hexanes).

FDMS 500 (M+); Anal. calcd for C$_{30}$H$_{32}$N$_2$O$_3$S: C, 71.97; H, 6.44; N, 5.60. Found: C, 72.18; H, 6.29; N, 5.53.

B. 6-Benzyloxy-2-(4-triisopropylsilyloxyphenyl)benzo[b]thiophene-3-yl 4-[2-(1-Pyrrolidinyl)ethoxy]phenyl Ketone.

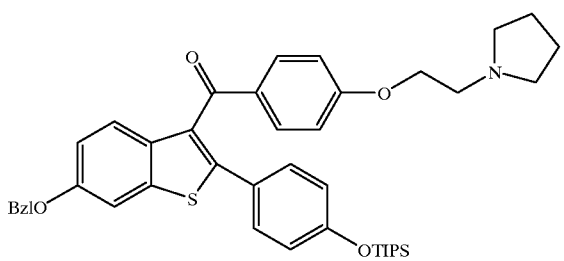

By essentially following the procedure described in Example 10-E, the title compound was prepared as an oil starting from 6-benzyloxy-2-dimethylaminobenzo[b]thiophene-3-yl 4-[2-(1-pyrrolidinyl)ethoxy]phenyl ketone (Part A) and 1-bromo-4-(triisopropylsilyloxy)benzene in 57% yield following MPLC (SiO$_2$; 10% then 15% then 20% THF with 5% TEA in hexanes).

FDMS 706 (M+); Anal. calcd for C$_{43}$H$_{51}$NO$_4$S: C, 74.63; H, 7.72; N, 2.02. Found: C, 74.43; H, 7.59; N, 2.10.

C. 6-Benzyloxy-2-(4-hydroxyphenyl)benzo[b]thiophene-3-yl 4-[2-(1-Pyrrolidinyl)ethoxy]phenyl Ketone.

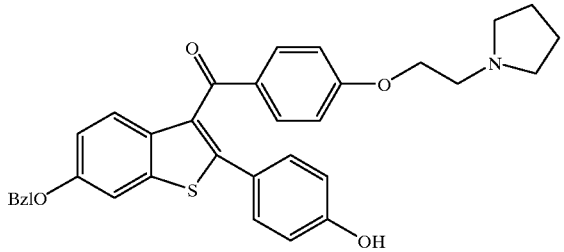

By essentially following the procedure described in Example 10-E, the title compound was prepared as a foam starting from 6-benzyloxy-2-(4-triisopropylsilyloxyphenyl)benzo[b]thiophene-3-yl 4-[2-(1-pyrrolidinyl)ethoxy]phenyl ketone (Part B) in quantitative yield following MPLC (SiO$_2$; 0.5% in CHCl$_3$ sat'd with NH$_4$OH).

FDMS 550 (M+1).

D. 6-Benzyloxy-2-(4-hydroxyphenyl)-3-[4-[2-(1-pyrrolidinyl)ethoxy]benzyl]benzo[b]thiophene.

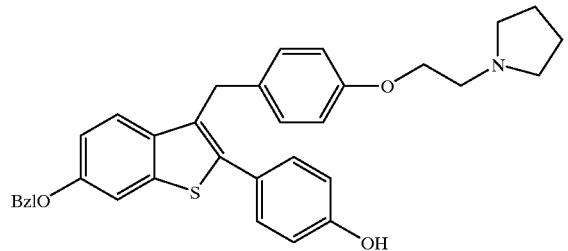

By essentially following the procedure described below in Example 25, Part B, the title compound was prepared as a foam starting from 6-benzyloxy-2-(4-hydroxyphenyl)benzo[b]thiophene-3-yl 4-[2-(1-pyrrolidinyl)ethoxy]phenyl ketone (Part C) in 52% yield following MPLC (SiO$_2$; 0.5% in CHCl$_3$ sat'd with NH$_4$OH).

FDMS 536 (M+1); Anal. calcd for C$_{34}$H$_{33}$NO$_3$S: C, 76.23; H, 6.21; N, 2.62. Found: C, 76.45; H, 6.09; N, 2.91.

E. 6-Benzyloxy-3-[4-[2-(1-pyrrolidinyl)ethoxy]benzyl]-2-[4-(3-cyanopropyloxy)phenyl]benzo[b]thiophene.

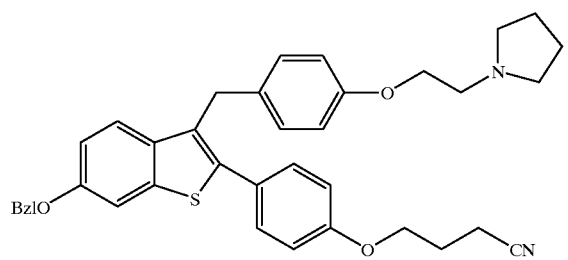

A mixture of 6-benzyloxy-2-(4-hydroxyphenyl)-3-[4-[2-(1-pyrrolidinyl)ethoxy]benzyl]benzo[b]thiophene (Part D), 4-bromobutyronitrile (1.2 mol/mol of phenol), and Cs$_2$CO$_3$ (2 mol/mol of phenol) in DMF (about 10 mL/mmol of phenol) was heated to 80° C. for 3 h, poured into 4 volumes of water and extracted with EtOAc. After drying (K$_2$CO$_3$) and evaporation, the title compound was obtained as a foam in 98% yield following MPLC (SiO$_2$; 0.5% in CHCl$_3$ sat'd with NH$_4$OH).

FDMS 603 (M+); Anal. calcd for C$_{38}$H$_{38}$N$_2$O$_3$S: C, 75.72; H, 6.35; N, 4.65. Found: C, 75.66; H, 6.18; N, 4.72.

F. 6-Hydroxy-3-[4-[2-(1-pyrrolidinyl)ethoxy]benzyl]-2-[4-(3-cyanopropyloxy)phenyl]benzo[b]thiophene.

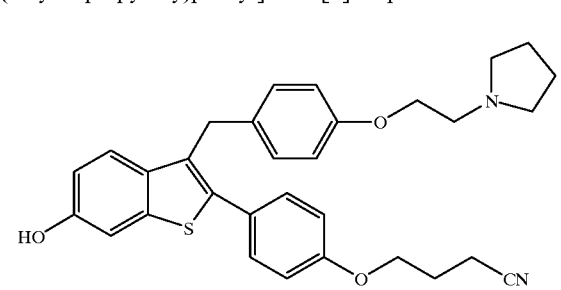

By essentially following the debenzylation procedure described in Example 10, the title compound was prepared as an oil starting from 6-benzyloxy-3-[4-[2-(1-pyrrolidinyl)ethoxy]benzyl]-2-[4-(3-cyanopropyloxy)phenyl]benzo[b]thiophene (Part E) in 71% yield following radial chromatography (SiO$_2$; 1.0% in CHCl$_3$ sat'd with NH$_4$OH).

FDMS 513 (M+1); Anal. calcd for $C_{31}H_{32}N_2O_3S$: C, 72.63; H, 6.29; N, 5.46. Found: C, 72.87; H, 6.26; N, 5.52.

G. 6-Hydroxy-3-[4-[2-(1-pyrrolidinyl)ethoxy]benzyl]-2-[4-(3-carboxypropyloxy)phenyl]benzo[b]thiophene Hydrochloride.

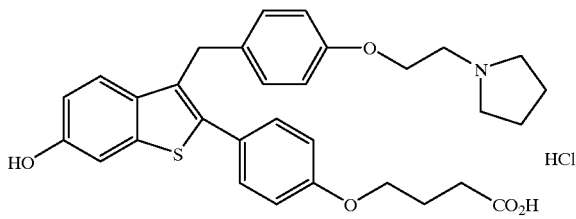

A solution of 400 mg (0.83 mmol) of 6-hydroxy-3-[4-[2-(1-pyrrolidinyl)ethoxy]benzyl]-2-[4-(3-cyanopropyloxy)phenyl]benzo[b]thiophene (Part F) in 5 mL of MeOH was treated with 5 mL of 5 N aq HCl and the mixture heated to reflux for 24 h. The mixture was concentrated in vacuo. The residue was reconstituted in 5 mL of dioxane and the mixture treated with 5 mL of 5 N aq HCl. The solution was heated to mild reflux for 6 h and was concentrated in vacuo. The solid was dissolved in 5 mL of $H_2O$ and the solution lyopholized to afford 300 mg (0.56 mmol; 68%) of the title compound as a white solid.

FDMS 532 (M+1).

EXAMPLE 16

Preparation of 2-[4-[4-Methoxy-4-oxobutoxy]phenyl]-3-[3-methoxy-4-[2-(1-pyrrolidinyl)ethoxy]benzyl]benzo[b]thiophene Oxalate

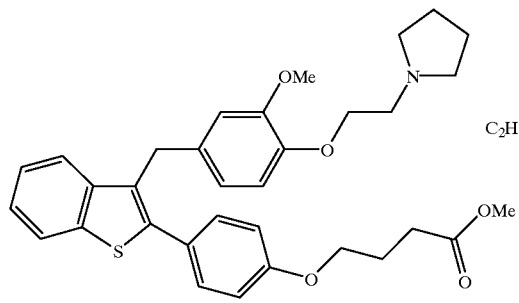

A. 4-(2-Benzo[b]thiophenyl)phenyl Triisopropylsilyl Ether

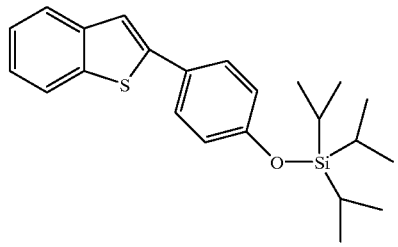

A mixture of 2-(4-hydroxyphenyl)benzothiophene (2.84 g, 12.6 mmol), triethylamine (2.5 g, 25.2 mmol) and 30 mL dry DMF was cooled in an ice bath and treated with triisopropylsilyl triflate (7.7 g, 25.2 mmol). The reaction was allowed to warm to room temperature, quenched with 100 mL brine then extracted twice with 50 mL EtOAc. The combined extract was washed with brine, dried over $MgSO_4$ and concentrated to dryness. The resulting solid was purified by chromatrography ($SiO_2$, 5% EtOAc in Hexanes) to yield 4.7 g (12.3 mmol, 98%) of a solid.

FDMS 382 (M+); $^1$H NMR (DMSO-d6) δ 7.95–7.9 (m, 1H). 7.82–7.77 (m, 1H), 7.72–7.70 (m, 2H), 7.65 (s, 1H), 7.4–7.27 (d, 2H), 7.0–6.92 (d, 2H), 1.35–1.18 (m, 3H), 1.15–1.05 (m, 18H)

B. 2-(4-Triisopropylsilyloxyphenyl)benzo[b]thiophen-3-yl 3-Methoxy-4-[2-(1-pyrrolidinyl)ethoxy]phenyl Ketone.

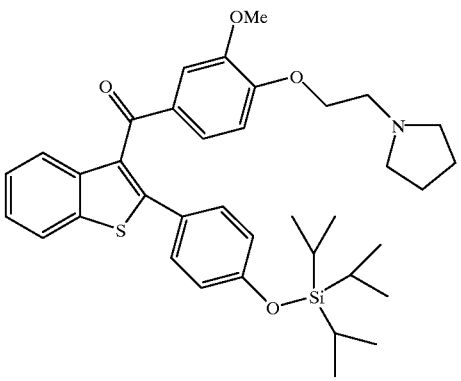

A mixture of 3.5 g (11.6 mmol) of 4-[2-(1-pyrrolidinyl)ethoxy]-3-methoxybenzoic acid hydrochloride (see below), 30 mL $ClCH_2CH_2Cl$, 10 mL of oxalyl chloride and 1 drop of DMF was stirred at ambient temperature for 16 hours then evaporated in vacuo, to dryness. The resulting solid was disolved in 50 mL 1,2-dichloroethane and concentrated under reduced pressure. It was redissolved in 100 mL 1,2-dichloroethane and treated sequentially with a solution of 47 mL 1 M $TiCl_4$ in $CH_2Cl_2$ and 4.4 g (11.6 mmol) of 4-(2-benzo[b]thiophenyl)phenyl triisopropylsilyl ether 0° C. The reaction was protected from light and stirred at 0° C. for 4 h at which time it was quenched by carefully pouring it into 400 mL of vigorously stirred saturated aqueous $NaHCO_3$. Added 300 mL EtOAc and separated the layers. The aqueous layer was treated with 200 mL saturated aqueous sodium potassium tartrate and extracted twice with 100 mL EtOAc. The combined organic layer was washed with brine, dried over $MgSO_4$ and evaporated in vacuo to give an oil which was purified by chromatography ($SiO_2$; Hex/THF/$Et_3$N 85-10-5%) to afford 5.84 g (9.3 mmol; 80%) of the desired compound as an oil.

FDMS 629 (M+); $^1$H NMR ($CDCl_3$) δ 7.82–7.85 (m, 1H), 7.7–7.5 (d, 1H), 7.5–7.45 (d, 1H), 7.4–7.2 (d, 5H), 6.8–6.75 (d, 2H), 6.65–6.6 (m, 1H), 4.18 (t, 2H); 3.85 (s, 3H), 2.95 (t, 2H), 2.65–2.55 (m, 4H), 1.85–1.75 (m, 4H), 1.35–1.18 (m, 3H), 1.15–1 (m, 18H).

C. 2-(4-Triisopropylsilyloxyphenyl)-3-[3-methoxy-4-[2-(1-pyrrolidinyl)ethoxy]benzyl]benzo[b]thiophene.

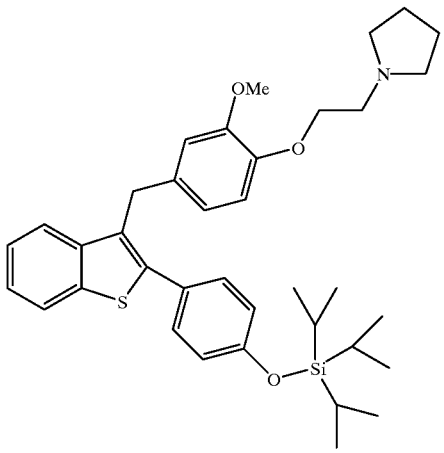

The above ketone (5.4 g, 8.6 mmol) was dissolved in 100 mL dry THF, cooled to 0° C. under nitrogen and treated with 8.6 mL of 1 M lithum aluminum hydride in THF. The reaction was stirred at 0° C. for 1 hour then quenched with a saturated solution of Na₂SO₄. Added 200 mL THF and filtered through a pad of diatomaceous earth. Concentration yielded 5.17 g of a foam.

A mixture of the foam and triethylsilane (5 g, 43 mmol) in 100 mL CH₂Cl₂, was cooled to 0° C. and treated with 9.8 g (86 mmol) of trifluoroacetic acid. After stirring 45 minutes at 0° C. the solution was quenched with 100 mL saturated aqueous NaHCO₃. The layers were separated and the organic layer was dried over MgSO. Concentration to dryness yielded an oil which was purified by chromatography (SiO₂; Hex/THF/Et₃N 75-20-5%) to recover 4.9 g (7.96 mmol, 93%) of the desired product as an oil.

FDMS 615 (M+); ¹H NMR (CDCl₃) δ 7.85–7.8 (m, 1H). 7.6–7.5 (m, 1H), 7.4–7.39 (m, 2H), 7.31–7.28 (d, 2H), 6.88 (d, 2H), 6.84 (d, 1H), 6.75 (d, 1H), 6.63–6.6 (m, 1H), 4.2 (s, 2H), 4.18 (t, 2H); 3.75 (s, 3H), 3.15–3.05 (m, 2H), 2.95–2.77 (m, 4H), 1.95–1.85 (m, 4H), 1.35–1.18 (m, 3H), 1.15–1.05 (m, 18H).

D. 2-(4-Hydroxyphenyl)-3-[3-methoxy-4-[2-(1-pyrrolidinyl)ethoxy]benzyl]benzo[b]thiophene.

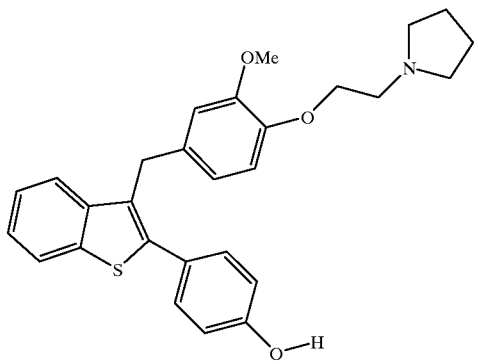

The above silyl ether (2 g, 3.25 mmol) was dissolved in 25 mL THF and treated with 2 g (34 mmol) of potassium fluoride and 25 mL H₂O. The reaction was stirred for 16 hours at ambient temperature then refluxed for 1 hour. The layers were separated and the aqueous layer was extracted with 30 mL EtOAc. The combined organic layer was dried over MgSO₄ and concentrated to an oily solid which was mixed with 5 mL hexanes and filtered to recover 1.04 g (2.3 mmol, 70%) of an off-white solid.

FDMS 460 (M+1); ¹H NMR DMSO-d₆) δ (m, 1H). 7.58–7.55 (m, 1H), 7.34–7.27 (m, 4H), 6.86–6.83 (m, 2H), 6.77–6.74 (m, 2H), 6.45 (d, 1H); 4.13 (s, 2H), 3.90 (t, 2H), 3.62 (s, 3H), 2.68 (t, 2H), 2.3–2.2 (m, 4H), 1.62–1.6 (m, 4H); Anal. Calcd for C₂₈H₂₉NO₃S: C, 73.17; H, 6.36; N, 3.05; Found: C, 73.43; H, 6.51; N, 3.12.

E. 2-[4-[4-Methoxy-4-oxobutoxy]phenyl]-3-[3-methoxy-4-[2-(1-pyrrolidinyl)ethoxy]benzyl]benzo[b]thiophene Oxalate.

A mixture of the above benzothiophene (0.95 g, 2.1 mmol), cesium carbonate (2.7 g, 8.3 mmol) and 20 mL dry DMF was treated with methyl-3-chlorobutyrate (315 µL, 2.6 mmol) and heated at 80° C. for 2 hours. The reaction mixture was cooled to room temperature, poured into a saturated aqueous solution of NaHCO₃ and extracted twice with 30 mL EtOAc. The combined organic layer was washed three times with 40 mL brine, dried over MgSO₄ and concentrated to a solid. Purification by chromatrography (SiO₂; Hex/THF/Et₃N 65-30-5%) yielded 1.05 g of a white solid which was converted to its oxalate salt.

FDMS 559 (M+); ¹H NMR (CDCl₃) δ 7.85 (m, 1H), 7.5 (m, 1H), 7.43 (d, 2H). 7.35–7.23 (m, 2H), 6.93 (d, 2H), 6.72 (d, 1H) 6.7 (s, 1H), 6.61 (d, 1H), 4.21 (s, 2H), 4.17 (t, 2H), 4.09 (t, 2H), 3.70 (s, 3H); 3.75 (s, 3H), 2.94 (t, 2H),2.6–2.64 (m, 4H), 2.55 (t, 2H), 2.2–2.1 (m, 2H), 1.83–1.78 (m, 4H) Anal. Calcd for C₃₃H₃₇NO₅S.0.75 C₂H₂O₄: C, 66.06; H, 6.19; N, 2.23; Found: C, 66.12; H, 6.06; N, 2.17.

The benzoic acid for Part B, above, may be obtained as follows.

F. Methyl 3-Methoxy-4-[2-(1-pyrrolidinyl)ethoxylbenzoate.

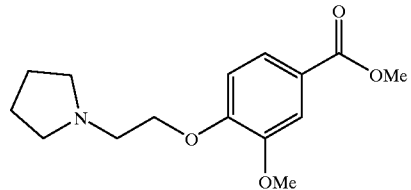

The substituted pyrrolidine was prepared in 94% yield by heating 4-hydroxy-3-methoxybenzoate with excess 1-(2-chloroethyl)pyrrolidine hydrochloride and K₂CO₃ in DMF, followed by cooling, dilution into cold water and extraction with EtOAc. The product was obtained following drying (Na₂SO₄) and evaporation.

¹H NMR (CDCl₃) δ 7.63 (d, 1H), 7.53 (s, 1H), 6.9 (d, 1H), 4.2 (t, 2H), 3.89 (s, 3H), 3.88 (s, 3H), 2.96 (t, 2H), 2.64–2.61 (m, 4H), 1.85–1.75 (m, 4H); FDMS 279 (M+).

G. 3-Methoxy-4-[2-(1-pyrrolidinyl)ethoxy]benzoic Acid Hydrochloride.

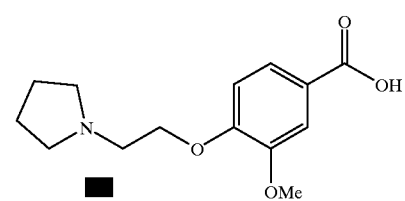

The benzoic acid hydrochloride was prepared in 63% yield from methyl 3-methoxy-4-[2-(1-pyrrolidinyl)ethoxy]benzoate by refluxing the above ester with 5N HCl, followed by mixing with toluene/EtOH before evaporation to drynes. Trituration with hot EtOAc afforded the benzoic acic hydrochloride.

$^1$H NMR (DMSO-$d_6$) δ 11.27 (bs, 2H), 7.57 (d, 1H), 7.55 (s, 1H), 7.12 (d, 1H), 4.44 (t, 2H), 3.82 (s, 3H), 3.5 (bs, 4H), 3.1 (bs, 2H); 1.98 (bs, 2H), 1.89 (bs, 2H); Anal. Calcd for $C_{14}H_{19}NO_4$·HCl: C, 55.72; H, 6.68; N, 4.64. Found: C, 56.01; H, 6.88; N, 4.70.

EXAMPLE 17

Preparation of 2-[4-[4-Hydroxy-4-oxobutoxy]phenyl]-3-[3-methoxy-4-[2-(1-pyrrolidinyl)ethoxy]benzyl]benzo[b]thiophene Oxalate

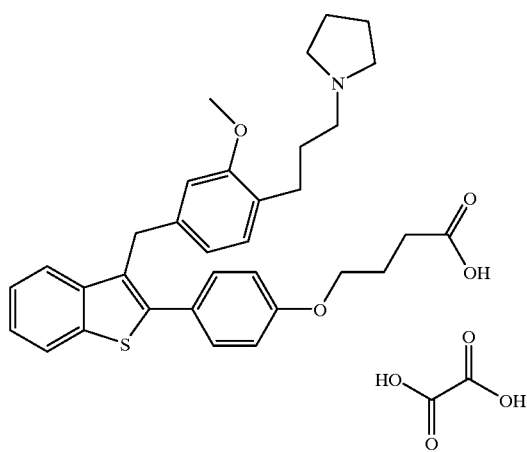

The above ester (Example 16; 0.53 g, 0.95 mmol) was added to a mixture of 50 mL THF, 20 mL EtOH and 4 mL 1 N NaOH. The reaction was stirred 18 hours, neutralized with 4 mL 1 N HCl and concentrated to dryness. The resulting solid was mixed with 100 mL 50% MeOH in CHCl$_3$ and filtered. The filtrate was concentrated to a solid then redissolved in 100 mL MeOH and converted to its oxalate salt by adding a solution of 85 mg (0.95 mmol) of oxalic acid in 10 mL MeOH. Concentration to dryness gave 586 mg (0.92 mmol, 97%) of a solid.

FDMS 546 (M+1); $^1$H NMR (DMSO-$d_6$) δ 10.6–10.8 (bs, 2H), 7.95–7.91 (m, 1H), 7.6–7.58 (m, 1H), 7.43 (d, 2H). 7.32–7.29 (m, 2H), 7.03 (d, 2H), 6.81–6.85 (m, 2H), 6.5 (d, 2H), 4.21 (t, 2H), 4.19 (s, 2H), 4.0 (t, 2H), 3.65 (s, 3H); 3.5 (m, 2H), 3.2–3.0 (bs, 4H), 2.36 (t, 2H), 1.8–2.0 (m, 6H).

EXAMPLE 18

Preparation of Methyl 4-[2-(Hydroxymethyl)-4-[3-8 4-[2-(1-pyrrolidinyl)ethoxy]benzyl]benzo[b]thiophen-2-yl]phenoxy]butyrate Oxalate Salt

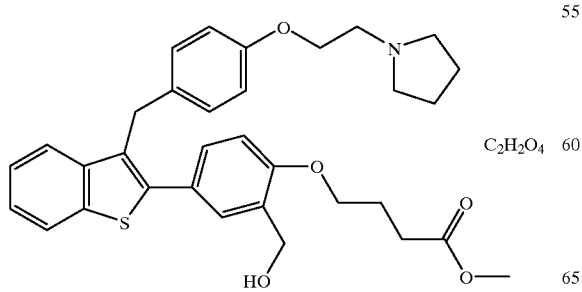

A. 2-[4-Trityloxy-3-(1,3-dioxolan-2-yl)phenyl]benzo[b]thiophene.

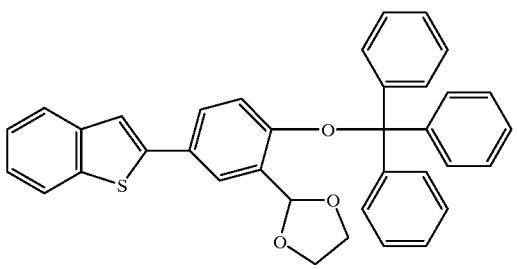

The title compound was prepared in 69% yield by coupling benzo[b]thiophene-2-boronic acid and 2-(5-bromo-2-trityloxyphenyl)-1,3-dioxolane using benzene, tetrakis(triphenylphosphine)palladium(0) and 2.0 N sodium carbonate solution, vigorously stirred at 85° C. Following cooling and addition of brine, the layers were separated and the aqueous layer extracted with EtOAc. After drying and evaporation of the organic phase, the product was purified by chromatography.

FDMS 540 (M$^+$); base peak 243 (M-297); Anal. Calcd for $C_{36}H_{28}O_3S$: C, 79.97; H, 5.22. Found: C, 79.76; H, 5.44.

B. 3-Bromo-2-[4-trityloxy-3-(1,3-dioxolan-2-yl)phenyl]benzo[b]thiophene.

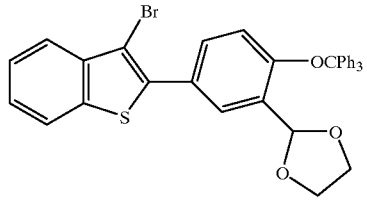

The title compound was prepared from the above benzothiophene in quantitative yield by essentially following the bromination procedure outlined above in Example 3, Part A.

FDMS 620 (M$^+$); Anal. calcd for $C_{36}H_{27}BrO_3S$·0.11CCl$_4$: C, 68.14; H, 4.28. Found: C, 68.14; H, 4.31.

C. 2-[4-Trityloxy-3-(1,3-dioxolan-2-yl)phenyl]benzo[b]thiophene-3-carboxaldehyde.

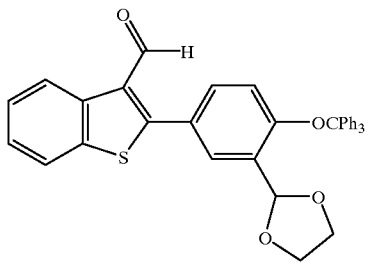

3-Bromo-2-[4-trityloxy-3-(1,3-dioxolan-2-yl)phenyl]benzo[b]thiophene (Part B; 28.7 g, 46.2 mmol) was dissolved in 300 mL of freshly distilled THF and cooled to −78° C. To the solution was added 1.6 M n-BuLi in hexanes (34.7 mL, 55.5 mmol) dropwise over a period of 1 h. The dark brown solution was stirred at −78° C. for 1.5 h. Dry DMF (14.3 mL, 185 mmol) was then added dropwise over 20 min and the reaction mixture was slowly warmed to room temperature and stirred for 19 h. The reaction was quenched with 300 mL of satd NH$_4$Cl solution. The mixture was extracted (3×1 L) with EtOAc. The combined organic layers were dried over Na$_2$SO$_4$ and concentrated under reduced pressure. Purification by column chromatography on the PrepLC (silica gel, 0% to 6% to 10% EtOAc-Hexanes) afforded 6.70 g (11.8 mmol, 25%) of a white foam.

FDMS 243 (M-325); 325 (M-243); Anal. Calcd for C$_{37}$H$_{28}$O$_4$S.0.15CH$_2$Cl$_2$: C, 76.74; H, 4.91. Found: C, 76.69; H, 5.15.

D. 2-[4-Trityloxy-3-(1,3-dioxolan-2-yl)phenyl]-α-[4-[2-(1-pyrrolidinyl)ethoxy]phenyl]benzo[b]thiophene-3-methanol.

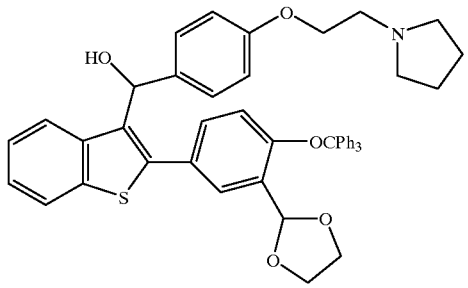

The title compound was prepared in 77% yield by treating 2-[4-trityloxy-3-(1,3-dioxolan-2-yl)phenyl]benzo[b]thiophene-3-carboxaldehyde (Part C) with 4-[2-(1-pyrrolidinyl)ethoxy]phenyl magnesium bromide in THF at 0° C. The reaction was quenched at 0° C. with saturated aqueous NH$_4$Cl solution and extracted with EtOAc. The combined organic layers were dried (MgSO$_4$), evaporated and purified by flash chromatography.

$^1$HNMR (CDCl$_3$) δ 7.75 (d, J=7.8 Hz, 1H), 7.66 (d, J=7.7 Hz, 1H), 7.58 (d, J=2.3 Hz, 1H), 7.49 (d, J=7.1 Hz, 6H), 7.14–7.31 (m, 12H), 6.89–6.99 (m, 2H), 6.81 (d, J=8.7 Hz, 2H), 6.45 (d, J=8.6 Hz, 1H), 6.27 (s, 1H), 6.05 (s, 1H), 4.24 (t, J=5.3 Hz, 2H), 3.99 (m, 4H), 3.12 (dist t, 2H), 2.96 (m, 4H), 1.94 (m, 4H); FDMS 760 (M$^+$) base peak 243 (M-517).

E. 2-[4-Hydroxy-3-(1,3-dioxolan-2-yl)phenyl]-α-[4-[2-(1-pyrrolidinyl)ethoxy]phenyl]benzo[b]thiophene-3-methanol.

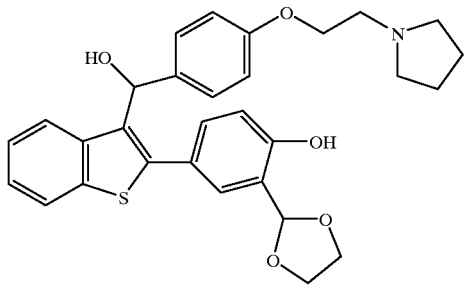

To a solution of (1.74 g, 2.29 mmol) of 2-[4-trityloxy-3-(1,3-dioxolan-2-yl)phenyl]-α-[4-[2-(1-pyrrolidinyl)ethoxy] phenyl]benzo[b]thiophene-3-methanol (Part D) in 23 mL of a THF-EtOH mixture (1:1 ratio) was added (0.50 mL, 4.57 mmol) of anisole followed by addition of 1.75 g of 10% Pd on carbon. The black slurry was stirred at room temperature. under hydrogen (balloon pressure) for 24 h. The slurry was filtered through a pad of diatomaceous earth and rinsed with warm EtOH. The filtrate was concentrated. Purification by flash chromatography (silica gel, 7% to 9%[10% conc NH$_4$OH in MeOH]/CH$_2$Cl$_2$) afforded 954 mg (1.84 mmol, 81%) of a yellow foam.

$^1$HNMR (CDCl$_3$) δ 7.79 (d, J=8.0 Hz, 1H), 7.71 (d, J=7.9 Hz, 1H), 7.40 (d, J=2.2 Hz, 1H), 7.17–7.36 (m, 5H), 6.91 (d, J=8.4 Hz, 1H), 6.82 (d, J=8.6 Hz, 2H), 6.16 (s, 1H), 5.93 (s, 1H), 5.29 (s, 1H), 4.03–4.16 (m, 6H), 2.96 (dist t, 2H), 2.74 (m, 4H), 1.83 (m, 4H); FDMS 517 (M$^+$).

F. Methyl 4-[2-(1,3-Dioxolan-2-yl)-4-[3-[α-hydroxy-4-[2-(1-pyrrolidinyl)ethoxy]benzyl]benzo[b]thiophen-2-yl]phenoxy]butyrate.

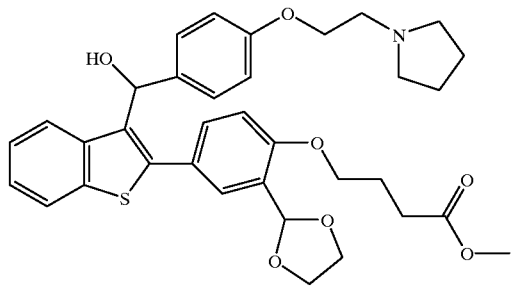

The title compound was prepared in 54% yield by essentially following the procedures outlined in above in Example 1, Part E from the above phenol (Part E) and methyl 4-chlorobutyrate.

FDMS 618 (M$^+$); Anal. calcd for C$_{35}$H$_{39}$NO$_7$S: C, 68.05; H, 6.36; N, 2.27. Found: C, 68.28; H, 6.58; N, 2.43.

G. Methyl 4-[2-(Hydroxymethyl)-4-[3-[4-[2-(1-pyrrolidinyl)ethoxy]benzyl]benzo[b]thiophen-2-yl]phenoxy]butyrate.

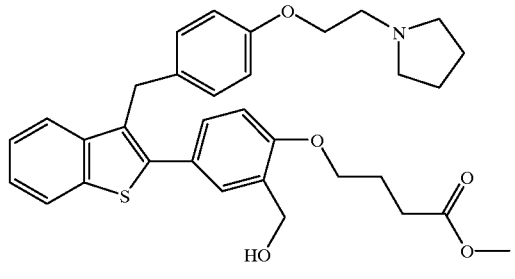

The title compound was prepared in 25% yield from methyl 4-[2-(1,3-dioxolan-2-yl)-4-[3-[α-hydroxy-4-[2-(1-pyrrolidinyl)ethoxy]benzyl]benzo[b]thiophen-2-yl]phenoxy]butyrate (Part F) by essentially following the procedures outlined above in the second part of Example 8, Part B.

FDMS 560 (M$^+$); Anal. Calcd for C$_{33}$H$_{37}$NO$_5$S.0.75CH$_2$Cl$_2$: C, 65.02; H, 6.22; N, 2.25. Found: C, 65.03; H, 6.40; N, 2.39.

H. Methyl 4-[2-(Hydroxymethyl)-4-[3-[4-[2-(1-pyrrolidinyl)ethoxy]benzyl]benzo[b]thiophen-2-yl]phenoxy]butyrate Oxalate Salt.

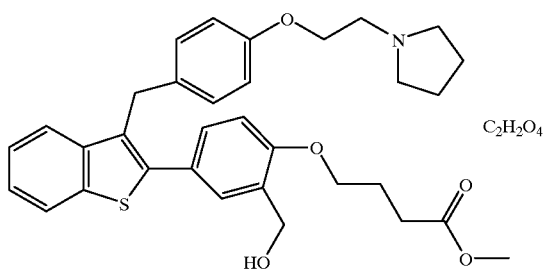

The salt was prepared from the above ester (Part G) in 91% yield by treatment of a solution the ester in EtOAc with a solution of oxalic acid (2+ molar equivalents) in EtOAc, and filtration and drying of the resulting precipitate.

FDMS 559 (M$^+$); Anal. calcd for $C_{33}H_{37}NO_5S \cdot 1.0C_2H_2O_4$: C, 64.70; H, 6.05; N, 2.16. Found: C, 64.56; H, 6.28; N, 2.07.

EXAMPLE 19

Preparation of Methyl 4-[2-Formyl-4-[3-[4-[2-(1-pyrrolidinyl)ethoxy]benzyl]benzo[b]thiophen-2-yl]phenoxy]butyrate Oxalate Salt

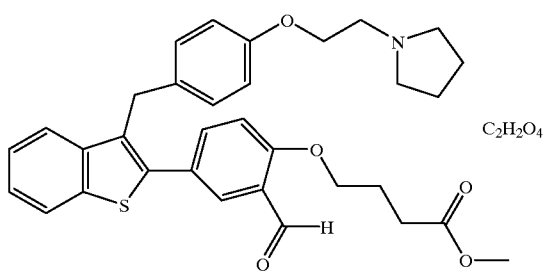

A. Methyl 4-[2-Formyl-4-[3-[α-hydroxy-4-[2-(1-pyrrolidinyl)ethoxy]benzyl]benzo[b]thiophen-2-yl]phenoxy]butyrate.

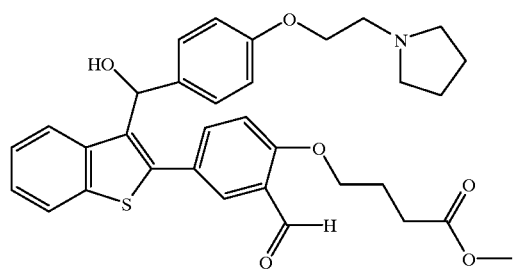

A solution of methyl 4-[2-(1,3-dioxolan-2-yl)-4-[3-[α-hydroxy-4-[2-(1-pyrrolidinyl)ethoxy]benzyl]benzo[b]thiophen-2-yl]phenoxy]butyrate (Example 18, Part F; 160 mg, 0.259 mmol) in 2.6 mL of AcOH/H$_2$O mixture (4:1 ratio) was stirred at room temperature for 1 h 40 min. The reaction mixture was then concentrated under reduced pressure and azeotroped with benzene to afford 149 mg (0.259 mmol, quantitative yield) of an off-white foam.

FDMS 573 (M$^+$); Anal. calcd for $C_{33}H_{35}NO_6S$: C, 69.09; H, 6.15; N, 2.44. Found: C, 68.84; H, 5.91; N, 2.57.

B. Methyl 4-[2-Formyl-4-[3-[4-[2-(1-pyrrolidinyl)ethoxy]benzyl]benzo[b]thiophen-2-yl]phenoxy]butyrate.

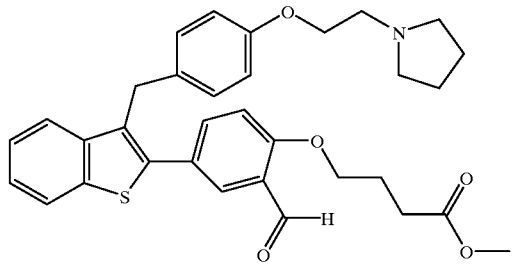

The title compound was prepared in 79% yield by essentially following the procedures outlined above in the second part of Example 8, Part B (except the reaction was quenched after 1 min.) from the above carbinol (Part A).

FDMS 558 (M$^+$); Anal. calcd for $C_{33}H_{35}NO_5S$: C, 71.07; H, 6.33; N, 2.51. Found: C, 70.79; H, 6.32; N, 2.22.

C. Methyl 4-[2-Formyl-4-[3-[4-[2-(1-pyrrolidinyl)ethoxy]benzyl]benzo[b]thiophen-2-yl]phenoxy]butyrate Oxalate Salt.

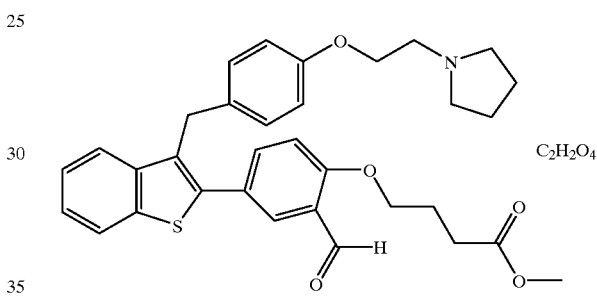

The title compound was prepared in 87% yield by essentially following the procedures outlined above in Example 18, Part H from the above ester (Part B).

FDMS 557 (M$^+$); Anal. Calcd for $C_{33}H_{35}NO_5S \cdot 0.78C_2H_2O_4$: C, 66.11; H, 5.87; N, 2.23. Found: C, 66.09; H, 5.95; N, 2.19.

EXAMPLE 20

Preparation of (S)-6-Hydroxy-3-[3-methoxy-4-[(2-ethoxycarbonyl-5-oxopyrrolidin-1-yl)methyl]benzyl]-2-[4-[2-(1-pyrrolidinyl)ethoxy]phenyl]benzo[b]thiophene

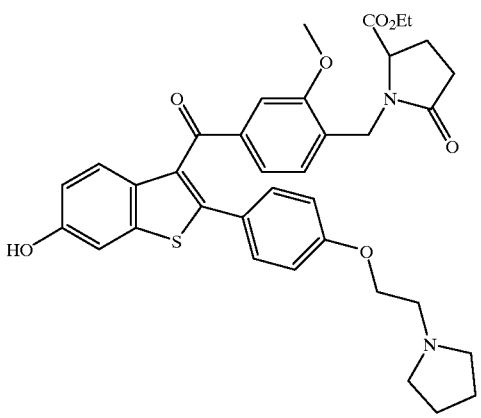

51

A. 1-Bromo-4-[2-(t-butyldimethylsilyloxy)ethoxy]benzene.

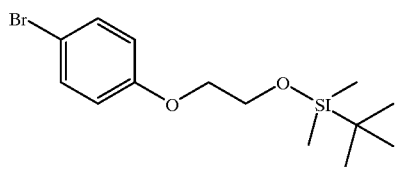

To a solution of 2-(4-bromophenoxy)ethanol (10.94 g, 50.4 mmol), in dry DMF (50 mL), was added t-butyldimethylsilyl chloride (7.6 g, 50.4 mmol) and imidazole (3.77 g, 55.5 mmol). The reaction was stirred at ambient temperature for 18 h, then partitioned with hexane (300 mL) and water (300 mL). The aqueous layer was extracted with hexane (3×100 mL). The combined organic extracts were dried (MgSO$_4$) and the solvent removed under reduced pressure to give the desired product as an oil (16.6 g, 99%).

$^1$H NMR (CDCl$_3$) δ 7.37 (d, J=8.6 Hz, 2H), 6.80 (d, J=8.6 Hz, 2H), 4.00 (t, J=6.0 Hz, 2H), 3.98 (t, J=6.0 Hz, 2H), 0.91 (s, 6H), 0.10 (s, 9H).

B. 6-Benzyloxy-2-[4-[2-(t-butyldimethylsilyloxy)ethoxy]phenyl]benzo[b]thiophen-3-yl 3-Methoxy-4-[(1-pyrrolidinyl)methyl]phenyl Ketone.

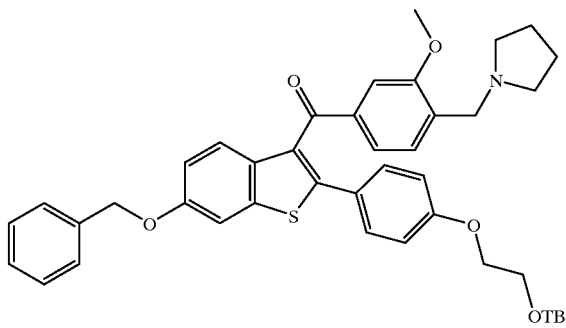

The above bromide (1.25 g, 3.39 mmol), in THF (1.5 mL), was added to a mixture of THF (1.5 mL) and Mg°. The material was stirred at 60° C. for 1 h, during which time the Mg° dissolved. This solution was then added, via syringe, to a THF (5 mL) solution of 6-benzyloxy-2-(dimethylamino)benzo[b]thiophen-3-yl 3-methoxy-4-(1-pyrrolidinylmethyl)phenyl ketone (1.1 g, 2.26 mmol). After 1 h, the solution was diluted 25 fold with EtOAc, the organics washed with saturated NH$_4$Cl solution and concentrated under reduced pressure. Material was purified by flash chromatography (SiO$_2$, 10% MeOH in CHCl$_3$); yielding 827 mg (50%).

$^1$H NMR (CDCl$_3$) δ 7.63 (d, J=8.7 Hz, 1H), 7.49 (d, J=4.3 Hz, 2H), 7.21–7.43 (m, 8H), 7.15 (dd, J=2.1, 8.7 Hz, 1H), 6.95 (d, J=6.4 Hz, 1H), 6.75 (d, J=8.7 Hz, 2H), 5.17 (s, 2H), 3.90–4.0 (m, 4H), 3.80 (s, 3H), 3.65 (s, 2H), 2.55 (s, 4H), 1.90 (s, 4H), 0.95 (s, 9H), 0.15 (s, 6H).

52

C. 6-Benzyloxy-2-[4-[2-(t-butyldimethylsilyloxy)ethoxy]phenyl]benzo[b]thiophen-3-yl (S)-3-Methoxy-4-[(2-ethoxycarbonyl-5-oxopyrrolidin-1-yl)methyl]phenyl Ketone.

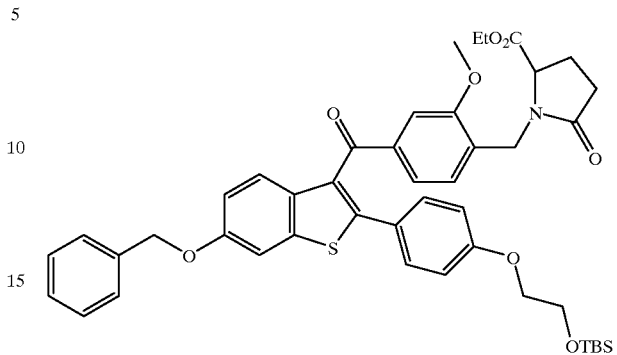

A solution of the above amine (254 mg, 0.359 mmol) in CHCl$_3$ (1 mL) was added to a solution of cyanogen bromide (42 mg, 0.395 mmol) in CHCl$_3$ (1 mL). After completion of the reaction, as indicated by TLC, the mixture was diluted 25 fold with EtOAc, the organics washed with saturated NaHCO$_3$ solution and H$_2$O, and concentrated under reduced pressure. To this crude residue was added the sodium salt of L-pyroglutamic acid ethyl ester (281 mg, 1.79 mmol, preformed from an equimolar amount of NaH in 1 mL of THF) and the mixture stirred at 60° C. for 35 min. After diluting 25 fold with EtOAc, the organics were washed with saturated NaHCO$_3$ solution, H$_2$O, and concentrated under reduced pressure. Material was purified by flash chromatography (SiO$_2$, 20% Hexane in EtOAc); yielding the title compound in 81% yield from the amine.

$^1$H NMR (CDCl$_3$) δ 7.58 (d, J=8.9 Hz, 1H), 7.21–7.46 (m, 10H), 7.05 (dd, J=1.7, 6.5 Hz, 2H), 6.74 (d, J=8.8 Hz, 2H), 5.13 (s, 2H), 4.45 (q, J=15.0, 20.5 Hz, 2H), 4.15 (m, 2H), 3.89–3.98 (m, 4H), 3.82 (dd, J=3.5, 9.1 Hz, 1H), 3.74 (s, 3H), 1.98–2.51 (m, 4H), 1.22 (t, J=7.0 Hz, 3H), 0.88 (s, 9H), 0.06 (s, 6H); FDMS 793.7.

D. 6-Benzyloxy-2-[4-[2-(1-imidazolyl)ethoxy]pheny]benzo[b]thiophen-3-yl (S)-3-Methoxy-4-[(2-ethoxycarbonyl-5-oxopyrrolidin-1-yl)methyl]phenyl Ketone.

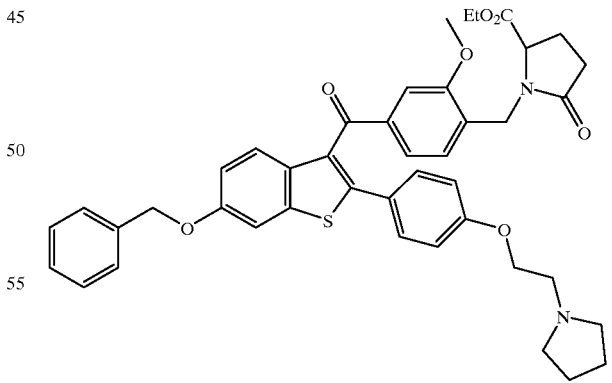

To the above silyl ether (218 mg, 279 mmol) in THF (1 mL) was added 1.0 M TBAF (0.28 mL, 0.28 mmol) and the mixture stirred at room temperature for 45 min. After diluting 50 fold with EtOAc, the organics were washed with H$_2$O and concentrated under reduced pressure. The resulting residue was purified by flash chromatography (SiO$_2$, 5% MeOH in EtOAc). This compound was then taken up in pyridine (0.5 mL) and methanesulfonyl chloride (47 mg, 0.418 mmol) added. The mixture was stirred, under $N_2$, for 35 min and then pyrrolidine (388 mg, 5.58 mmol) added and the solution heated at 60° C. for 45 min. After cooling, the mixture was diluted 50 fold with EtOAc and the organics washed with saturated $NaHCO_3$ and $H_2O$ and concentrated under reduced pressure. Material was purified by flash chromatography ($SiO_2$, 15% MeOH in EtOAc, 1% $Et_3N$ v/v added); yielding the title compound in 83% yield from the silyl ether.

$^1$H NMR ($CDCl_3$) δ 7.58 (d, J=8.9 Hz, 1H), 7.21–7.46 (m, 10H), 7.05 (dd, J=1.8, 9.0 Hz, 2H), 6.75 (d, J=8.7 Hz, 2H), 5.13 (s, 2H), 4.43 (q, J=15.1, 19.1 Hz, 2H), 4.01 4.16 (m, 4H), 3.85 (dd, J=3.4, 9.0 Hz, 1H), 3.74 (s, 3H), 2.84 (t, J=5.9 Hz, 2H), 2.58 (s, 4H), 1.81–2.57 (m, 4H), 1.78 (s, 4H), 1.22 (t, J=7.3 Hz, 3H); FDMS 733 (M+).

E. (S)-6-Hydroxy-3-[3-methoxy-4-[(2-ethoxycarbonyl-5-oxopyrrolidin-1-yl)methyl]benzyl]-2-[4-[2-(1-pyrrolidinyl)ethoxy]phenyl]benzo[b]thiophene.

To the above benzyl ether (74 mg, 0.101 mmol) was added aqueous ammonium formate (1 mL of 25% w/v), THF (1 mL), and Pd/C (10%, 74 mg). The mixture was rapidly stirred at room temperature for 2 h and then diluted 25 fold with THF and passed through a pad of diatomaceous earth. The filtrate was concentrated under reduced pressure and the resulting residue purified by flash chromatography ($SiO_2$, 10% MeOH in $CHCl_3$).

$^1$H NMR ($CDCl_3$) δ 7.54 (d, J=9.4 Hz, 1H), 7.01–7.31 (m, 4H0, 7.00 (d, J=7.8 Hz, 1H), 6.88 (d, J=2.3 Hz, 1H), 6.85 (s, 1H), 6.57 (d, J=8.7 Hz, 2H), 4.40 (q, J=15.1, 21.3 Hz, 2H), 4.05–4.16 (m, 4H), 3.81 (dd, J=3.2, 8.8 Hz, 1H), 3.71 (s, 3H), 2.96 (s, 2H), 2.82 (s, 4H), 1.98–2.51 (m, 4H), 1.87 (s, 4H), 1.22 (t, J=4.2 Hz, 3H); FAB MS 643.2 (M+1).

EXAMPLE 21

Preparation of (S)-6-Hydroxy-3-[3-methoxy-4-[(2-carboxy-5-oxopyrrolidin-1-yl)methyl]benzyl]-2-[4-[2-(1-pyrrolidinyl)ethoxy]phenyl]benzo[b]thiophene Hydrochloride

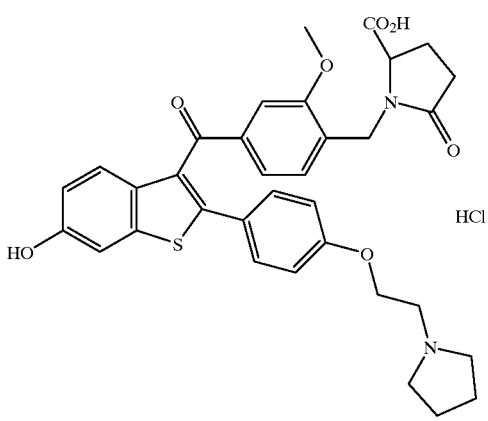

To the above ester (Example 20, Part E; 42 mg, 0.065 mmol) was added NaOH (5 mg, 0.130 mmol) and EtOH (95%, 0.5 mL) and the mixture stirred at room temperature for 2 h. After concentrating under reduced pressure, the salt was taken up in $H_2O$ (5 mL) and the pH lowered to 3 by addition of 6 N HCl and reconcentrated. The material was then purified by semi-preparative HPLC, using a (VYDAC) C18 column (25×250 mm), and following a gradient elution 98:2 ($H_2O$ with 0.1% HCl added/$CH_3CN$) to 50:50. This yielded 40 mg (94%) of the title compound.

$^1$H NMR ($CD_3OD$) δ 7.52 (d, J=7.8 Hz, 1H), 7.25–7.30 (m, 4H), 7.18 (d, J=6.7 Hz, 1H), 7.02 (d, J=7.8 Hz, 1H), 6.84–6.91 (m, 3H), 4.38 (q, J=15.1, 197 Hz, 2H), 4.27 (s, 2H), 3.84 (dd, J=2.8, 8.6 Hz, 1H), 3.72 (s, 3H), 3.68 (s, 2H), 3.61 (s, 2H), 3.18–3.20 (m, 2H), 2.03–2.43 (m, 8H); FAB MS 615 (M+1).

EXAMPLE 22

Preparation of 2-[4-[2-(Hydroxy)ethoxy]phenyl]-3-[4-[2-(1-pyrrolidinyl)ethoxy]benzyl]benzo[b]thiophene Oxalate

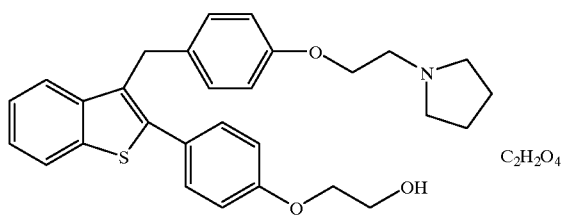

A. 2-[4-[2-(tert-Butyldiphenylsilyloxy)ethoxy]phenyl]-3-[4-[2-(1-pyrrolidinyl)ethoxy]benzyl]benzo[b]thiophene.

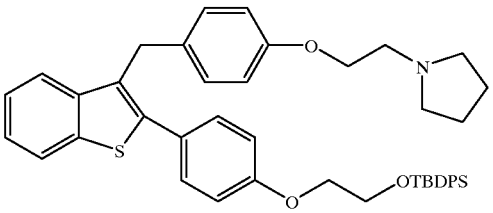

A mixture of 2.00 g (4.66 mmol) of 2-(4-hydroxyphenyl)-3-[4-[2-(1-pyrrolidinyl)ethoxy]benzyl]benzo[b]thiophene (Example 8, Part C), 1.86 g (5.12 mmol) of 1-bromo-2-(tert-butyldiphenylsilyloxy)ethane, and 1.93 g (14.0 mmol) of $K_2CO_3$ in 50 mL DMF was heated to 50° C. for 22 h. The reaction was poured into 250 mL of $H_2O$ and the mixture extracted with EtOAc (3×100 mL). The combined organic extracts were washed with $H_2O$ (2×100 mL), dried over $K_2CO_3$, filtered and concentrated in vacuo to give 4.21 g of an oily solid. Purification by flash chromatography ($SiO_2$; 0.1% then 0.2% then 0.5% MeOH in $CHCl_3$ sat'd with $NH_4OH$) afforded 2.76 g (3.88 mmol; 83%) of the title compound as an oil.

FDMS 711 (M+); Anal. calcd for $C_{45}H_{49}NO_3S$: C, 75.91; H, 6.94; N, 1.97. Found: C, 76.05; H, 6.98; N, 2.12.

B. 2-[4-[2-(Hydroxy)ethoxy]phenyl]-3-[4-[2-(1-pyrrolidinyl)ethoxy]benzyl]benzo[b]thiophene Oxalate.

By essentially following the conditions described in Example 20, Part A, for the removal of the protecting group, the title compound was prepared as a solid from the above silyl ether in 93% yield following flash chromatography ($SiO_2$; 2% then 4% MeOH in $CHCl_3$ sat'd with $NH_4OH$).

FDMS 473 (M+); Anal. calcd for $C_{29}H_{31}NO_3S \cdot C_2H_2O_4$: C, 66.06; H, 5.91; N, 2.49. Found: C, 65.88; H, 5.68; N, 2.58.

EXAMPLE 23

Preparation of 6-Hydroxy-2-[4-(2-hydroxyethoxy)phenyl]benzo[b]thiophen-3-yl 3-Methoxy-4-[(4-morpholinyl)methyl]phenyl Ketone Oxalate

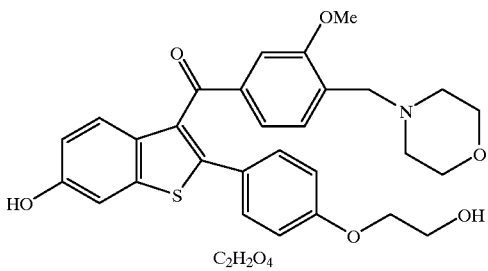

$C_2H_2O_4$

A. 2-(4-Bromophenoxy)ethyl Triisopropylsilyl Ether.

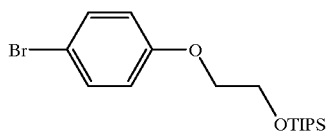

Triisopropylsilyl trifluoromethanesulfonate (24.4 mL, 90.7 mmol) was added to a stirred solution of 2-(4-bromophenoxy)ethanol (15.1 g, 69.8 mmol) and anhydrous triethylamine (19.4 mL, 140 mmol) in anhydrous $CH_2Cl_2$ (30 mL) at 0° C. under nitrogen atmosphere. The resultant mixture was stirred for 1 h. The mixture was washed with saturated $NaHCO_3$ (25 mL), extracted with EtOAc (3×75 mL), dried over $MgSO_4$, filtered, concentrated, and chromatographed on silica (10% $CH_2Cl_2$ in hexanes) to give 23.4 g (90%) of the silyl ether as a colorless liquid.

IR (thin film) 2944, 1489 $cm^{-1}$; FDMS m/e 372 ($M^+$, $^{79}Br$) and 374 ($M^+$, $^{81}Br$). Anal. Calcd. for $C_{17}H_{29}BrO_2Si$: C, 54.68; H, 7.83. Found: C, 54.97; H, 7.55.

B. 6-Benzyloxy-2-[4-[2-(hydroxy)ethoxy]phenyl]benzo[b]thiophen-3-yl 3-Methoxy-4-[(4-morpholinyl)methyl]phenyl Ketone.

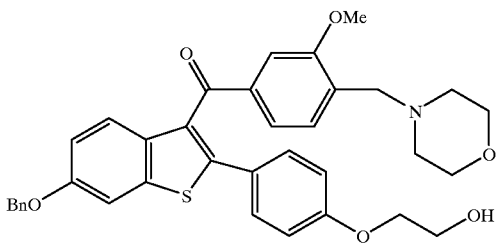

The above silyl ether (2.71 g, 7.26 mmol) was added to a stirred suspension of magnesium ribbons (164 mg, 6.77 mmol) in anhydrous THF (4 mL) under argon atmosphere, followed by the addition of a small iodine chip. The resultant mixture was heated in an oil bath at 60–65° C. for 1.5 h to form a homogeneous Grignard solution. The Grignard solution was cooled to room temperature and diluted with anhydrous THF (10 mL) before it was added to a stirred solution of 6-benzyloxy-2-(dimethylamino)benzo[b]thiophen-3-yl 3-methoxy-4-[(4-morpholinyl)methyl]phenyl ketone (2.50 g, 4.84 mmol) in anhydrous THF (10 mL) at 0° C. under argon atmosphere. The resultant mixture was stirred at 0° C. for 1.5 h, then quenched with saturated aqueous $NH_4Cl$ (15 mL). After extraction with EtOAc (70 mL×2), the combined organic layers were dried over $MgSO_4$, filtered, and concentrated to give a gummy residue which was dissolved in anhydrous THF (25 mL) and treated with tetrabutylammonium fluoride (5.80 mL, 1 M in THF) at room temperature under nitrogen atmosphere. After stirring for 1 h, the mixture was concentrated under vacuum; the residue was chromatographed on silica [gradient 0–30% MeOH/$Et_3N$ (2/1) in EtOAc] to give 2.61 g (88%) of the keto alcohol as a foam.

IR (neat) 3426 (br), 1646, 1605 $cm^{-1}$; FDMS m/e 609 ($M^+$); Anal. Calcd. for $C_{36}H_{35}NO_6S$: C, 70.91; H, 5.79; N, 2.30. Found: C, 70.63; H, 5.65; N, 2.04.

C. 6-Hydroxy-2-[4-(2-hydroxyethoxy)phenyl]benzo[b]thiophen-3-yl 3-Methoxy-4-[(4-morpholinyl)methyl]phenyl Ketone Oxalate.

Using a debenzylation procedure similar to that described above in Example 20, Part E, followed by formation of the oxalate using a procedure similar to that described above in Example 18, part H, the title diol was obtained from the above benzyloxy alcohol as a yellow solid in an overall 50% yield.

IR (KBr) 3420 (br), 3350–2250 (br), 1640, 1607 $cm^{-1}$; FABMS m/e 520 ($M^+$+1-1[$C_2H_2O_4$]); Anal. Calcd. for $C_{29}H_{29}NO_6S \cdot C_2H_2O_4$: C, 61.07; H, 5.13; N, 2.30. Found: C, 61.12; H, 5.21; N, 2.16.

EXAMPLE 24

Preparation of 3-Methoxy-4-[(5-tetrazolyl)methyl]phenyl 2-[4-[2-(1-Pyrrolidinyl)ethoxy]phenyl]benzo[b]thiophen-3-yl Ketone Oxalate

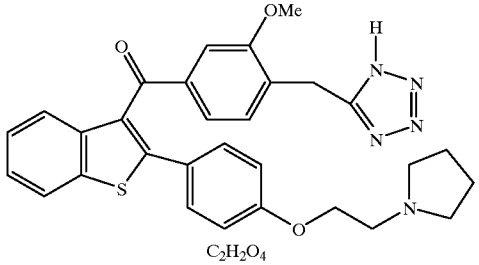

$C_2H_2O_4$

A. Methyl 4-Cyanomethyl-3-methoxybenzoate.

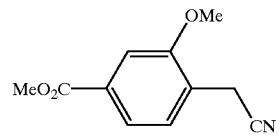

AIBN (274 mg) was added to a stirred suspension of methyl 3-methoxy-4-methylbenzoate (20.10 g, 112.0 mmol) and NBS (23.84 g, 134 mmol) in $CCl_4$ (730 mL), and the resultant mixture was heated to reflux for 3 h. At room temperature, the mixture was diluted with hexanes (350 mL) before it was filtered and concentrated to give 28.59 g (crude yield 99%) of the brominated product.

Part of the crude brominated product (8.10 g) was dissolved in anhydrous THF (70 mL). 18-Crown-6 (413 mg, 1.56 mmol) was added followed by KCN (3.05 g, 46.9 mmol); then the resulting mixture was heated at 65° C. for 20 h. The reaction mixture was diluted with $H_2O$ (50 mL) and EtOAc (250 mL), then the aqueous layer was extracted with EtOAc (2×100 mL). The combined organic layers were dried over $MgSO_4$, filtered, and concentrated to give an oily residue, which was chromatographed on silica [gradient 5–20% EtOAc in hexanes] to provide 2.50 g of the cyanomethyl compound (39%) as a white solid.

IR (KBr) 2260, 1714, cm$^{-1}$; FDMS m/e 205 (M$^+$).

B. 4-Cyanomethyl-3-methoxybenzoyl Chloride.

Using procedures similar to those described above in Example 1, Part C, the above benzoate was hydrolyzed and converted into the corresponding benzoyl chloride.

C. 4-Cyanomethyl-3-methoxyphenyl 2-(4-[2-(1-Pyrrolidinyl)ethoxy]phenyl]benzo[b]thiophen-3-yl Ketone.

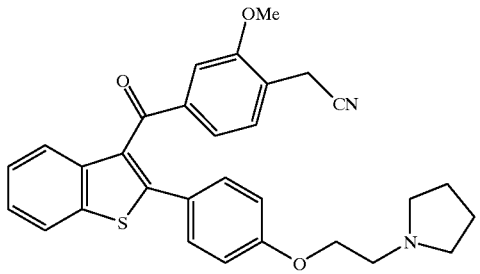

Following a procedure similar to that described in Example 1, Part C, the ketone was obtained from the above benzoyl chloride and 2-[4-[2-(1-pyrrolidinyl)ethoxy] phenyl]benzo[b]thiophene (obtained by coupling benzo[b] thiophene-2-boric acid and 4-[2-(1-pyrrolidinyl)ethoxy]-1-bromobenzene using a procedure similar to that of Example 18, Part A). Column chromatography on silica [gradient 60–90% THF in hexanes] gave 190 mg (41%) of the ketone as a yellow oil.

IR (thin film) 2965, 2256, 1651, 1606 cm$^{-1}$; FDMS m/e 497 (M$^+$+1); Anal. Calcd. for $C_{30}H_{28}N_2O_3S$: C, 72.56; H, 5.68; N, 5.64. Found: C, 72.72; H, 5.93; N, 5.60.

D. 3-Methoxy-4-[(5-tetrazolyl)methyl]phenyl 2-[4-[2-(1-Pyrrolidinyl)ethoxy]phenyl]benzo[b]thiophen-3-yl Ketone Oxalate.

Acetic acid (0.055 mL, 0.957 mmol) and sodium azide (62.2 mg, 0.957 mmol) were sequentially added to a stirred solution of the above nitrile (190 mg, 0.383 mmol) in n-BuOH (0.4 mL) at room temperature under nitrogen atmosphere. The mixture was heated to 90° C. and stirred for 16 h. The reaction mixture was allowed to cool to room temperature and without workup the reaction mixture was chromatographed on silica [gradient 0–10% MeOH in CH$_2$Cl$_2$] to give 30.1 mg (15%) of a gum. Following a procedure similar to that described in Example 18, Part H, the title compound was obtained from the gum as a beige solid in 86% yield.

IR (KBr) 3450 (br), 2800–2200 (br), 1731, 1646, 1605 cm$^{-1}$; FABMS m/e 540 (M$^+$+1−1[C$_2$H$_2$O$_4$]).

EXAMPLE 25

Preparation of 3-[3-Methoxy-4-[(5-tetrazolyl) methyl]benzyl]-2-[4-[2-(1-pyrrolidinyl)ethoxy] phenyl]benzo[b]thiophene Oxalate

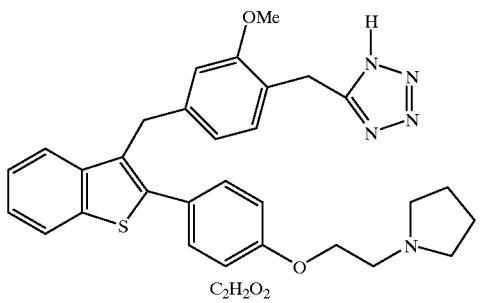

A. 3-Methoxy-4-[[1-(triphenylmethyl)tetrazol-5-yl]methyl] phenyl 2-[4-[2-(1-Pyrrolidinyl)ethoxy]phenyl]benzo[b]thiophen-3-yl Ketone.

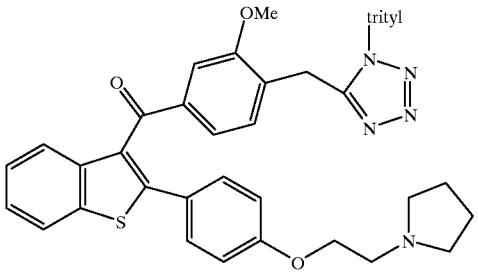

Trimethyltin azide (288 mg, 1.39 mmol) was added to a stirred solution of the nitrile of Example 24, Part C, (434 mg, 0.874 mmol) in 1 mL anhydrous toluene, at room temperature, under a nitrogen atmosphere. The resulting mixture was refluxed for 17 h, then cooled to room temperature and 5N NaOH (0.29 mL, 1.39 mmol) was added causing the mixture to solidify. THF (3 mL) was added and the mixture was manually stirred for about 20 min, then tritylbromide (480 mg, 1.49 mmol) was added at room temperature and stirred for 2.5 h. The resulting mixture was diluted with 5 mL H$_2$O and 25 mL EtOAc. The mixture was then washed with a saturated solution of NaHCO$_3$ and the aqueous layer was extracted with EtOAc (2×15 mL). The organics were dried over MgSO$_4$, filtered, concentrated, and chromatographed on silica [gradient 0–10% EtOH/Et$_3$N (2/1) 10–30% THF in hexanes] to give 400 mg (59%) of the protected keto tetrazole as a yellow oil.

IR (Thin film) 2927 (br), 1654, 1606 cm$^{-1}$; FDMS m/e 782 (M$^+$+1).

B. 3-[3-Methoxy-4-[(5-tetrazolyl)methyl]benzyl]-2-[4-[2-(1-pyrrolidinyl)ethoxy]phenyl]benzo[b]thiophene.

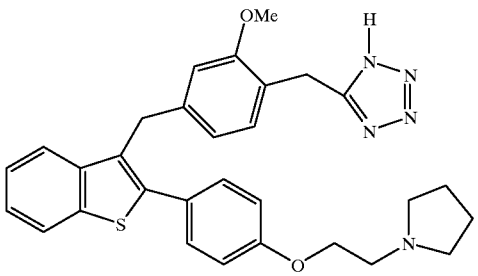

DIBAL-H (0.48 mL, 1 M in toluene) was added to a stirred solution of the above ketone (151 mg, 0.192 mmol) in anhydrous CH$_2$Cl$_2$ (2 mL) at −15° C. under a nitrogen atmosphere. The resultant solution was stirred at −15° C. for 1.5 h. The reaction mixture was treated sequentially with MeOH (1.0 mL), diluted with EtOAc (10 mL), and saturated aqueous Rochelle's salt solution (10 mL). The two-layered solution was stirred vigorously at room temperature for 1 h. After extraction with EtOAc (2×10 mL), the organic layer was dried over MgSO$_4$, filtered, concentrated, and chromatographed on silica to give 47 mg (31%) of the desired alcohol.

The above alcohol was dissolved in anhydrous CH$_2$Cl$_2$ (1 mL) and cooled to 0° C. before it was sequentially treated with TFA (0.056 mL, 0.721 mmol) and Et$_3$SiH (0.067 mL, 0.421 mmol). The resultant mixture was stirred at 0° C. for 1 h. After cautious treatment with saturated aqueous NaHCO$_3$ to neutralize TFA, the mixture was allowed to warm to room temperature where it was extracted with EtOAc (3×5 mL). The combined organic layers were dried over MgSO$_4$, filtered, concentrated to give the methylene compound as a crude gummy residue.

C. 3-[3-Methoxy-4-[(5-tetrazolyl)methyl]benzyl]-2-[4-[2-(1-pyrrolidinyl)ethoxy]phenyl]benzo[b]thiophene Oxalate.

The crude product from Part B, above, was dissolved in THF (1 mL), and the solution was stirred and treated with a solution of oxalic acid (8.1 mg) in THF/EtOAc (1 mL/1 mL) to form a suspension. An additional 2 mL of EtOAc was added to the suspension. After filtration and subsequent drying under vacuum at 50° C., 20.1 mg (53%) of the title compound was obtained as a white solid.

$^1$H NMR (DMSO-d$_6$) δ 1.90 (br s, 4H), 3.29 (br s, 4H), 3.52 (br s, 2H), 3.61 (s, 3H), 4.06 (s, 2H), 4.20 (s, 2H), 4.30 (br s, 2H), 6.51 (d, J=7.3 Hz, 1H), 6.80 (s, 1H), 6.97 (d, J=7.3 Hz, 1H), 7.10 (d, J=8.3 Hz, 2H), 7.31 (m, 2H), 7.47 (d, J=8.3 Hz, 2H), 7.58 (m, 1H), 7.93 (m, 1H).

EXAMPLE 26

Preparation of 4-[2-Formyl-4-[3-[4-[2-(1-pyrrolidinyl)ethoxy]benzyl]benzo[b]thiophen-2-yl]phenoxy]butyric Acid Sodium Salt

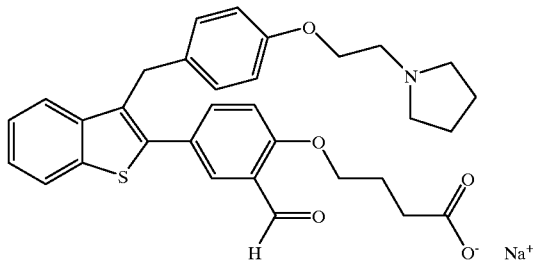

The title compound was prepared by adding 179 µL (0.179 mmol) of 1 N NaOH to a solution of 100 mg (0.179 mmol) methyl 4-[2-formyl-[3-[4-[2-(1-pyrrolidinyl)ethoxy]benzyl]benzo[b]thiophen- 2-yl]phenoxy]]butyrate (Example 19, Part B) dissolved in 1.0 mL of 1:1 THF:MeOH mixture. The solution was stirred at room temperature for 22 h. The reaction mixture was then evaporated in vacuo and dried in a vacuum oven at 55° C. over P$_2$O$_5$ to yield the title compound (101.4 mg, 0.179 mmol, quantitative yield) as a light yellow solid.

mp 214–217° C. (dec); IR (KEr) 3400 (br), 1685, 1607, 1571 cm$^{-1}$; Ion Spray MS 544 (M+1)$^+$; 456 (M-87)$^-$; Anal. Calcd for C$_{32}$H$_{32}$NO$_5$S.Na: C, 67.95; H, 5.70; N, 2.48. Found: C, 68.13; H, 5.94; N, 2.73.

EXAMPLE 27

Preparation of 3-[4-(2-Ethoxy-2-oxoethoxy)benzyl]-2-[4-[2-(1-pyrrolidinyl)ethoxy]phenyl]benzo[b]thiophene Hydrochloride

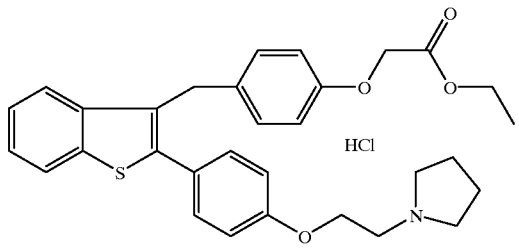

A solution of 3-(4-hydroxybenzyl)-2-[4-[2-(1-pyrrolidinyl)ethoxy]phenyl]benzo[b]thiophene in DMF (70 mL) was treated with sodium hydride (100 mg, 60% in mineral oil, 2.5 mmol) for 10 minutes and then with ethy l bromoacetate (0.3 mL, 2.7 mmol) for 20 minutes. The mixture was diluted with EtOAc and water. The organic phase was washed with water, washed with brine, dried over sodium sulfate, and evaporated in vacuo. The residue was chromatographed on silica gel, eluting with a gradient (0–4% MeOH/CH$_2$Cl$_2$), to give the product free base as an oil (860 mg, 82%). The hydrochloride salt was precipitated from a CH$_2$Cl$_2$-Et$_2$O solution as an amorphous solid.

FDMS m/e 516.1 (M+); Analysis for C$_{31}$H$_{33}$NO$_4$S.HCl: Calcd: C, 67.44; H, 6.21; N, 2.54; Found: C, 67.70; H, 6.23; N, 2.57.

The 3-(4-hydroxybenzyl)-2-[4-[2-(1-pyrrolidinyl)ethoxy]phenyl]benzo[b]thiophene may be obtained as follows.

A. 2-(4-Hydroxyphenyl)benzo[b]thiophen-3-yl 4-Methoxyphenyl Ketone.

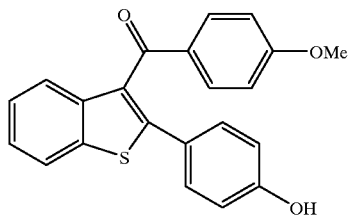

To a solution of 10.0 g (26.7 mmol) of 2-(4-methoxyphenyl)benzo[b]thiophen-3-yl 4-methoxyphenyl ketone in 400 mL of CH$_2$Cl$_2$ at –10° C. was added dropwise 107 mL of a 1.0 M solution of BBr$_3$ in CH$_2$Cl$_2$. After complete addition, the reaction was stirred at –10° C. for 1 h and was quenched by the careful addition of 75 mL of MeOH. The mixture was allowed to warm to room temperature and was stirred at ambient temperature for 2 h. Evaporation of the volatiles in vacuo afforded a deep red oil which was taken up in 250 mL of EtOAc. The solution was then washed sequentially with saturated aq NaHCO$_3$ (2×200 mL), H$_2$O (200 mL) and brine (200 mL), dried over Na$_2$SO$_4$, and concentrated in vacuo to give 9.85 g of a red oil which was purified by flash chromatography (SiO$_2$; 25% EtOAc in hexanes) to afford 8.69 g (24.1 mmol; 90%) of the title compound as a light yellow solid.

FDMS 360 (M$^+$; 100).

B. 2-[4-[2-(1-Pyrrolidinyl)ethoxy]phenyl]benzo[b]thiophen-3-yl 4-Methoxyphenyl Ketone.

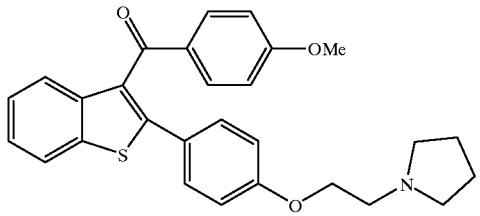

By essentially following the procedure detailed in Example 1, Part E, using 1-(2-chloroethyl)pyrrolidine hydrochloride as the alkylating agent and an extra equivalent of base, the title compound was prepared from 2-(4-hydroxyphenyl)benzo[b]thiophen-3-yl 4-methoxyphenyl ketone (Part A) as an oil in 80% yield following flash chromatography (SiO$_2$; 2.5% MeOH in CH$_2$Cl$_2$).

FDMS 457 (M$^+$; 100); Anal. Calcd for C$_{28}$H$_{27}$NO$_3$S: C, 73.49; H, 5.95; N, 3.06. Found: C, 73.19 ; H, 5.96; N, 3.02.

C. 2-[4-[2-(1-Pyrrolidinyl)ethoxy]phenyl]benzo[b]thiophen-3-yl 4-Hydroxyphenyl Ketone.

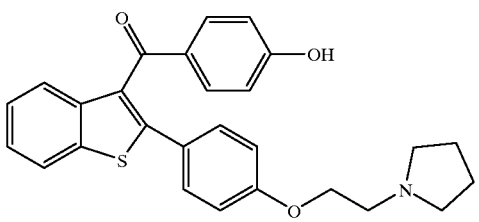

A solution of 1.90 g (4.15 mmol) of 2-[4-[2-(1-pyrrolidinyl)ethoxy]phenyl]benzo[b]thiophen-3-yl 4-methoxyphenyl ketone (Part B) in 50 mL of DMF was treated with 0.7 g (8.30 mmol) of sodium thioethoxide at 80° C. for 1 h. The mixture was cooled, filtered, and concentrated in vacuo. The residue was taken up in 100 mL of $CH_2Cl_2$ and was transferred to a separatory funnel containing 200 mL of $H_2O$. The aqueous layer was adjusted to pH 8 with 5.0 N aq HCl and the contents were shaken well. The two layers were separated and the aqueous layer was extracted with EtOAc. The combined organic layers were dried over $K_2CO_3$ and evaporated to give a yellow solid which was triturated with EtOAc to afford 1.40 g of the title compound as a yellow solid.

FDMS 443 ($M^+$; 100).

D. 3-(4-Hydroxybenzyl)-2-[4-[2-(1-pyrrolidinyl)ethoxy]phenyl]benzo[b]thiophene.

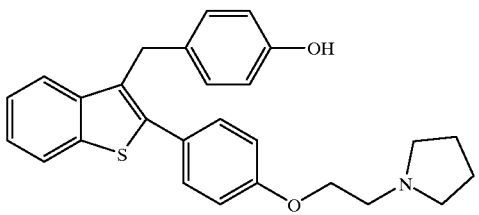

By essentially following the procedures detailed in Example 1, Part D, the title compound was prepared in 51% yield as a white solid.

FDMS 429 ($M^+$; 100).

EXAMPLE 28

Preparation of 3-[4-(2-Methoxy-2-oxoethoxy)benzoyl]-2-[4-[2-(1-pyrrolidinyl)ethoxy]phenyl]benzo[b]thiophene Hydrochloride

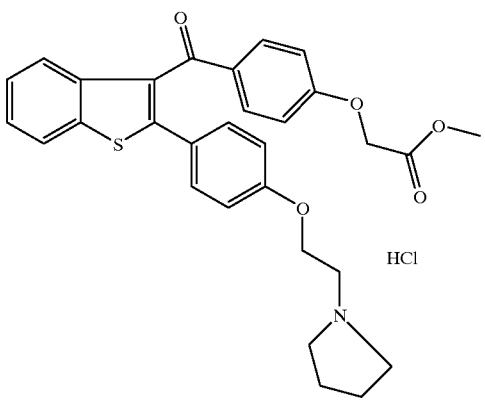

The title compound was prepared following the procedure of Example 27 and utilizing methyl α-bromoacetate and 3-(4-hydroxybenzoyl)-2-[4-[2-(1-pyrrolidinyl)ethoxy]phenyl]benzo[b]thiophene.

FDMS m/e 515 (M+); Analysis for $C_{30}H_{29}NO_5S\cdot HCl$: Calcd: C, 65.27; H, 5.48; N, 2.54; Found: C, 62.82; H, 5.49; N, 2.58.

EXAMPLE 29

Preparation of 3-[4-(2-Hydroxyethoxy)benzyl]-2-[4-[2-(1-pyrrolidinyl)ethoxy]phenyl]benzo[b]thiophene

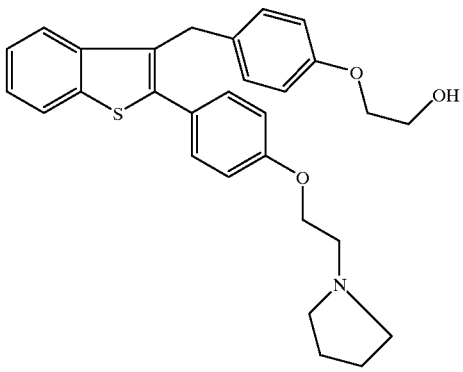

To the product (1 g, 1.94 mmol) of Example 28 dissolved in anhydrous THF (80 mL) was added LAH (0.47 g, 12.4 mmol) at 0–5° C. under nitrogen. The reaction mixture was stirred for 2 hours and quenched with ice-cold NaOH (0.5 M) solution. The organic layer was extracted with ethyl acetate, combined, dried and concentrated in vacuo. To this residue (0.88 g, 1.8 mmol) dissolved in dichloromethane (~50 mL) was added triethylsilane (1.73 mL, 10.8 mmol) and TFA (0.42 mL, 5.4 mmol). The reaction mixture was stirred for 1.5 hours before it was washed with dilute NaOH solution and brine until neutral. The combined organic layers were dried with $Na_2SO_4$ and concentrated. The residue was purified by column chromatography (20% $CH_3OH$ in dichloromethane) to yield 0.53 g (63%) of title compound.

FDMS m/e 474.3 (M+); Analysis for $C_{29}H_{31}NO_3S$: Calcd: C, 73.54; H, 6.60; N, 2.96; Found: C, 71.32; H, 6.29; N, 2.93.

EXAMPLE 30

Preparation of 3-[4-[3-(1H-Tetrazol-5-yl)propyloxy]benzyl]-2-[4-[2-(1-pyrrolidinyl)ethoxy]phenyl]benzo[b]thiophene Trifluoroacetic Acid Salt

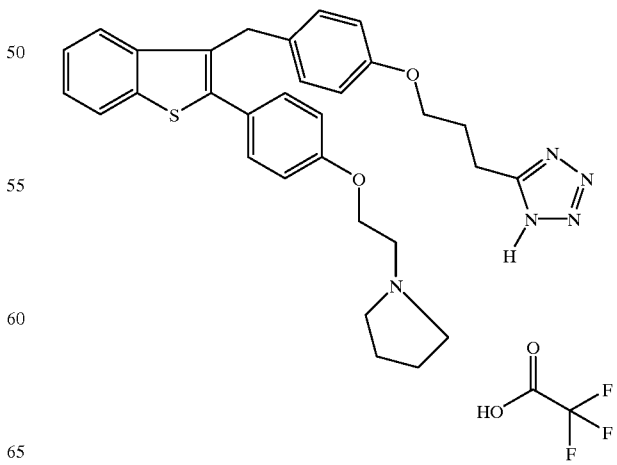

A. 3-[4-(3-Cyanopropyloxy)benzyl]-2-[4-[2-(1-pyrrolidinyl)ethoxy]phenyl]benzo[b]thiophene.

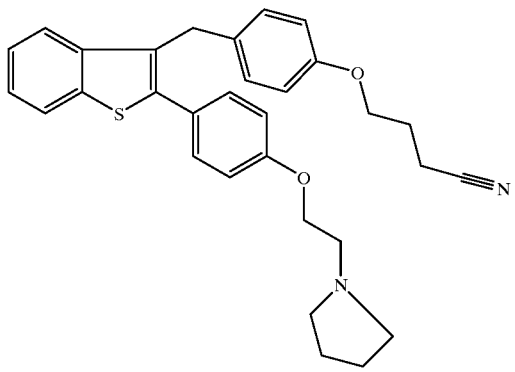

To a stirred solution of 3-(4-hydroxybenzyl)-2-[4-[2-(1-pyrrolidinyl)ethoxy]phenyl]benzo[b]thiophene (0.9 g, 2.09 mmol) in anhydrous DMF (50 mL) was added NaH (0.5 g, 60% in mineral oil, 12.5 mmol) under nitrogen. The resultant mixture was stirred for 10–20 min, followed by the addition of 4-bromobutyronitrile and further stirring for 1.5 hours. The mixture was diluted with EtOAc and ice water. The organic phase was washed with brine, dried with $Na_2SO_4$ and concentrated in vacuum. The resulting crude product was purified on a silica column (5% methanol in $CH_2Cl_2$) to give 0.75 g (62%) of the title compound as a light yellow oil.

B. 3-[4-[3-(1H-Tetrazol-5-yl)propyloxy]benzyl]-2-[4-[2-(1-pyrrolidinyl)ethoxy]phenyl]benzo[b]thiophene Trifluoroacetic Acid Salt.

To a stirred solution of the product from Part A (133 mg, 0.27 mmol) in dichloromethane (20 mL) was added $Bu_3SnN_3$ (1.5 mL, 5.5 mmol). Dichloromethane was removed under reduced pressure and the reaction mixture was stirred under nitrogen at 95° C. overnight. The reaction mixture was cooled to room temperature and diluted with $CH_3CN$ (10–20 mL) and THF (2 mL) and then acidified with HOAc (3 mL). After being stirred for 3.5 hour, the reaction mixture was washed with hexane, concentrated in vacuo, and diluted with EtOAc and brine. The combined organics were dried with $Na_2SO_4$ and concentrated. The residue was purified by reverse phase HPLC (gradient 5–70% TFA in $CH_3CN$) to afford 107 mg (74%) of the TFA salt as a white solid.

FDMS m/e 540.4 (M+); Analysis for $C_{31}H_{33}N_5O_2S \cdot C_2HF_3O_2 \cdot 1.5H_2O$: Calcd: C, 58.31; H, 5.34; N, 10.30; Found: C, 58.21; H, 5.25; N, 10.29.

EXAMPLE 31

Preparation of 3-[4-(3-Methyl-4-methoxy-4-oxobutyloxy)benzyl]-2-[4-[2-(1-pyrrolidinyl)ethoxy]phenyl]benzo[b]thiophene Hydrochloride

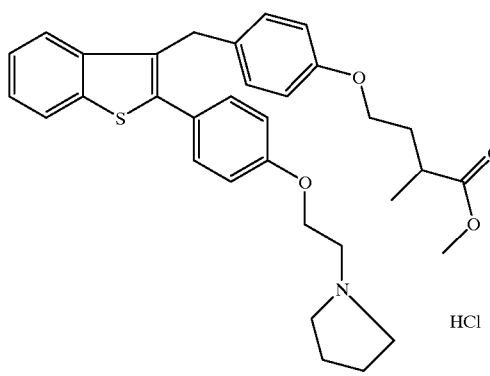

The title compound was prepared following the procedures of Example 27 utilizing methyl 2-methyl-4-bromobutyrate.

FDMS m/e 544 (M+); Analysis for $C_{31}H_{37}NO_4S \cdot HCl$: Calcd: C, 68.32; H, 6.60; N, 2.41; Found: C, 65.47; H, 6.57; N, 2.43.

EXAMPLE 32

Preparation of 3-[4-(3-Methyl-4-hydroxy-4-oxobutyloxy)benzyl]-2-[4-[2-(1-pyrrolidinyl)ethoxy]phenyl]benzo[b]thiophene

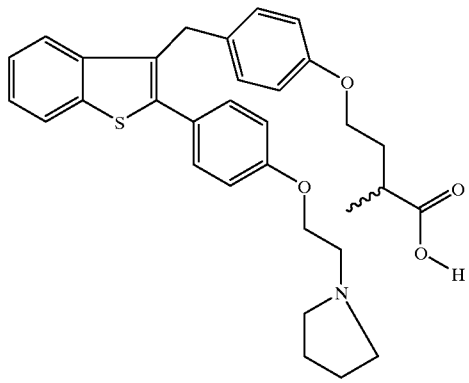

The hydrolysis of the product from Example 31 was carried out at room temperature by NaOH solution using acetone and methanol as the solvent.

FDMS m/e 530 (M+); Analysis for $C_{30}H_{35}NO_4S$: Calcd: C, 72.56; H, 6.66; N, 2.64; Found: C, 65.00; H, 6.42; N, 2.31.

EXAMPLE 33

Preparation of 4-[4-[6-Hydroxy-3-[3-methoxy-4-(1-pyrrolidinylmethyl)benzyl]benzo[b]thiophen-2-yl]phenoxy]butanol Oxalate

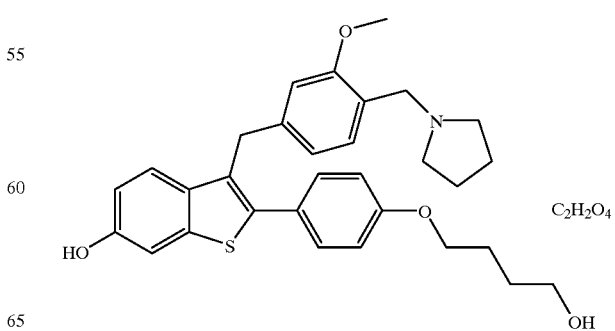

A. 4-[4-[6-Benzyloxy-3-[3-methoxy-4-(1-pyrrolidinylmethyl)benzyl]benzo[b]thiophen-2-yl]phenoxy]butanoic Acid Methyl Ester.

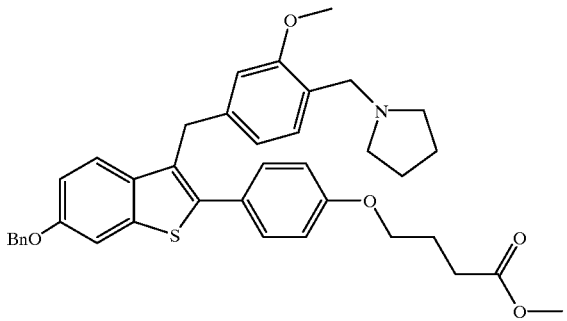

4-[6-Benzyloxy-3-[3-methoxy-4-(1-pyrrolidinylmethyl)benzyl]benzo[b]thiophen-2-yl]phenol (0.10 g; 0.19 mmol), 4-chlorobutyric acid methyl ester (27 mL; 0.22 mmol) and Cs$_2$CO$_3$ (0.43 g; 1.31 mmol) were combined in 2 mL of DMF and heated in an oil bath maintained at 80° C. for 3 h. After cooling to room temperature, water (30 mL) was added, and extraction was carried out with EtOAc (4×25 mL). The combined organics were washed with brine and dried by passage through Na$_2$SO$_4$. Purification was effected by flash chromatography on silica gel, eluting with EtOAc (100–90%)/Et$_3$N(0–5%)/MeOH(0–5%). The title product was obtained as a colorless oil (92 mg, 78%).

$^1$H NMR CDCl$_3$ δ 7.41 (m, 9H), 7.20 (d, J=7.6 Hz, 1H), 6.99 (dd, J=2.2, 8.8 Hz, 1H), 6.92 (d, J=8.7 Hz, 2H), 6.70 (d, J=7.7 Hz, 1H), 6.67 (s, 1H), 5.14 (s, 2H), 4.21 (s, 2H), 4.05 (t, J=6.0 Hz, 2H), 3.71 (s, 6H), 3.62 (s, 2H), 2.56 (m, 6H), 2.15 (m, 2H), 1.78 (br s, 4H). FDMS 636.2 (M+1).

B. 4-[4-[6-Benzyloxy-3-[3-methoxy-4-(1-pyrrolidinylmethyl)benzyl]benzo[b]thiophen-2-yl]phenoxy]butanol.

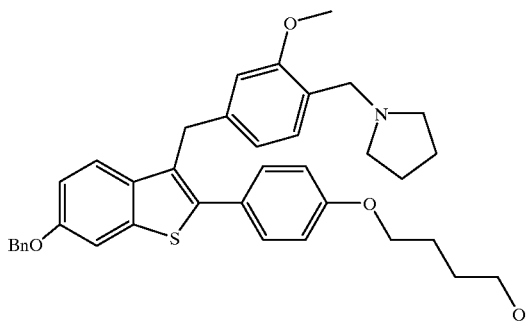

The 4-[4-[6-benzyloxy-3-[3-methoxy-4-(1-pyrrolidinylmethyl)benzyl]benzo[b]thiophen-2-yl]phenoxy]butanoic acid methyl ester prepared in Part A (91 mg; 0.14 mmol) was dissolved in anhydrous THF under argon atmosphere. LAH (10 mg; 0.29 mmol) was added. The mixture was stirred at room temperature for 3 h before it was hydrolyzed by addition of 2 drops of water, 2 drops of 5 M NaOH, and six drops of water. Additional water (25 mL) was added, and extraction was carried out with CH$_2$Cl$_2$. The combined organics were dried by passage through Na$_2$SO$_4$. Purification was effected by flash chromatography on silica gel, eluting with EtOAc(100–90%)/Et$_3$N(0–5%)/MeOH (0–5%). The title product was obtained as a colorless oil (74 mg, 85%).

$^1$H NMR CDCl$_3$ δ 7.41 (m, 10H), 7.10 (d, J=7.6 Hz, 1H), 7.00 (dd, J=7.7, 7.10 Hz, 1H), 6.93 (d, J=8.7 Hz, 2H), 6.72 (d, J=7.8 Hz, 1H), 6.68 (s, 1H), 5.14 (s, 2H), 4.27 (s, 2H), 4.04 (t, J=6.1 Hz, 2H), 3.72 (m, 5H), 3.65 (s, 2H), 2.59 (br s, 4H), 1.92 (m, 4H), 1.80 (br s, 4H). FDMS 608 (M+1).

C. 4-[4-[6-Hydroxy-3-[3-methoxy-4-(1-pyrrolidinylmethyl)benzyl]benzo[b]thiophen-2-yl]phenoxy]butanol Oxalate.

4-[4-[6-Benzyloxy-3-[3-methoxy-4-(1-pyrrolidinylmethyl)benzyl]benzo[b]thiophen-2-yl]phenoxy]butanol prepared in Part B (74 mg; 0.12 mmol) was combined with 30 mg of 10% palladium on charcoal catalyst and 3 mL of 25% aqueous NH$_4$O$_2$CH in 3 mL of THF/MeOH (1:1). The mixture was stirred at room temperature overnight. The product was isolated by filtration through diatomaceous earth and concentration under reduced pressure. Purification was effected by MPLC on silica gel eluting with EtOAc (100–90%)/Et$_3$N(0–5%)/MeOH(0–5%). Conversion to the oxalate was effected in the usual way.

$^1$H NMR MeOH-d$_4$ δ 7.36 (m, 3H), 7.20 (d, J=2.2 Hz, 1H), 7.16 (d, J=7.7 Hz, 1H), 6.93 (d, J=8.6 Hz, 2H), 6.78 (m, 2H), 6.71 (d, J=7.9 Hz, 1H), 4.20 (s, 2H), 4.01 (t, J=6.3 Hz, 2H), 3.93 (s, 2H), 3.72 (s, 3H), 3.62 (t, J=6.3 Hz, 2H), 2.90 (m, 4H), 1.90 (m, 6H), 1.70 (m, 2H). FDMS 518 (M+1 for free base). Anal calc'd for C$_{31}$H$_{35}$NO$_4$S.C$_2$H$_2$O$_4$: C, 65.24; H, 6.10; N; 2.31. Found: C, 64.98; H, 6.42; N, 2.34.

EXAMPLE 34

Preparation of 5-[4-[3-[4-[2-(1-Pyrrolidinyl)ethoxy]benzyl]benzo[b]thiophen-2-yl]phenoxy]pentanol Oxalate

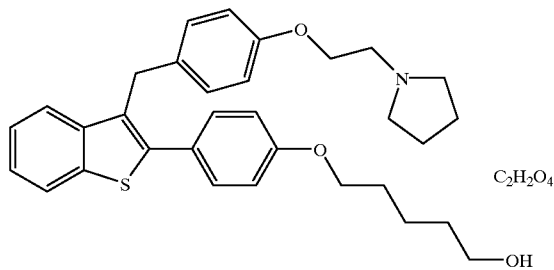

A. 5-[4-[3-[4-[2-(1-Pyrrolidinyl)ethoxy]benzyl]benzo[b]thiophen-2-yl]phenoxy]pentanoic Acid Ethyl Ester.

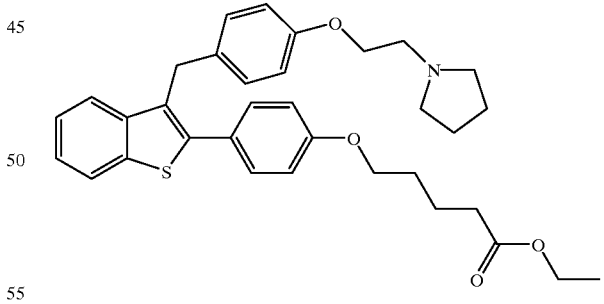

4-[3-[4-[2-(1-Pyrrolidinyl)ethoxy]benzyl]benzo[b]thiophen-2-yl]phenol (0.25 g; 0.58 mmol), ethyl 5-bromovalerate (0.19 mL; 1.20 mmol) and Cs$_2$CO$_3$ (2.3 g; 7.06 mmol) were combined in 5 mL of DMF in a flame-dried, argon-filled flask. The resultant mixture was stirred at room temperature for 2 h. Water (50 mL) was added, and the mixture extracted with EtOAc (4×25 mL). The combined organics were washed with brine and dried by passage through MgSO$_4$. The product (78 mg; 25%) was isolated by flash chromatography on silica gel, eluting with EtOAc (100–95%)/-Et$_3$N(0–5%).

¹H NMR CDCl₃ δ 7.85 (d, J=8.6 Hz, 1H), 7.51 (m, 1H), 7.43 (d, J=8.7 Hz, 2H), 7.31 (m, 2H), 7.06 (d, J=8.5 Hz, 2H), 6.93 (d, J=8.6 Hz, 2H), 6.83 (d, J=8.5 Hz, 2H), 4.22 (s, 2H), 4.15 (q, J=7.2 Hz, 2H), 4.08 (t, J=6.0 Hz, 2H), 4.02 (br s, 2H), 2.90 (t, J=6.0 Hz, 2H), 2.62 (br s, 4H), 2.41 (br s, 2H), 1.83 (m, 8H), 1.28 (t, J=7.1 Hz, 3H). FDMS 557 (M+1).

B. 5-[4-[3-[4-[2-(1-Pyrrolidinyl)ethoxy]benzyl]benzo[b]thiophen-2-yl]phenoxy]pentanol Oxalate.

5-[4-[3-[4-[2-(1-Pyrrolidinyl)ethoxy]benzyl]benzo[b]thiophen-2-yl]phenoxy]pentanoic acid ethyl ester prepared in part A (78 mg; 0.14 mmol) was dissolved in 3 mL of anhydrous THF under an argon atmosphere, then LAH (10 mg; 0.29 mmol) was added. The resultant mixture was stirred at room temperature for 3 h. To the reaction was added 1 drop of water, 1 drop of 5 M NaOH, and 3 drops of water. The mixture was stirred at room temperature for 45 min, then water (25 mL) was added. Extraction was carried out with EtOAc (4×25 mL). The combined organics were dried by passage through Na₂SO₄. The product was isolated as a colorless oil (49 mg; 66%) by flash chromatography on silica gel, eluting with EtOAc(10–90%)/Et₃N(0–5%)/MeOH(0–5%). Conversion to the oxalate was effected in the usual way.

¹H NMR CDCl₃ δ 7.84 (m, 1H), 7.52 (m, 1H), 7.43 (m, 2H), 7.30 (m, 2H), 7.07 (d, J=9.0 Hz, 2H), 6.91 (d, J=8.7 Hz, 2H), 6.83 (d, J=8.5 Hz, 2H), 4.22 (s, 2H), 4.09 (t, J=6.0 Hz, 2H), 4.01 (t, J=6.4 Hz, 2H), 3.70 (t, J=6.2 Hz, 2H), 2.89 (t, J=6.0 Hz, 2H), 2.65 (br s, 4H), 1.83 (m, 6H), 1.64 (m, 4H). FDMS 516 (M+1 for free base); Anal calc'd for $C_{32}H_{37}NO_3S \cdot C_2H_2O_4 \cdot 1/2 H_2O$: C, 66.43; H, 6.56; N; 2.28. Found: C, 66.08; H, 6.32; N, 2.16.

EXAMPLE 35

Preparation of 3-[4-[3-[4-[2-(1-Pyrrolidinyl)ethoxy]benzyl]benzo[b]thiophen-2-yl]phenoxy]propanol Oxalate

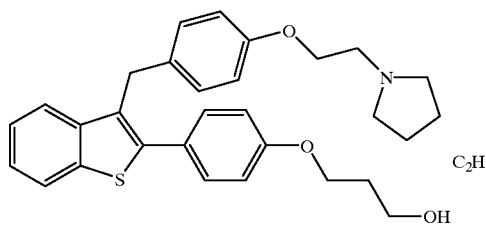

3-Bromopropanol (1.3 mL; 1.44 mmol) was combined with 2,6-lutidine (4.2 mL; 36.0 mmol) in CH₂Cl₂ (25 mL) in a flame-dried, argon-filled flask. The mixture was cooled to 0° C. and triisopropylsilyl triflate (5 mL; 18.7 mmol) was added. After standing at room temperature for 1.5 h, water was added and extraction was carried out with EtOAc. The combined organics were dried by passage through Na₂SO₄. Concentration under reduced pressure left the 3-bromo-1-triisopropylsilyloxypropane, which was used without further purification.

4-[3-[4-[2-(1-Pyrrolidinyl)ethoxy]benzyl]benzo[b]thiophen-2-yl]phenol (0.25 g; 0.58 mmol), 0.21 g (0.70 mmol) of the triisopropylsilyl ether prepared above and Cs₂CO₃ (1.33 g; 4.07 mmol) were combined in 5 mL of DMF in a flame-dried, argon-filled flask and heated in an oil bath maintained at 70° C. for 2 h. After cooling to room temperature, water was added (25 mL) and extraction was carried out with EtOAc (4×25 mL). The combined organics were dried by passage through Na₂SO₄. The triisopropylsi-lyl protecting group was removed by stirring with an excess of tetrabutylammonium fluoride in THF at room temperature for 0.5 h. The product was isolated as a colorless oil (165 mg; 58%) by flash chromatography on silica gel, eluting with EtOAc(10–90%)/Et₃N(0–5%)/MeOH(0–5%). Conversion to the oxalate was effected in the usual way.

¹H NMR CDCl₃ δ 7.84 (m, 1H), 7.52 (m, 1H), 7.43 (d, J=8.6 Hz, 2H), 7.30 (m, 2H), 7.05 (d, J=8.5 Hz, 2H), 6.95 (d, J=8.6 Hz, 2H), 6.82 (d, J=8.5 Hz, 2H), 4.21 (s, 2H), 4.15 (t, J=5.9 Hz, 2H), 4.08 (t, J=6.0 Hz, 2H), 3.88 (t, J=5.9 Hz, 2H), 2.90 (t, J=5.9 Hz, 2H), 2.64 (br s, 4H), 2.07 (m, 2H), 1.81 (m, 4H). FDMS 488 (M+1 for free base). Anal calc'd for $C_{30}H_{33}NO_3S \cdot C_2H_2O_4$: C, 66.55; H, 6.07; N; 2.36. Found: C, 66.79; H, 6.23; N, 2.36.

EXAMPLE 36

Preparation of 4-[4-[3-[3-Methoxy-4-(1-pyrrolidinylmethyl)benzyl]benzo[b]thiophen-2-yl]phenoxy]butanol Oxalate

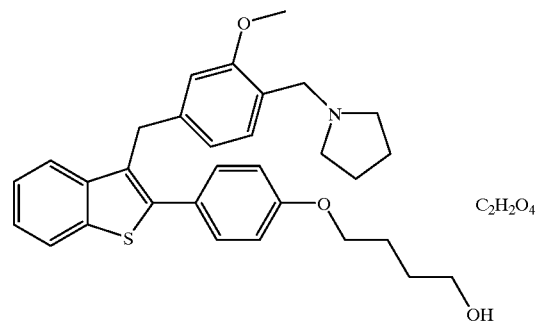

A. 4-[4-[3-[3-Methoxy-4-(1-pyrrolidinylmethyl)benzyl]benzo[b]thiophen-2-yl]phenoxy]butanoic Acid Methyl Ester.

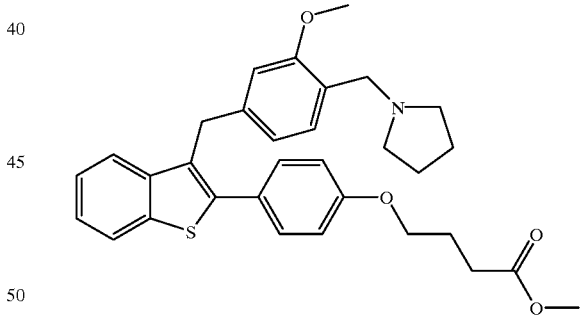

Essentially by application of the procedure of Example 34, Part A, using 4-[3-[3-methoxy-4-(1-pyrrolidinylmethyl)benzyl]benzo[b]thiophen-2-yl]phenol and 4-bromobutyric acid methyl ester as the starting materials, the product was obtained in 58% yield.

¹H NMR CDCl₃ δ 7.84 (m, 1H), 7.56 (m, 1H), 7.45 (d, J=8.6 Hz, 2H), 7.30 (m, 2H), 7.20 (d, J=7.6 Hz, 1H), 6.92 (d, J=8.6 Hz, 2H), 6.70 (d, J=7.9 Hz, 1H), 6.67 (s, 1H), 4.26 (s, 2H), 4.05 (t, J=6.1 Hz, 2H), 3.71 (s, 3H), 3.70 (s, 3H), 3.63 (s, 2H), 2.56 (br s, 6H), 2.15 (m, 2H), 1.78 (br s, 4H). FDMS 529 (M+1).

B. 4-[4-[3-[3-Methoxy-4-(1-pyrrolidinylmethyl)benzyl]benzo[b]thiophen-2-yl]phenoxy]butanol Oxalate.

Essentially by application of the procedure of Example 34, Part B, using 4-[4-[3-[3-methoxy-4-(1- pyrrolidinylmethyl)benzyl]benzo[b]thiophen-2-yl]phenoxy] butanoic acid methyl ester prepared in Part A as the starting material, the desired compound was obtained in 82% yield. Conversion to the oxalate was effected by the usual procedure.

$^1$H NMR CDCl$_3$ δ 7.84 (m, 1H), 7.56 (m, 1H), 7.44 (d, J=8.7 Hz, 2H), 7.30 (m, 2H), 7.20 (d, J=7.6 Hz, 1H), 6.94 (d, J=8.8 Hz, 2H), 6.68 (d, J=8.0 Hz, 1H), 6.67 (s, 1H), 4.26 (s, 2H), 4.04 (t, J=6.1 Hz, 2H), 3.74 (t, J=6.3 Hz, 2H), 3.70 (s, 3H), 3.63 (s, 2H), 2.58 (br s, 4H), 1.91 (m, 4H), 1.77 (br s, 4H). FDMS 502 (M+1). Anal calc'd for C$_{31}$H$_{35}$NO$_3$S.C$_2$H$_2$O$_4$: C, 67.00; H, 6.26; N; 2.09. Found: C, 66.76; H, 6.05; N, 2.09.

EXAMPLE 37

Preparation of 3-[4-[2-(1-Pyrrolidinyl)ethoxy] benzyl]-2-[4-[3-(5-tetrazolyl)propoxy]phenyl]benzo [b]thiophene

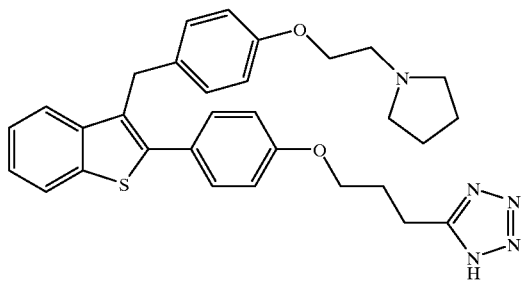

4-[4-[3-[4-[2-(1-Pyrrolidinyl)ethoxy]benzyl]benzo[b] thiophen-2-yl]phenoxy]butyronitrile (0.104 g; 0.21 mmol) and tri-n-butyltin azide (0.12 mL; 0.42 mmol) were combined in 1.0 mL of ethyleneglycol diethyl ether, heated in an oil bath maintained at 115° C. overnight, and cooled to room temperature. A mixture was prepared of 45 mL of water, 5 mL of conc HCl and 50 mL of hexane. The reaction mixture was poured into this mixture with rapid stirring, and washed in with a small amount of EtOAc. After stirring for 1.5 h, the product was isolated by suction filtration and washed with fresh water. Purification was effected by HPLC on a [Vydac] C$_{18}$ reversed-phase column, eluting with H$_2$O/TFA/CH$_3$CN (94:1:5–>39:1:60). Pure tetrazole (27.3 mg; 24%) was obtained.

$^1$H NMR DMSO-d$_6$ δ 7.84 (m, 1H), 7.52 (m, 1H), 7.43 (d, J=8.6 Hz, 2H), 7.30 (m, 2H), 7.05 (d, J=8.5 Hz, 4H), 6.82 (d, J=8.5 Hz, 2H), 4.21 (s, 2H), 4.17 (s, 2H), 4.08 (t, J=6.0 Hz, 2H), 3.52 (t, J=5.9 Hz, 2H), 3.05 (t, J=5.9 Hz, 2H), 2.50 (br s, 4H), 2.15 (m, 2H), 1.81 (br s, 4H). FAB+ MS 540.2 (M+1).

EXAMPLE 38

Preparation of Methyl 4-[4-[5-Methoxy-3-[3-methoxy-4-(1-pyrrolidinylmethyl)benzyl]benzo[b] thiophen-2-yl]phenoxy]butyrate Oxalate

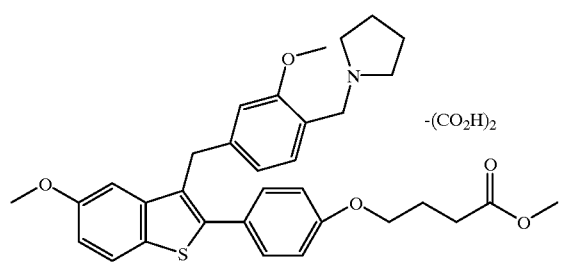

A. 4-(5-Methoxybenzo[b]thiophen-2-yl)phenol.

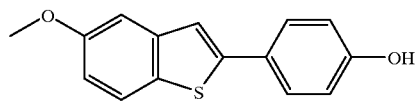

A mixture of 3.43 g (16.5 mmol) of 5-methoxybenzo[b] thiophene-2-boronic acid, 6.21 g (16.5 mmol) of 4-(triisopropylsilyloxy)iodobenzene, 952.3 mg (0.82 mmol) of Pd(PPh$_3$)$_4$ and 16 mL of 2.0 M Na$_2$CO$_3$ in 80 mL of distilled THF was heated at reflux for 19 h. The mixture was filtered through a diatomaceous earth pad to remove the Pd catalyst with thorough EtOAc, THF, and H$_2$O rinse. The layers were separated and the organic layer was washed with 200 mL of brine. The aqueous layers were back extracted with 2×500 mL of EtOAc. Combined organic layers were dried over MgSO$_4$, concentrated, and purified by PrepLC 500A with 0–20% Et$_2$O-hexanes as eluent to afford 2.22 g (53%) of the title compound along with 314 mg (4.6%) of its TIPS ether.

FDMS 256.1 (M+); Anal. Calcd for C$_{15}$H$_{12}$O$_2$S: C, 70.29; H, 4.72. Found: C, 70.20; H, 4.61.

B. Methyl 4-[4-(5-Methoxybenzo[b]thiophen-2-yl) phenoxy]butyrate.

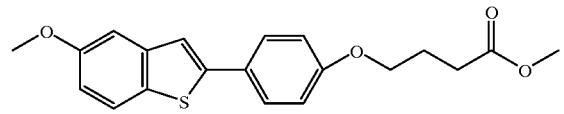

A mixture of 549.6 mg (2.14 mmol) of the phenol (Part A), 2.09 g (6.4 mmol) of Cs$_2$CO$_3$, and 0.32 mL (2.57 mmol) of methyl 4-chlorobutyrate in 5.0 mL of anhydrous DMF was heated at 85–90° C. (bath temperature) for 2 h. The mixture was diluted with EtOAc to ca. 100 mL and filtered. The filtrate was washed with 100 mL of saturated aqueous NH$_4$Cl, H$_2$O (2×) and saturated aqueous NaHCO$_3$. The aqueous layers were back extracted with 2×100 mL of EtOAc. Combined organic layers were dried over MgSO$_4$ and concentrated to yield 756.9 mg (99%) of the clean crude product.

$^1$H NMR (CDCl$_3$) δ 7.66 (d, J=8.8 Hz, 1H), 7.61 (d, J=8.6 Hz, 2H), 7.35 (s, 1H), 7.21 (d, J=2.3 Hz, 1H), 6.94 (m, 1H), 6.93 (d, J=8.6 Hz, 2H), 4.05 (t, J=6.0 Hz, 2H), 3.87 (s, 3H), 3.70 (s, 3H), 2.55 (t, J=7.2 Hz, 2H), 2.14 (m, 2H).

C. Methyl 4-[4-[5-Methoxy-3-[3-methoxy-4-(1-pyrrolidinylmethyl)benzoyl]benzo[b]thiophen-2-yl] phenoxy]butyrate.

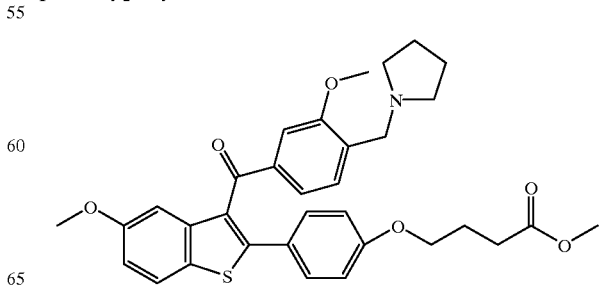

Friedel-Crafts acylation of 852 mg (2.4 mmol) of the above benzo[b]thiophene (Part B) with an equimolar amount of 3-methoxy-4-(1-pyrrolidinylmethyl)benzoyl chloride as previously described afforded 675.5 mg (49%) of the title compound along with 331.0 mg (18%) of 3,6-diacylated product and 245.1 mg (29%) of recovered starting benzo[b]thiophene.

FDMS 574 (M+1); Anal. Calcd for $C_{33}H_{35}NO_6S$: C, 69.9; H, 6.15; N, 2.44. Found: C, 69.19; H, 6.01; N, 2.38.

D. Methyl 4-[4-[5-Methoxy-3-[3-methoxy-4-(1-pyrrolidinylmethyl)benzyl]benzo[b]thiophen-2-yl]phenoxy]butyrate Oxalate.

The title compound was prepared in 56% yield in three steps from the ketone (Part C): (1) reduction of 224.7 mg (0.39 mmol) of the ketone (Part 3) with 37.0 mg (0.98 mmol) of $NaBH_4$ in the presence of 218.9 mg (0.59 mmol) of $CeCl_3 \cdot 7H_2O$ in 1.5 mL of MeOH overnight; (2) dehydroxylation with $Et_3SiH/TFA$ in $CH_2Cl_2$ at 0° C. for 1 h; followed by (3) oxalate formation as previously described.

FDMS 559.1 (M+); Anal. Calcd for $C_{33}H_{37}NO_5S \cdot 0.9C_2H_2O_4 \cdot 0.3C_4H_8O_2$: C, 64.81; H, 6.22; N, 2.10. Found: C, 64.77; H, 6.61; N, 2.08.

EXAMPLE 39

Preparation of 4-[4-[5-Methoxy-3-[3-methoxy-4-(1-pyrrolidinylmethyl)benzyl]benzo[b]thiophen-2-yl]phenoxy]butanol Oxalate

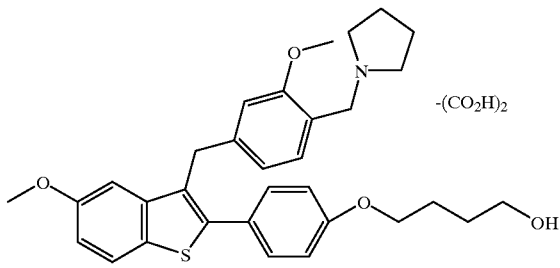

The title compound was prepared in 27% yield in three steps from LAH reduction of methyl 4-[4-[5-methoxy-3-[3-methoxy-4-(1-pyrrolidinylmethyl)benzoyl]benzo[b]thiophen-2-yl]phenoxy]butyrate (Part C of Example 38) in THF at 0–10° C. for 1 h, followed by dehydroxylation with $Et_3SiH/TFA$ in $CH_2Cl_2$ and oxalate formation as previously described.

FDMS 531.2 (M+); Anal. Calcd for $C_{34}H_{39}NO_8S \cdot 0.7C_4H_8O_2$: C, 64.68; H, 6.58; N, 2.05. Found: C, 64.35; H, 6.76; N, 2.21.

EXAMPLE 40

Preparation of 2-[4-(3-Ethoxy-3-oxopropyl)phenyl]-3-[4-[2-(1-pyrrolidinyl)ethoxy]benzyl]benzo[b]thiophene

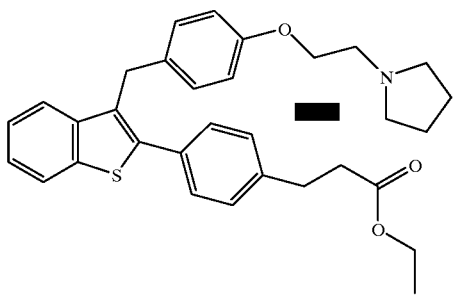

A. 2-(4-Formylphenyl)-3-[4-[2-(1-pyrrolidinyl)ethoxy]benzyl]benzo[b]thiophene.

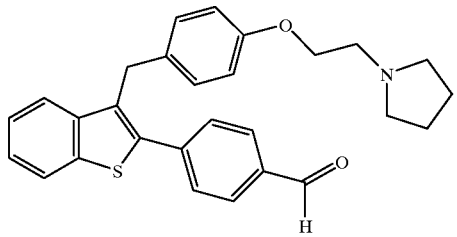

To a solution of $Mg^0$ (0.385 mg, 16.08 mmol), in THF (1 mL), was added p-bromobenzaldehyde dimethylacetal (3.71 g, 16.08 mmol, prepared from p-bromobenzaldehyde and MeOH following standard procedures) and the mixture stirred for 1 h. Additional THF (15 mL) was added to the Grignard reagent and then the solution transferred to a flask containing 2-dimethylaminobenzo[b]thiophene-3-yl 4-[2-(1-pyrrolidinyl)ethoxy]phenyl ketone (3.04 g, 8.04 mmol) in THF (15 mL). The mixture was stirred at room temperature for 2 h, then quenched by the addition of saturated $NH_4Cl$, $H_2O$, and extracted into EtOAc. The organic extracts were concentrated in vacuo, and the resulting residue purified by flash chromatography ($SiO_2$, 2% MeOH in $CHCl_3$). To LAH (47 mg, 1.25 mmol) in THF (1 mL) was added the above ketone (585 mg, 1.25 mmol) in THF (4 mL). The mixture was stirred at room temperature for 1 h and then quenched by the sequential addition of 50 μL of $H_2O$, 50 μL of 15% NaOH, and 150 μl $H_2O$. The resulting aluminum salts were removed by filtering over a pad of diatomaceous earth and the filtrate concentrated in vacuo. The resulting alcohol was then taken up in 80% HOAc, stirred for 2 h and then concentrated in vacuo. The residue was dissolved in $CH_2Cl_2$, cooled to 0° C. and treated with $Et_3SiH$ (7 equivalents). TFA (10 equivalents) was then added and the reaction mixture stirred at 0° C. for 1 minute, and then the reaction was quenched by the addition of saturated $NaHCO_3$. Material was then diluted 10 fold with EtOAc, the organics washed with $H_2O$, and concentrated in vacuo. The residue was purified by flash chromatography ($SiO_2$, 1% MeOH in $CHCl_3$ with 1% $Et_3N$ v/v added).

FDMS 441.9 (M+); Anal. Calcd. For $C_{28}H_{27}NO_2S \cdot 0.5 H_2O$: C, 74.63; H, 6.26; N, 3.11. Found: C, 74.86; H, 6.17; N, 3.08.

B. 2-[4-(3-Ethoxy-3-oxoprop-1-enyl)phenyl]-3-[4-[2-(1-pyrrolidinyl)ethoxy]benzyl]benzo[b]thiophene.

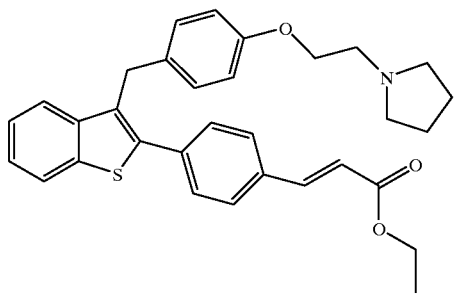

To a solution of NaH (12 mg, 0.51 mmol), in THF (1 mL) and under $N_2$, was added triethyl phosphonoacetate (58 μL, 0.292 mmol) and the mixture stirred at room temperature for 30 minutes. To this ylide was then added the above benzaldehyde (Part A, 129 mg, 0.292 mmol) in THF (0.5 mL), and the mixture stirred at room temperature for 30 min. After diluting with EtOAc (50 fold), the organics were washed with saturated $NaHCO_3$, $H_2O$, brine, and concentrated in vacuo. Product was purified by flash chromatography ($SiO_2$, 5% MeOH in $CHCl_3$); yielding 130 mg of desired material.

$^1$H NMR ($CDCl_3$) d 7.86 (d, J=7.1 Hz, 1H), 7.71 (d, J=15.9 Hz, 1H), 7.54 (m, 5H), 7.35 (m, 2H), 7.06 (d, J=8.5 Hz, 2H), 6.84 (d, J=6.8 Hz, 2H), 6.47 (d, J=15.9 Hz, 1H), 4.29 (q, J=7.1, 14.3 Hz, 2H), 4.26 (s, 2H), 4.09 (t, J=6.0 Hz, 2H), 2.90 (t, J=6.0 Hz, 2H), 2.63 (m, 4H), 1.82 (m, 4H), 1.36 (t, J=7.1 Hz, 3H); FDMS 512 (M+).

C. 2-[4-(3-Ethoxy-3-oxopropyl)phenyl]-3-[4-[2-(1-pyrrolidinyl)ethoxy]benzyl]benzo[b]thiophene.

To a solution of the above unsaturated ester (Part B, 110 mg, 0.215 mmol) in EtOH (5 mL) was added 5% Pd/C (110 mg) and the mixture rapidly stirred under $H_2$ (1 atm) for 10 h. The catalyst was then removed by filtering over a pad of diatomaceous earth, the filtrate concentrated in vacuo, and the material purified by flash chromatography ($SiO_2$, 10% MeOH in $CHCl_3$), yielding 51 mg of desired product.

FDMS 513 (M+); Anal. Calcd. for $C_{32}H_{35}NO_3S$: C, 74.82; H, 6.87; N, 2.73; Found: C, 74.87; H, 6.85; N, 2.89.

What is claimed is:

1. A compound of formula I, or a pharmaceutically acceptable salt thereof,

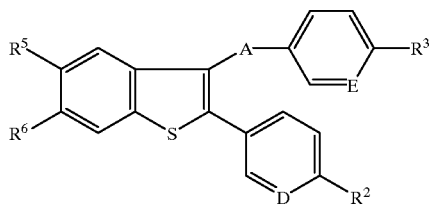

wherein

A is carbonyl or methylene;

D is CH, $CR^d$ or N in which $R^d$ is formyl, hydroxymethyl, methyl or methoxy;

E is CH, $CR^e$ or N in which $R^e$ is methyl, methoxy or halo;

$R^2$ and $R^3$ are defined together such that

A. $R^2$ is $-X^2-(CH_2)_m-NR^aR^b$ in which $X^2$ is a direct bond, methylene or O; m is 1, 2, 3, 4 or 5; provided that when m is 1, then $X^2$ is a direct bond; and $R^a$ and $R^b$ are independently hydrogen or (1–3C)alkyl or the group $NR^aR^b$ is pyrrolidino, piperidino, or morpholino; and $R^3$ is $-CH_2-R^c$, in which $R^c$ is 5-tetrazolyl, 2-carboxy-5-oxopyrrolidin-1-yl or 2-{{(1–4C)alkoxy}carbonyl}-5-oxopyrrolidin-1-yl; or $R^3$ is $-O-(CH_2)_e-(CHCH_3)_f-R^f$ in which e is 0, 1, 2 or 3 and f is 0 or 1 and the sum of e and f is 1, 2 or 3 and $R^f$ is as defined below; or B. $R^2$ is $-X^2-(CH_2)_n-R^f$ in which $X^2$ is a direct bond, methylene or O; n is 1, 2, 3 or 4; and $R^f$ is 5-tetrazolyl, carboxy, {(1–4C)alkoxy}carbonyl or hydroxymethyl; and $R^3$ is $-X^3-(CH_2)_s-NR^sR^t$ or $-CH_2-R^k$, in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^k$ is 2-oxopyrrolidin-1-yl or 3-(1-oxoethyl)imidazolidin-1-yl; and one of $R^5$ and $R^6$ is hydrogen; and the other of $R^5$ and $R^6$ is hydrogen, hydroxy or methoxy.

2. The compound, or a pharmaceutically acceptable salt thereof, of formula I as claimed in claim 1 wherein A is carbonyl or methylene;

D is CH, $CR^d$ or N in which $R^d$ is formyl, hydroxymethyl, methyl or methoxy;

E is CH, $CR^e$ or N in which $R^e$ is methyl, methoxy or halo;

$R^2$ and $R^3$ are defined together such that

A. $R^2$ is $-X^2-(CH_2)_m-NR^aR^b$ in which $X^2$ is a direct bond, methylene or O; m is 1, 2, 3, 4 or 5; provided that when m is 1, then $X^2$ is a direct bond; and $R^a$ and $R^b$ are independently hydrogen or (1–3C)alkyl or the group $NR^aR^b$ is pyrrolidino, piperidino, or morpholino; and $R^3$ is $-CH_2-R^c$, in which $R^c$ is 5-tetrazolyl, 2-carboxy-5-oxopyrrolidin-1-yl or 2-{{(1–4C)alkoxy}carbonyl}-5-oxopyrrolidin-1-yl; or B. $R^2$ is $-X^2-(CH_2)_n-R^f$ in which $X^2$ is a direct bond, methylene or O; n is 1, 2 or 3; and $R^f$ is 5-tetrazolyl, carboxy, {(1–4C)alkoxy}carbonyl} or hydroxymethyl; and $R^3$ is $-X^3-(CH_2)_s-NR^sR^t$ or $-CH_2-R^k$, in which $X^3$ is a direct bond, methylene or O; s is 1 or 2; provided that when s is 1, then $X^3$ is a direct bond; and $R^s$ and $R^t$ are independently hydrogen or (1–3C)alkyl or the group $NR^sR^t$ is pyrrolidino, piperidino, or morpholino; and $R^k$ is 2-oxopyrrolidin-1-yl or 3-(1-oxoethyl)imidazolidin-1-yl;

$R^5$ is hydrogen; and $R^6$ is hydrogen, hydroxy or methoxy.

3. The compound, or salt thereof, of claim 1 or 2 wherein halo is fluoro, chloro, bromo or iodo; a (1–3C)alkyl group is methyl, ethyl, propyl or isopropyl; and a (1–4C)alkoxy group is methoxy, ethoxy, isopropoxy or t-butoxy.

4. The compound, or salt thereof, of claim 1 wherein D is CH and E is CH or $CR^e$ in which $R^e$ is methoxy.

5. The compound, or salt thereof, of claim 1 wherein $R^3$ is $-CH_2-R^c$ in which $R^c$ is 5-tetrazolyl, 2-carboxy-5-oxopyrrolidin-1-yl or 2-(ethoxycarbonyl)-5-oxopyrrolidin-1-yl; and $R^2$ is 2-pyrrolidinoethoxy.

6. The compound, or salt thereof, of claim 1 wherein $R^2$ is $-X^2-(CH_2)_n-R^f$ in which $X^2$ is O; n is 1 or 3; $R^f$ is carboxy, {(1–4C)alkoxy} carbonyl in which (1–4C)alkoxy is methoxy, ethoxy or t-butoxy, or hydroxymethyl; and A is methylene.

7. The compound, or salt thereof, of claim 1 wherein $R^3$ is $-X^3-(CH_2)_s-NR^sR^t$ wherein $R^3$ is pyrrolidinomethyl and E is $CR^e$ in which $R^e$ is methoxy.

8. The compound, or salt thereof, of claim 1 wherein $R^5$ is methoxy.

9. The compound, or salt thereof, of claim 1 wherein $R^6$ is hydroxy.

10. The compound, or salt thereof, of claim 1 and wherein A is methylene.

11. The salt as claimed in claim 1 which is an acid-addition salt made with an acid which provides a pharmaceutically acceptable anion or, for a compound of formula I which bears an acidic moiety, which is the salt made with a base which affords a pharmaceutically acceptable cation.

12. A pharmaceutical formulation comprising in association with a pharmaceutically acceptable carrier, diluent or excipient, a compound of formula I, or a pharmaceutically acceptable salt thereof, as provided in claim 1.

13. A process for preparing a compound of formula I, or a pharmaceutically acceptable salt thereof, as provided in claim 1 which is selected from (a-1) for a compound of formula I in which $R^2$ is $-X^2-(CH_2)_m-NR^aR^b$ or $-X^2-(CH_2)_n-R^f$ in which $X^2$ is O, alkylating the hydroxy group of a corresponding phenol of formula II;

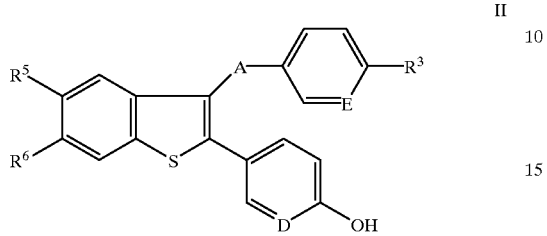

II with a group of formula $X-(CH_2)_m-NR^aR^b$ or $X-(CH_2)_n-R^f$, respectively, or a protected derivative thereof, wherein X is a conventional leaving group;

(a-2) for a compound of formula I in which $R^3$ is $-O-(CH_2)_e-(CHCH_3)_f-R^f$ or $-X^3-(CH_2)_s-NR^sR^t$ in which $X^3$ is O, alkylating the hydroxy group of a corresponding phenol of formula III;

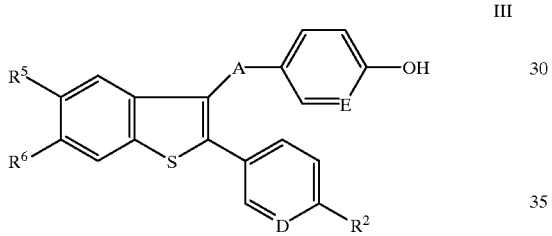

III with a group of formula $X-(CH_2)_e-(CHCH_3)_f-R^f$ or $X-(CH_2)_s-NR^sR^t$, respectively, or a protected derivative thereof, wherein X is a conventional leaving group;

(b) for a compound of formula I in which $R^c$ is 2-carboxy-5-oxopyrrolidin-1-yl or $R^f$ is carboxy, decomposing the ester of a corresponding compound of formula I in which $R^c$ is 2-{{(1–4C)alkoxy}carbonyl}-5-oxopyrrolidin-1-yl or $R^f$ is {(1–4C)alkoxy}carbonyl, respectively;

(c) for a compound of formula I in which $R^f$ is hydroxymethyl, reducing the acid or the ester of a corresponding compound of formula I in which $R^f$ is carboxy or carbonyl, respectively;

(d) for a compound of formula I in which $R^3$ is $-CH_2-R^c$ in which $R^c$ is 2-{{(1–4C)alkoxy}carbonyl}-5-oxopyrrolidin-1-yl, or $R^3$ is $CH_2-NR^sR^t$, or $R^3$ is $-CH_2-R^k$, alkylating the nitrogen of a corresponding amine of formula $H-R^c$, $H-NR^sR^t$ or $H-R^k$, respectively, using a bromide corresponding to the compound of formula I, but in which $R^3$ is $-CH_2-X$, wherein X is a conventional leaving group;

(e) for a compound of formula I in which $R^f$ is carboxy, hydrolysis of the cyano group of a corresponding compound but in which $R^f$ is cyano;

(f) for a compound of formula I in which A is methylene, reductive removal of the hydroxy group of a corresponding compound but in which A is $-CH(OH)-$;

(g) for a compound of formula I in which $R^2$ is $-X^2-(CH_2)_m-NR^aR^b$, alkylating the nitrogen of a corresponding amine of formula $H-NR^aR^b$, using a compound corresponding to the compound of formula I, but in which $R^2$ is $-X^2-(CH_2)_m-X$ in which X is a conventional leaving group;

(h) for a compound of formula I in which A is carbonyl, condensation of a reagent of formula IV

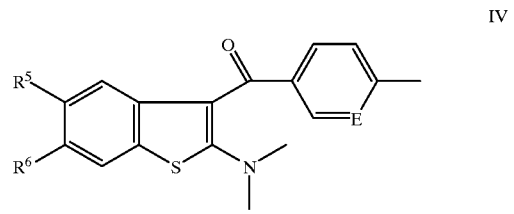

IV with a Gringard reagent of formula V

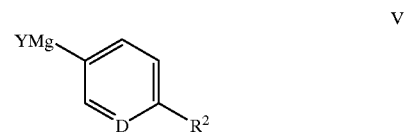

V (or a protected derivative thereof) wherein Y is chloro, bromo or iodo;

(i) for a compound of formula I in which $R^f$ is 5-tetrazolyl, cycloaddition of a corresponding compound but in which $R^f$ is cyano with an azide reagent;

(j) for a compound of formula I in which A is carbonyl, acylation of a compound of formula VI

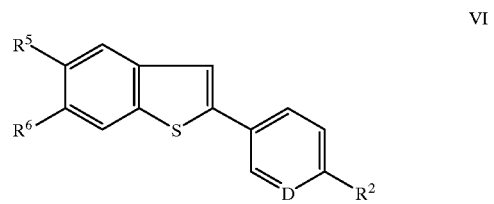

VI with a Friedel-Crafts reagent derived from an acid of formula VII

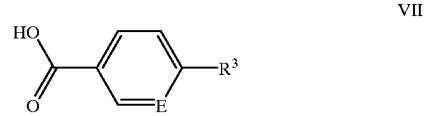

VII or from the corresponding nitrile;

(k) for a compound of formula I in which $R^2$ is $-X^2-(CH_2)_n-R^f$ in which $X^2$ is a direct bond and n is 2, reducing the double bond of a corresponding compound but in which $R^2$ is $-CH=CH-R^f$;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of such a compound of formula I with an acid affording a physiologically acceptable counterion, or, for a compound of formula I which bears an acidic moiety, reacting the acidic form of such a compound of formula I with a base which affords a pharmaceutically acceptable cation, or by any other conventional procedure;

and wherein, unless otherwise described, A, $R^2$, $R^3$, $R^5$ and $R^6$ have the values described in claim 1.

14. A method of inhibiting thrombin in a patient comprising administering to a patient in need thereof a thrombin inhibiting amount of a compound of claim 1 or a pharmaceutically acceptable salt thereof.

15. The compound, or salt thereof, of claim 2 wherein D is CH and E is CH or $CR^e$ in which $R^e$ is methoxy.

16. The compound, or salt thereof, of claim 3 wherein D is CH and E is CH or $CR^e$ in which $R^e$ is methoxy.

17. The compound, or salt thereof, of claim 2 wherein $R^3$ is —$CH_2$—$R^c$ in which $R^c$ is 5-tetrazolyl, 2-carboxy-5-oxopyrrolidin-1-yl or 2-(ethoxy-carbonyl)-5-oxopyrrolidin-1-yl; and $R^2$ is 2-pyrrolidinoethoxy.

18. The compound, or salt thereof, of claim 3 wherein $R^3$ is —$CH_2$—$R^c$ in which $R^c$ is 5-tetrazolyl, 2-carboxy-5-oxopyrrolidin-1-yl or 2-(ethoxy-carbonyl)-5-oxopyrrolidin-1-yl; and $R^2$ is 2-pyrrolidinoethoxy.

19. The compound, or salt thereof, of claim 4 wherein $R^3$ is —$CH_2$—$R^c$ in which $R^c$ is 5-tetrazolyl, 2-carboxy-5-oxopyrrolidin-1-yl or 2-(ethoxy-carbonyl)-5-oxopyrrolidin-1-yl; and $R^2$ is 2-pyrrolidinoethoxy.

20. The compound, or salt thereof, of claim 2 wherein $R^2$ is —$X^2$—$(CH_2)_n$—$R^f$ in which $X^2$ is O; n is 1 or 3; $R^f$ is carboxy, carbonyl in which (1–4C)alkoxy is methoxy, ethoxy or t-butoxy, or hydroxymethyl; and A is methylene.

21. The compound, or salt thereof, of claim 3 wherein $R^2$ is —$X^2$—$(CH_2)_n$—$R^f$ in which $X^2$ is O; n is 1 or 3; $R^f$ is carboxy, carbonyl in which (1–4C)alkoxy is methoxy, ethoxy or t-butoxy, or hydroxymethyl; and A is methylene.

22. The compound, or salt thereof, of claim 4 wherein $R^2$ is —$X^2$—$(CH_2)_n$—$R^f$ in which $X^2$ is O; n is 1 or 3; $R^f$ is carboxy, carbonyl in which (1–4C)alkoxy is methoxy, ethoxy or t-butoxy, or hydroxymethyl; and A is methylene.

23. The compound, or salt thereof, of claim 2 wherein $R^3$ is —$X^3$—$(CH_2)_s$—$NR^sR^t$ wherein $R^3$ is pyrrolidinomethyl and E is $CR_e$ in which $R_e$ is methoxy.

24. The compound, or salt thereof, of claim 3 wherein $R^3$ is —$X^3$—$(CH_2)_s$—$NR^sR^t$ wherein $R^3$ is pyrrolidinomethyl and E is $CR^e$ in which $R^e$ is methoxy.

25. The compound, or salt thereof, of claim 4 wherein $R^3$ is —$X^3$—$(CH_2)_s$—$NR^sR^t$ wherein $R^3$ is pyrrolidinomethyl and E is $CR^e$ in which $R^e$ is methoxy.

26. The compound, or salt thereof, of claim 2 wherein $R^5$ is methoxy.

27. The compound, or salt thereof, of claim 3 wherein $R^5$ is methoxy.

28. The compound, or salt thereof, of claim 4 wherein $R^5$ is methoxy.

29. The compound, or salt thereof, of claim 5 wherein $R^5$ is methoxy.

30. The compound, or salt thereof, of claim 6 wherein $R^5$ is methoxy.

31. The compound, or salt thereof, of claim 7 wherein $R^5$ is methoxy.

32. The compound, or salt thereof, of claim 2 wherein $R^6$ is hydroxy.

33. The compound, or salt thereof, of claim 3 wherein $R^6$ is hydroxy.

34. The compound, or salt thereof, of claim 4 wherein $R^6$ is hydroxy.

35. The compound, or salt thereof, of claim 5 wherein $R^6$ is hydroxy.

36. The compound, or salt thereof, of claim 6 wherein $R^6$ is hydroxy.

37. The compound, or salt thereof, of claim 7 wherein $R^6$ is hydroxy.

38. The compound, or salt thereof, of claim 2 wherein $R^5$ is methylene.

39. The compound, or salt thereof, of claim 3 wherein A is methylene.

40. The compound, or salt thereof, of claim 4 wherein A is methylene.

41. The compound, or salt thereof, of claim 5 wherein A is methylene.

42. The compound, or salt thereof, of claim 7 wherein A is methylene.

43. The compound, or salt thereof, of claim 8 wherein A is methylene.

44. The compound, or salt thereof, of claim 9 wherein A is methylene.

* * * * *